(12) United States Patent
Capet et al.

(10) Patent No.: US 8,809,539 B2
(45) Date of Patent: Aug. 19, 2014

(54) DICARBOXYLIC ACID DERIVATIVES AS S1P1 RECEPTOR AGONISTS

(75) Inventors: Marc Capet, Melesse (FR); Nicolas Levoin, Mordelles (FR); Isabelle Berrebi-Bertrand, Pace (FR); Philippe Robert, Pace (FR); Jean-Charles Schwartz, Paris (FR); Jeanne-Marie Lecomte, Paris (FR); Jayraj Dilipbhai Aradhye, Baroda (IN); Muthukumaran Natarajan Pillai, Baroda (IN); Bhavesh Mohanbhai Panchal, Vallabh Vidyanagar (IN); Jignesh Kantilal Jivani, Rajkot (IN); Biswajit Samanta, Baroda (IN); Ranjan Kumar Pal, Baroda (IN); Rajamannar Thennati, Baroda (IN)

(73) Assignees: Bioprojet, Paris (FR); Sun Pharma Advanced Research Company Ltd, Mumbai (IN)

( * ) Notice: Subject to any disclaimer, the term of this patent is extended or adjusted under 35 U.S.C. 154(b) by 641 days.

(21) Appl. No.: 12/664,718

(22) PCT Filed: Jun. 16, 2008

(86) PCT No.: PCT/EP2008/057571
§ 371 (c)(1),
(2), (4) Date: May 10, 2010

(87) PCT Pub. No.: WO2008/152149
PCT Pub. Date: Dec. 18, 2008

(65) Prior Publication Data
US 2010/0249187 A1    Sep. 30, 2010

(30) Foreign Application Priority Data

Jun. 15, 2007  (EP) .................................. 07290748

(51) Int. Cl.
*C07D 211/18* (2006.01)
*A61K 31/445* (2006.01)
*C07D 413/10* (2006.01)

(52) U.S. Cl.
CPC .................................. *C07D 413/10* (2013.01)
USPC ............ 546/194; 546/209; 514/318; 514/326

(58) Field of Classification Search
CPC ..................................................... C07D 413/10
See application file for complete search history.

(56) References Cited

U.S. PATENT DOCUMENTS

| 7,199,142 B2 | 4/2007 | Chen et al. |
| 7,220,734 B2 | 5/2007 | Doherty et al. |
| 7,572,811 B2 | 8/2009 | Pan et al. |
| 2009/0264469 A1 | 10/2009 | Capet et al. |

OTHER PUBLICATIONS

International Search Report for PCT/EP2008/057571.

*Primary Examiner* — Heidi Reese
(74) *Attorney, Agent, or Firm* — B. Aaron Schulman, Esq.; Stites & Harbison,. PLLC.

(57) ABSTRACT

The present invention relates to new compounds of formula (I) possessing agonistic activity at sphingosine-1-phosphate (S1P) receptors, their process of preparation and their use as immunosuppressive agents. The invention is also directed to pharmaceutical compositions containing these compounds and use of these compounds for treatment/prevention of immune mediated diseases and conditions or inflammatory diseases and conditions.

36 Claims, No Drawings

DICARBOXYLIC ACID DERIVATIVES AS S1P1 RECEPTOR AGONISTS

The present invention relates to new compounds of formula (I) possessing agonistic activity at sphingosine-1-phosphate (S1P) receptors, their process of preparation and their use as immunosuppressive agents. The invention is also directed to pharmaceutical compositions containing these compounds and use of these compounds for treatment/prevention of immune mediated diseases and conditions or inflammatory diseases and conditions.

A class of 3-aryl or 5-aryl-1,2,4-oxadiazole based dicarboxylic acid derivatives has been found as potent spingosine-1-phosphate (S1P1/Edg1) receptor agonists with minimal affinity for S1P3 (Edg3) receptor subtype.

The lysophospholipids are recognized as components in the biosynthesis of cell membranes. The lysophospholipid S1P regulates diverse biological processes. Sphingosine-1-phosphate (S1P) is a bioactive lysolipid with pleiotropic functions mediated through a family of G protein coupled receptors, S1P1, S1P2, S1P3, S1P4 and S1P5. It regulates heart rate, coronary artery blood flow, endothelial integrity in lung and recirculation of lymphocytes (H. Rosen et al., *The J. Bio. Chem.*, 2004, 279, 13839-13848). Among other effects, indirect or direct S1P receptor agonists inhibit thymic egress and lymphocyte recirculation (Rosen et al, *Immunol. Rev.*, 2003, 195, 160). Inhibition of lymphocyte egress is associated with clinically useful immunosuppression or immuno-depression in both transplantation and autoimmune diseases.

Agonism of S1P receptors induces accelerated homing of lymphocytes to lymph nodes and Peyer's patches and blood lymphopenia without lymphodepletion. Such immunosuppression/depression is desirable to prevent rejection after organ, tissue or cell transplantation and in the treatment of autoimmune and certain inflammatory disorders. The potential clinical indications identified through several animal models involving S1P agonists include suppressed transplant rejection, multiple sclerosis, coronary artery vasospasm, sinus tachycardia, restenosis after coronary artery angioplasty, asthma, breast and liver cancer, chemotherapy and radiation induced infertility etc. (J, Chun et al, Trends Mol. Med., 2006, 12(2), 65-75).

FTY720, a synthetic analogue of the natural product myriocin, useful for the treatment of transplant rejection and human autoimmune diseases is currently in clinical trials for multiple sclerosis (J., Chun et al, *Trends Mol. Med.*, 2006, 12(2), 65-75). However, FTY720 is reported to have an adverse event of asymptomatic bradycardia (*J. Am. Soc. Nephrol.*, 2002, 13, 1073) associated with non selective agonism at the S1P3 receptor (*Bioorg. & Med. Chem. Lett.*, 2004, 14, 3501).

There is potential interest in developing direct S1P receptor agonists displaying receptor selectivity, particularly compounds with low relative activity at the S1P3 receptor subtype expressed in cardiac tissues and whose activation results in bradycardia and cardiac depression (S. Mandala et al., *JPET*, 2004, 309, 758-768; H. Rosen et al., *The J. Bio. Chem.*, 2004, 279, 13839-13848).

The object of the present invention is to provide novel compounds that are potent S1P1 receptor agonist with low affinity to S1P3/Edg3 receptor.

EP 1 650 186, WO 2005/082 089, WO 2004/058 149, WO 2003/105 771 and Hale et al., J. Med. Chem., 47(27), 6662-6665 disclose S1P1 agonists.

SUMMARY OF THE INVENTION

The present invention provides a novel class of 3-aryl or 5-aryl-1,2,4-oxadiazole based dicarboxylic acid derivatives useful as S1P1 receptor agonists, represented by a compound of formula (I):

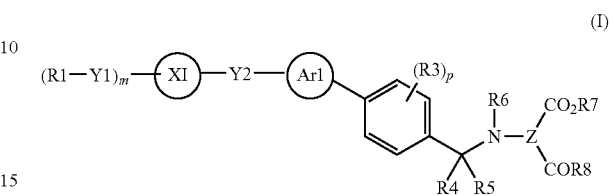

wherein Ar1, X1, R1, Y1, Y2, R3, R4, R5, R6, Z, $CO_2R7$ and COR8 are as defined below,
as well as their enantiomers, diastereomers, mixtures thereof and pharmaceutically acceptable salts, hydrates and solvates.

The present invention also provides pharmaceutical compositions comprising a pharmaceutically acceptable carrier and a therapeutically effective amount of at least one of the compounds of formula (I), as well as their enantiomers, diastereomers, mixtures thereof and pharmaceutically acceptable salts, hydrates and solvates.

The present invention also provides for use of the compound of formula (I) for treating immune mediated diseases and conditions or inflammatory diseases and conditions.

These and other objects, which will become apparent during the following detailed description have been achieved by the inventor's discovery that compounds of formula (I) are potent S1P1 receptor agonist with low affinity for S1P3 receptor.

DETAILED DESCRIPTION OF THE INVENTION

The present invention provides novel compounds represented by formula (I):

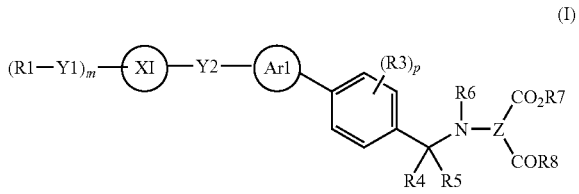

as well as their enantiomers, diastereomers, mixtures thereof and pharmaceutically acceptable salts, hydrates and solvates.

represents 1,2,4-oxadiazole group,

X1 is a mono-, bi- or tricyclic ring structure selected from aryl, heteroaryl, heterocyclic group or cycloalkyl group optionally comprising one or more unsaturations;

R1 is selected from the group consisting of hydrogen, halo, perhaloalkyl, perhaloalkoxy, aryl, arylalkyl, alkylaryl, alkyl, alkenyl, alkynyl, —$N(R2)_2$ and cycloalkyl optionally comprising one or more unsaturations; wherein the aryl group may be fused with a ring comprising 2 to 5 atoms selected from carbon or heteroatoms; further wherein each R1 is optionally substituted from one up to the maximum number of substitutable positions with a substituent independently selected from a group consisting of halo, alkyl, —Oalkyl, cycloalkyl, aryl, arylalkyl, alkylaryl and perhaloalkyl; and each R2 is independently selected from, hydrogen, -alkyl, -cycloalkyl, —CO—(O)r-alkyl, —CO—(O)r-cycloalkyl, —O—CO-alkyl, —O—CO-cycloalkyl, wherein r is 0 or 1;

Y1 represents a bond or Y1 is selected from a group consisting of —O—; —S(O)$_q$, wherein q is 0, 1 or 2; and —C=Q-, wherein Q is O, S, N—R' or N—OR', wherein R' is selected from hydrogen, -alkyl, -alkenyl, -alkynyl, -alkoxy, -cycloalkyl or -perhaloalkyl;

each moiety R1-Y1, identical or different, represents a group that is attached to the cyclic ring structure X1 and m is an integer selected from 1 to 9, wherein m represents the number of positions on X1 substituted with a R1-Y1 moiety;

Y2 represents a bond or Y2 is selected from a group consisting of —O—; —CH$_2$—; —C(O)O—; —C(O)NH—; —S(O)$_q$—, wherein q is 0, 1 or 2; and —C=Q—, wherein Q is O, S, N—(R')$_2$ or N—OR', wherein each R' is independently selected from hydrogen, -alkyl, -alkenyl, -alkynyl, -alkoxy, -cycloalkyl or -perhaloalkyl;

R3 is selected from the group consisting of hydrogen, halo, -alkyl, —O-alkyl, perhaloalkyl and —N(R2)$_2$ wherein R2 is as defined above; and p is an integer selected from 1 to 4;

R4 and R5 are independently selected from the group consisting of hydrogen, methyl and -cycloalkyl or R4 and R5 together with the C atom to which they are attached form a -cycloalkyl group;

R6 is selected from the group consisting of hydrogen, -alkyl, -alkenyl, -alkynyl and -cycloalkyl;

Z represents a -cycloalkyl group, or R6 and Z form together with the N atom to which they are attached a 5 to 8-membered heterocyclic ring;

the —CO$_2$R7 and —COR8 groups are attached to the same atom, wherein the —CO$_2$R7 group represents a —CO$_2$H group or an ester derivative thereof and the —COR8 group represents a —CO$_2$H group or an ester or an amide derivative thereof.

Unless specified otherwise, the terms used hereabove or hereafter have the meaning ascribed to them below:

"Halo" or "halogen" refers to fluorine, chlorine, bromine or iodine atom.

"Perhaloalkyl" represents a C1-C9-alkyl moiety wherein one or more hydrogen atoms are substituted with same or different halogen atoms, for example, —CF$_3$, —CHF$_2$, —CCl$_3$, —CF$_2$Cl, —CH$_2$Cl, —CH$_2$CF$_2$—CF$_3$.

"Perhaloalkoxy" represents a perhaloalkyl linked via an oxygen atom, for example, —O—CF$_3$, —O—CHF$_2$, —O—CH$_2$CF$_3$.

"Alkyl" represents an aliphatic-hydrocarbon group which may be straight or branched having 1 to 20 carbon atoms in the chain unless specified otherwise. Preferred alkyl groups have 1 to 12 carbon atoms, more preferably have 1 to 6 carbon atoms in the chain. Branched means that one or more lower alkyl groups such as methyl, ethyl or propyl are attached to a linear alkyl chain. Exemplary alkyl groups include methyl, ethyl, n-propyl, i-propyl, n-butyl, t-butyl, n-pentyl, 3-pentyl, octyl, nonyl, decyl.

"Alkenyl" refers to an aliphatic hydrocarbon group containing a carbon-carbon double bond and which may be straight or branched having 2 to 15 carbon atoms in the chain unless specified otherwise. Preferred alkenyl groups have 2 to 12 carbon atoms in the chain; and more preferably about 2 to 6 carbon atoms in the chain. Exemplary alkenyl groups include ethenyl, propenyl, n-butenyl, i-butenyl, 3-methylbut-2-enyl, n-pentenyl, heptenyl, octenyl, nonenyl, decenyl.

"Alkynyl" refers to an aliphatic hydrocarbon group containing a carbon-carbon triple bond and which may be straight or branched having 2 to 15 carbon atoms in the chain unless specified otherwise. Preferred alkynyl groups have 2 to 12 carbon atoms in the chain; and more preferably 2 to 4 carbon atoms in the chain. Exemplary alkynyl groups include ethynyl, propynyl, n-butynyl, 2-butynyl, 3-methyl-1-butynyl, n-pentynyl, 4,4-dimethyl-2-pentynyl, heptynyl, octynyl and decynyl.

"Cycloalkyl" refers to a non-aromatic mono- or multicyclic hydrocarbon ring system of 3 to 10 carbon atoms, preferably of 4 to 10 carbon atoms. Preferred ring sizes of rings of the ring system include 4 to 6 ring atoms. Exemplary monocyclic cycloalkyl include cyclopropyl, cyclobutyl, cyclopentyl, cyclohexyl, cycloheptyl, and the like. Exemplary multicyclic cycloalkyl include 1-decalin, norbornyl, adamant-(1- or 2-)yl.

"Aryl" refers to an aromatic monocyclic or multicyclic hydrocarbon ring system of 6 to 14 carbon atoms, preferably of 6 to 10 carbon atoms. Exemplary aryl groups include phenyl, naphthyl, indenyl, phenanthryl, biphenyl.

The terms "heterocycle" or "heterocyclic" refer to a saturated or partially unsaturated non aromatic stable 3 to 14, preferably 5 to 10-membered mono, bi or multicyclic rings wherein at least one member of the ring is a hetero atom. Typically, heteroatoms include, but are not limited to, oxygen, nitrogen, sulfur, selenium, and phosphorus atoms. Preferable heteroatoms are oxygen, nitrogen and sulfur. Suitable heterocycles are also disclosed in the *Handbook of Chemistry and Physics,* 76th Edition, CRC Press, Inc., 1995-1996, pages 2-25 to 2-26, the disclosure of which is hereby incorporated by reference.

Preferred non aromatic heterocyclic include, but are not limited to oxetanyl, tetrahydrofuranyl, dioxolanyl, tetrahydropyranyl, dioxanyl, pyrrolidinyl, piperidyl, morpholinyl, imidazolidinyl, pyranyl. Preferred aromatic heterocyclic, herein called heteroaryl groups include, but are not limited to, pyridyl, pyridyl-N-oxide, pyrimidinyl, pyrrolyl, imidazolinyl, pyrrolinyl, pyrazolinyl, furanyl, thienyl, imidazolyl, triazolyl, tetrazolyl, quinolyl, isoquinolyl, benzoimidazolyl, thiazolyl, pyrazolyl, and benzothiazolyl groups.

The term "heteroaryl" refers to a 5 to 14, preferably 5 to 10 membered aromatic hetero, mono-, bi- or multicyclic ring. Examples include pyrrolyl, pyridyl, pyrazolyl, thienyl, pyrimidinyl, pyrazinyl, tetrazolyl, indolyl, quinolinyl, purinyl, imidazolyl, thienyl, thiazolyl, benzothiazolyl, furanyl, benzofuranyl, 1,2,4-thiadiazolyl, isothiazolyl, triazoyl, tetrazolyl, isoquinolyl, benzothienyl, isobenzofuryl, pyrazolyl, carbazolyl, benzimidazolyl, isoxazolyl.

"Alkyl", "cycloalkyl", "alkenyl", "alkynyl", "aryl", "heteroaryl", "heterocycle" also refers to the corresponding "alkylene", "cycloalkylene", "alkenylene", "alkynylene", "arylene", "heteroarylene", "heterocyclene" which are formed by the removal of two hydrogen atoms.

In particular, R7 may be chosen from: H, -Alkyl, -perhaloalkyl, -Heterocycle, -Alkylheterocycle, -alkylaryl, -Alkyl-O—C(=O)-Alkyl, -Alkyl-O—C(=O)—OAlkyl, -Alkyl-C(=O)-Alkyl, -Alkyl-O—C(=O)—OCycloalkyl, where the Heterocycle is optionally substituted with =O, Alkyl.

In particular, R8 may be chosen from: OH, —OAlkyl; —Oalkylaryl, —OHeterocycle; —OAlkylheterocycle, wherein the heterocycle is optionally substituted with =O or alkyl; —OAlkyl-O—C(=O)-Alkyl; —OAlkyl-O—C(=O)—OAlkyl; —OAlkyl-C(=O)-Alkyl; —OAlkyl-C(=O)-Aryl wherein the aryl group is unsubstituted or substituted with one or more halogen or alkoxy groups; —OAlkyl-C(=O)—Heteroaryl; —OAlkyl-C(=O)—OAlkyl; —OAlkyl-C(=O)-Cycloalkyl; —OAlkyl-C(=O)—NTT' where T and T', identical or different, independently represent a hydrogen atom, an alkyl, a cycloalkyl, a hydroxycycloalkyl, a heteroaryl or a heterocyclic group, or T and T' form together with the N atom to which they are attached a N-containing Heterocycle optionally substituted with =O or alkyl; —OAlkyl-O—C(=O)—OCycloalkyl; —NR$^a$R$^b$, —NR$^a$OR$^b$, natural or synthetic amino acid, wherein each R$^a$ and R$^b$ are independently selected from hydrogen, alkyl, hydroxyalkyl, —O-alkyl, alkenyl, perhaloalkyl, —C3-C6cycloalkyl, heterocycle, heterocyclylalkyl and aryl, wherein g wherein the heterocycle moiety may be unsubstituted or substituted with alkyl or R$^a$ and R$^b$ together with the Nitrogen atom to which they are attached, may form a 5-6 membered heterocyclic ring containing 1-2 heteroatoms selected from O and N, wherein the ring is unsubstituted or substituted with hydroxy, hydroxyalkyl, hydroxyalcoxyalkyl, amino, alkylamino, dialkylamino, arylalcoxycarbonylamino, alcoxycarbonylamino.

In one preferred embodiment, the invention provides a compound of formula (I) wherein:

the —CO$_2$R7 group represents a —CO$_2$H group or an ester derivative thereof, wherein R7 represents a hydrogen or a C1-C3alkyl chain optionally comprising one or more unsaturations and optionally substituted by:

a) —O—CO(O)$_t$alkyl,
b) —O—CO(O)$_t$-cycloalkyl or
c) heterocyclic group, wherein t is 0 or 1, and the items a, b or c above are optionally substituted by one or more halo, —C1-C5-alkyl, or —CO group; and R8 represents —OH, —O-alkyl, OAlkyl-C(=O)-Alkyl.

Suitable ester derivatives of compound of formula (I) represented by —CO$_2$R7 and —COR8 groups, wherein R7 is an alkyl chain and R8 is —O-alkyl chain include the compounds wherein alkyl chain may be C1-C12alkyl. They are useful as prodrugs to provide compounds of the formula (I) wherein the —CO$_2$H group is formed in vivo following administration. Such esters are also useful as intermediates for the preparation of dicarboxylic acid compounds of the formula (I).

Examples of ester derivatives of a —CO$_2$H group are alkyl, alkanoyloxyalkyl (including alkyl, cycloalkyl or aryl substituted derivatives thereof), arylcarbonyl-oxyalkyl (including aryl substituted derivatives thereof), aryl, arylalkyl, indanyl and haloalkyl: wherein alkanoyl groups have from 2 to 12 carbon atoms, alkyl groups have from 1 to 12 carbon atoms and aryl means phenyl or naphthyl, both of which may be optionally substituted by —C1-C4alkyl, —O—C1-C4alkyl or halo. Alkyl, alkanoyl and alkoxy groups can, where appropriate, be straight- or branched-chain.

Specific examples of ester derivatives of a —CO$_2$H group are C1-C9alkyl (e.g. methyl, ethyl, n-propyl, isopropyl), benzyl, 1-(2,2-diethylbutanoyloxy)ethyl, (2-ethyl-propanoyloxy)methyl, 1-(2-ethylpropanoyloxy)ethyl, 1-(2,4-dimethylbenzoyloxy)-ethyl, (∝-benzoyloxy)benzyl, 1-(benzoyloxy)ethyl, 1-(2-methyl-1-propanoyloxy)-propyl, (2,4,6-trimethylbenzoyloxy)methyl, 1-(2,4,6-trimethyl-benzoyloxy)ethyl, (pivaloyloxy)methyl, phenethyl, phenpropyl, 2,2,2-trifluoroethyl, 1- or 2-naphthyl, 2,4-dimethylphenyl, 4-t-butylphenyl, 5-indanyl, axetil, cilxetil, mofetil, pivoxetil, proxetil, (tetrahydropyran-4-yloxycarbonyloxy)methyl, (dioxolan-5-yloxycarbonyl-oxy)methyl, 1-(tetrahydropyran-4-yloxycarbonyloxy)ethyl, 1-(dioxolan-5-yloxy-carbonyloxy) ethyl, medoxomil and soproxil.

Examples of amide derivatives of a —CO$_2$H group are NHalkyl, NHcyclolkyl, NHalkenyl, NHalkynyl, NHalkaryl, NHheteroaryl, NHaryl, NH(natural or unnatural/synthetic amino acids as mono or oligopeptides).

Specific examples of amide derivatives of a —CO$_2$H group are NHMe, NHEt, NH-t-Bu, NHallyl, NHpropargyl, NHCH$_2$Furyl, NH(2-CF$_3$-Phenyl), NHFuryl.

Examples of natural or synthetic amino acids include lysine, valine, phenylalanine, alanine, glycine, norvaline, cycloleucine and the like.

The term "prodrug" means a pharmacologically acceptable derivative, for example, an amide or ester (such as a biolabile ester derivative of a —CO$_2$H group) that is biotransformed to the compound of the present invention. A general reference on prodrugs is Goodman and Gilmans, *The Pharmacological Basis of Therapeutics*, 8$^{th}$ Edition, McGraw-Hill, Int. Ed. 1992, "Biotrans-formation of Drugs", p. 13-15.

The term "solvate" refers to an aggregate that comprises a compound of the invention, with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms.

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Geometric isomers of double bonds such as olefins and C=N can also be present in the compounds described here, all the stable isomers are contemplated here. All chiral, diastereomeric, racemic forms and all geometric isomeric forms of a compound are intended, unless the stereochemistry or the isomeric form is specifically indicated. All processes used to synthesize the compounds of the present invention are considered as part of the present invention.

The term "substituted" as used herein means that any one or more hydrogens on the designated atom is replaced with a selection from the indicated group, provided that the designated atom's normal valency is not exceeded and that the substitution results in a stable compound.

As used herein, the term "patient" refers to a warm-blooded animal such as a mammal, preferably a human or a human child, which is afflicted with, or has the potential to be afflicted with one or more diseases and conditions described herein.

As used herein, a "therapeutically effective amount" refers to an amount of a compound of the present invention which is effective in reducing, eliminating, treating or controlling the symptoms of the herein-described diseases and conditions. The term "controlling" is intended to refer to all processes wherein there may be a slowing, interrupting, arresting, or stopping of the progression of the diseases and conditions described herein, but does not necessarily indicate a total elimination of all disease and condition symptoms, and is intended to include prophylactic treatment and chronic use.

As used herein, the expression "pharmaceutically acceptable" refers to those compounds, materials, compositions, or dosage forms which are, within the scope of sound medical judgment, suitable for contact with the tissues of human beings and animals without excessive toxicity, irritation, allergic response, or other problem complications commensurate with a reasonable benefit/risk ratio.

As used herein, "pharmaceutically acceptable salts" refer to derivatives of the disclosed compounds wherein the parent compound is modified by making acid or base salts thereof. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, tartaric, citric, methanesulfonic, benzenesulfonic, glucoronic, glutamic, benzoic, salicylic, toluenesulfonic, oxalic, fumaric, maleic, and the like. Further addition salts include ammonium salts such as tromethamine, meglumine, epolamine, etc., metal salts such as sodium, potassium, calcium, zinc or magnesium.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Generally, non-aqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418 and P. H. Stahl, C. G. Wermuth, *Handbook of Pharmaceutical salts—Properties, Selection and Use*, Wiley-VCH, 2002, the disclosures of which are hereby incorporated by reference.

The compounds of the general formula (I) having geometrical and stereoisomers are also a part of the invention.

The present invention also embraces any of the following preferred embodiments or any of the combinations thereof:

In one embodiment, the present invention provides a compound of formula (I-A):

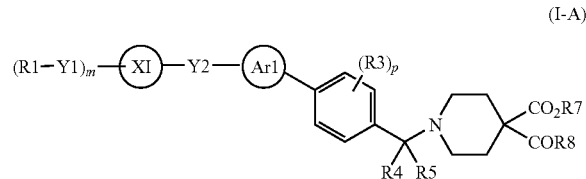
(I-A)

as well as their enantiomers, diastereomers, mixtures thereof and pharmaceutically acceptable salts, hydrates and solvates, wherein:
X1, R1, Y1, Y2, Ar1, R3, R4, R5, m, p, R7, R8 are defined as in formula (I).

Preferably, the invention provides compound of formula (I-A) wherein:
Ar1 is

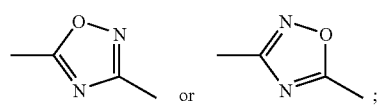

X1 is phenyl;
each R1, identical or different, is selected from the group consisting of hydrogen, halo, perhaloalkyl, perhaloalkoxy, aryl, arylalkyl, alkylaryl, alkyl, alkenyl, alkynyl, and cycloalkyl optionally comprising one or more unsaturations, wherein the aryl group may be fused with a ring comprising 2 to 5 atoms selected from carbon or heteroatoms; further wherein each R1 is optionally substituted from one up to maximum number of substitutable positions with a substituent independently selected from a group consisting of halo, -alkyl, —O-alkyl, cycloalkyl, aryl, arylalkyl, alkylaryl and perhaloalkyl;

Y1 represents a bond or Y1 is selected from a group consisting of —O—; —S(O)$_q$—, wherein q is 0, 1 or 2; and —C=Q-, wherein Q is O or S;

the moiety R1-Y1 represents a group that is attached to the cyclic ring structure X1 and m is an integer selected from 1 to 5, wherein m represents the number of positions on X1 available for attachment of R1-Y1 moiety; and wherein each R1-Y1 may be identical or different group;

Y2 represents a bond or Y2 is —CH$_2$— or —C=Q-, wherein Q is N—OR', wherein each R' is independently selected from hydrogen, -alkyl, -alkenyl and -alkynyl;

R3 is hydrogen and p is 4;

R4 and R5 are independently selected from the group consisting of hydrogen and methyl;

the —CO$_2$R7 and —COR8 groups are attached to the same atom, wherein the —CO$_2$R7 group represents a —CO$_2$H group or an ester derivative thereof and the —COR8 group represents a —CO$_2$H group or an ester or an amide derivative thereof.

In another embodiment, the present invention provides compound of formula (I-B):

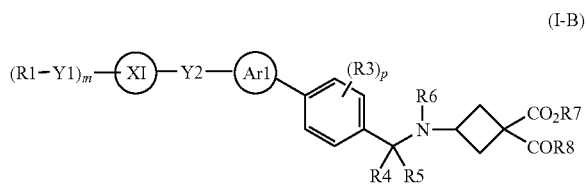
(I-B)

as well as their enantiomers, diastereomers, mixtures thereof and pharmaceutically acceptable salts, hydrates and solvates, wherein X1, R1, Y1, Y2, Ar1, R3, R4, R5, R6, m, p, R7, R8 are defined as in formula (I).

In another embodiment, the present invention provides a compound of formula (I-C):

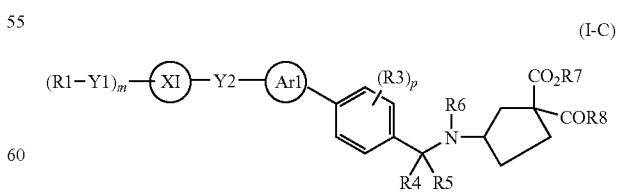
(I-C)

as well as their enantiomers, diastereomers, mixtures thereof and pharmaceutically acceptable salts, hydrates and solvates, wherein X1, R1, Y1, Y2, Ar1, R3, R4, R5, R6, m, p, R7, R8 are defined as in formula (I).

In another embodiment, the present invention provides a compound of formula (I-D):

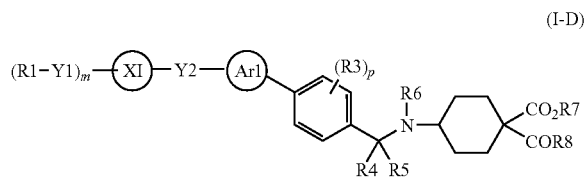

as well as their enantiomers, diastereomers, mixtures thereof and pharmaceutically acceptable salts, hydrates and solvates, wherein X1, R1, Y1, Y2, Ar1, R3, R4, R5, R6, m, p, R7, R8 are defined as in formula (I).

In yet another embodiment, the present invention provides compound of formula (I-E) and pharmaceutically acceptable salts thereof:

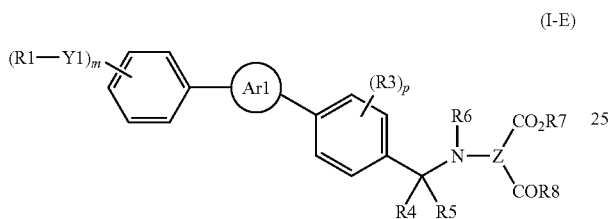

as well as their enantiomers, diastereomers, mixtures thereof and pharmaceutically acceptable salts, hydrates and solvates, wherein:
R1, m, X1, Ar1, R3, R4, R5, R6, R7, R8, p are defined as above.

In another embodiment, the present invention provides a compound of formula (I-F):

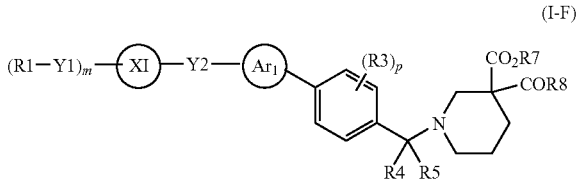

as well as their enantiomers, diastereomers, mixtures thereof and pharmaceutically acceptable salts, hydrates and solvates, wherein: X1, R1, Y1, Y2, Ar1, R3, R4, R5, R6, m, p, R7, R8 are defined as in formula (I).

Preferably, in anyone of formulae (I), (I-A), (I-B), (I-C), (I-D), (I-E) or (I-F), Ar1 represents

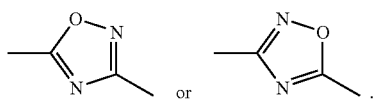

Preferably, in anyone of formulae (I), (I-A), (I-B), (I-C), (I-D), or (I-F) Y2 represents a bond or —CH$_2$—; more preferably, Y2 represents a bond.

Preferably, in anyone of formulae (I), (I-A), (I-B), (I-C), (I-D), (I-E) or (I-F), Y1 represents a bond or —O—, —S(O) p-, —C=Q-, as defined above; more preferably, Y1 represents a bond.

Preferably, in anyone of formulae (I), (I-A), (I-B), (I-C), (I-D) or (I-F), X1 represents a phenyl group.

Preferably, in anyone of formulae (I), (I-A), (I-B), (I-C), (I-D), (I-E) or (I-F), R3 represents a hydrogen.

Preferably, in anyone of formulae (I), (I-A), (I-B), (I-C), (I-D), (I-E) or (I-F), R4 and R5 represent a hydrogen.

Preferably, in anyone of formulae (I), (I-A), (I-B), (I-C), (I-D), (I-E) or (I-F), R6 represents a hydrogen or alkyl and Z represents a cycloalkyl, R6 and Z form together with the N atom to which they are attached a 6-membered heterocycle.

Preferably, in anyone of formulae (I), (I-A), (I-B), (I-C), (I-D), (I-E) or (I-F), each R1, identical or different, is selected from a halo, an aryl, arylalkyl, -alkylaryl, alkyl, alkenyl, cycloalkyl, each being optionally substituted as defined above; more preferably, R1 is selected from an optionally substituted aryl group and a halo as defined above.

More preferred compounds are those of formula (I-A) wherein:
Ar1 is

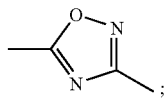

Y1 is a bond;
m=2;
one of R1 is a halo atom and the other R1 is a phenyl group;
each R3 is H;
R4=R5=H;
R7=H; and
COR8 is CO$_2$H or an ester or an amid thereof; including R8=OAlkyl or OAlkylC(=O)-Alkyl,
as well as their enantiomers, diastereomers, mixtures thereof and pharmaceutically acceptable salts, hydrates and solvates.

In one preferred embodiment, the present invention provides a compound selected from the group consisting of:
1-{4-[5-(4-isobutylphenyl)-1,2,4-oxadiazol-3-yl]benzyl}piperidine-4,4-dicarboxylic acid
1-(4-{5-[4-(3-methylbut-2-enyloxy)phenyl]-1,2,4-oxadiazol-3-yl}benzyl)piperidine-4,4-dicarboxylic acid
1-{4-[5-(2-fluorobiphenyl-4-yl)-1,2,4-oxadiazol-3-yl]benzyl}piperidine-4,4-dicarboxylic acid
monomethyl 1-{4-[5-(2-fluorobiphenyl-4-yl)-1,2,4-oxadiazol-3-yl]benzyl}piperidine-4,4-dicarboxylate
1-{4-[5-(4-cyclopropylmethylphenyl)-1,2,4-oxadiazol-3-yl]benzyl}piperidine-4,4-dicarboxylic acid
monomethyl 1-{4-[5-(4-cyclopropylmethylphenyl)-1,2,4-oxadiazol-3-yl]benzyl}piperidine-4,4-dicarboxylate
monomethyl 1-(4-{5-[4-(3-methyl-but-2-enyloxy)phenyl]-1,2,4-oxadiazol-3-yl}benzyl)piperidine-4,4-dicarboxylate
monomethyl 1-{4-[5-(4-isobutylphenyl)-1,2,4-oxadiazol-3-yl]benzyl}piperidine-4,4-dicarboxylate
monomethyl 1-{4-[5-(2,2-dimethyl-2,3-dihydrobenzofuran-5-yl)-1,2,4-oxadiazol-3-yl]benzyl}piperidine-4,4-dicarboxylate
1-{4-[5-(2,2-dimethyl-2,3-dihydro-1-benzofuran-5-yl)-1,2,4-oxadiazol-3-yl]benzyl}piperidine-4,4-dicarboxylic acid
1-{4-[5-(2',4'-difluorobiphenyl-4-yl)-1,2,4-oxadiazol-3-yl]benzyl}piperidine-4,4-dicarboxylic acid
1-{4-[5-(4'-fluorobiphenyl-4-yl)-1,2,4-oxadiazol-3-yl]benzyl}piperidine-4,4-dicarboxylic acid 1-{4-[5-(3',5'-difluorobiphenyl-4-yl)-1,2,4-oxadiazol-3-yl]
benzyl}piperidine-4,4-dicarboxylic acid
1-{4-[5-(4-trifluoromethylphenyl)-1,2,4-oxadiazol-3-yl]
benzyl}piperidine-4,4-dicarboxylic acid
1-[4-(5-biphenyl-4-yl-1,2,4-oxadiazol-3-yl)benzyl]piperidine-4,4-dicarboxylic acid
1-{4-[5-(4-trifluoromethoxyphenyl)-1,2,4-oxadiazol-3-yl]
benzyl}piperidine-4,4-dicarboxylic acid
1-{4-[5-(2,3-difluorophenyl)-1,2,4-oxadiazol-3-yl]
benzyl}piperidine-4,4-dicarboxylic acid
1-{4-[5-(4-methanesulfonylphenyl)-1,2,4-oxadiazol-3-yl]
benzyl}piperidine-4,4-dicarboxylic acid
1-(4-{5-[4-(4-chlorophenyl)cyclohexyl]-1,2,4-oxadiazol-3-yl}benzyl)piperidine-4,4-dicarboxylic acid
1-{4-[5-(1,1-dimethyl-1,3-dihydro-2-benzofuran-5-yl)-1,2,4-oxadiazol-3-yl]benzyl}piperidine-4,4-dicarboxylic acid
1-(4-{5-[4-(2,2,2-trifluoroethoxy)phenyl]-1,2,4-oxadiazol-3-yl}benzyl)piperidine-4,4-dicarboxylic acid
1-{4-[5-(furan-2-ylmethoxyiminomethyl)-1,2,4-oxadiazol-3-yl]benzyl}piperidine-4,4-dicarboxylic acid
1-{4-[5-(4-benzylphenyl)-1,2,4-oxadiazol-3-yl]
benzyl}piperidine-4,4-dicarboxylic acid
1-{4-[5-(4-isopropylcyclohexyl)-1,2,4-oxadiazol-3-yl]
benzyl}piperidine-4,4-dicarboxylic acid
1-{4-[5-(4-isopropenylcyclohex-1-enyl)-1,2,4-oxadiazol-3-yl]benzyl}piperidine-4,4-dicarboxylic acid
1-{4-[3-(1,1-dimethyl-1,3-dihydro-2-benzofuran-5-yl)-1,2,4-oxadiazol-5-yl]benzyl}piperidine-4,4-dicarboxylic acid
1-{4-[3-(2-fluorobiphenyl-4-yl)-1,2,4-oxadiazol-5-yl]
benzyl}piperidine-4,4-dicarboxylic acid
1-{4-[5-(6,6-dimethylbicyclo[3.1.1]hept-2-en-2-ylmethyl)-1,2,4-oxadiazol-3-yl]benzyl}piperidine-4,4-dicarboxylic acid
1-{4-[5-(4-benzoylphenyl)-1,2,4-oxadiazol-3-yl]
benzyl}piperidine-4,4-dicarboxylic acid
1-{4-[5-(6-methoxynaphthalen-2-yl)-1,2,4-oxadiazol-3-yl]
benzyl}piperidine-4,4-dicarboxylic acid
1-{4-[5-(4-benzyl-2,3-difluorophenyl)-1,2,4-oxadiazol-3-yl]benzyl}piperidine-4,4-dicarboxylic acid
1-{4-[5-(4-isobutyrylphenyl)-1,2,4-oxadiazol-3-yl]
benzyl}piperidine-4,4-dicarboxylic acid
1-(4-{5-[4-(2,3-difluorobenzyl)phenyl]-1,2,4-oxadiazol-3-yl}benzyl)piperidine-4,4-dicarboxylic acid
1-{4-[5-(4-ethoxyphenyl)-1,2,4-oxadiazol-3-yl]
benzyl}piperidine-4,4-dicarboxylic acid
1-{4-[5-(4-tert-butylphenyl)-1,2,4-oxadiazol-3-yl]
benzyl}piperidine-4,4-dicarboxylic acid
1-{4-[5-(4-isopropoxyphenyl)-1,2,4-oxadiazol-3-yl]
benzyl}piperidine-4,4-dicarboxylic acid
1-{4-[5-(4-cyclohexylphenyl)-1,2,4-oxadiazol-3-yl]
benzyl}piperidine-4,4-dicarboxylic acid
mono-1-(acetyloxy)ethyl 1-{4-[5-(2-fluorobiphenyl-4-yl)-1,2,4-oxadiazol-3-yl]benzyl}piperidine-4,4-dicarboxylate
mono(2,2-dimethylpropanoyloxy)methyl 1-{4-[5-(2-fluorobiphenyl-4-yl)-1,2,4-oxadiazol-3-yl]benzyl}piperidine-4,4-dicarboxylate
mono-5-methyl-2-oxo[1,3]dioxol-4-ylmethyl 1-{4-[5-(2-fluorobiphenyl-4-yl)-1,2,4-oxadiazol-3-yl]
benzyl}piperidine-4,4-dicarboxylate
mono(isopropoxycarbonyloxy)methyl 1-{4-[5-(2-fluorobiphenyl-4-yl)-1,2,4-oxadiazol-3-yl]benzyl}piperidine-4,4-dicarboxylate
mono-1-(cyclohexyloxycarbonyloxy)ethyl 1-{4-[5-(2-fluorobiphenyl-4-yl)-1,2,4-oxadiazol-3-yl]benzyl}piperidine-4,4-dicarboxylate
1-(acetyloxy)ethyl methyl 1-{4-[5-(2-fluorobiphenyl-4-yl)-1,2,4-oxadiazol-3-yl]benzyl}piperidine-4,4-dicarboxylate
1-(acetyloxy)ethyl methyl 1-{4-[5-(4-isobutylphenyl)-1,2,4-oxadiazol-3-yl]benzyl}piperidine-4,4-dicarboxylate
(isopropoxycarbonyloxy)methyl methyl 1-{4-[5-(2-fluorobiphenyl-4-yl)-1,2,4-oxadiazol-3-yl]benzyl}piperidine-4,4-dicarboxylate
methyl 5-methyl-2-oxo-[1,3]dioxol-4-ylmethyl 1-{4-[5-(2-fluorobiphenyl-4-yl)-1,2,4-oxadiazol-3-yl]
benzyl}piperidine-4,4-dicarboxylate
di(isopropoxycarbonyloxy)methyl 1-{4-[5-(2-fluorobiphenyl-4-yl)-1,2,4-oxadiazol-3-yl]benzyl}piperidine-4,4-dicarboxylate
3-{4-[5-(4-isobutylphenyl)-1,2,4-oxadiazol-3-yl]
benzylamino}cyclobutane-1,1-dicarboxylic acid
3-{4-[5-(2-fluorobiphenyl-4-yl)-1,2,4-oxadiazol-3-yl]
benzylamino}cyclobutane-1,1-dicarboxylic acid
3-({4-[5-(4-isobutylphenyl)-1,2,4-oxadiazol-3-yl]
benzyl}methylamino)cyclobutane-1,1-dicarboxylic acid
3-({4-[5-(2-fluorobiphenyl-4-yl)-1,2,4-oxadiazol-3-yl]
benzyl}methylamino)cyclo-butane-1,1-dicarboxylic acid
monomethyl 3-({4-[5-(2-fluorobiphenyl-4-yl)-1,2,4-oxadiazol-3-yl]benzyl}methyl-amino)cyclobutane-1,1-dicarboxylate
monomethyl 3-({4-[5-(4-isobutylphenyl)-1,2,4-oxadiazol-3-yl]benzyl}methyl-amino)cyclobutane-1,1-dicarboxylate
monomethyl 3-({4-[5-(4-isobutylphenyl)-1,2,4-oxadiazol-3-yl]benzyl}methyl-amino)cyclobutane-1,1-dicarboxylate
3-{4-[5-(4-isobutylphenyl)-1,2,4-oxadiazol-3-yl]
benzylamino}cyclopentane-1,1-dicarboxylic acid
3-{4-[5-(4-cyclopropyl methyl phenyl)-1,2,4-oxadiazol-3-yl]benzylamino}cyclopentane-1,1-dicarboxylic acid
4-{4-[5-(4-isobutylphenyl)-1,2,4-oxadiazol-3-yl]
benzylamino}cyclohexane-1,1-dicarboxylic acid
4-{4-[5-(2-fluorobiphenyl-4-yl)-1,2,4-oxadiazol-3-yl]
benzylamino}cyclohexane-1,1-dicarboxylic acid
4-({4-[5-(2-fluorobiphenyl-4-yl)-1,2,4-oxadiazol-3-yl]
benzyl}methyl-amino)cyclohexane-1,1-dicarboxylic
acid;
1-{4-[5-(2-fluoro-biphenyl-4-yl)-[1,2,4]oxadiazol-3-yl]-benzyl}-piperidine-4,4-dicarboxylic acid, 2-oxo-3,3-dimethylbutyl ester
1-{4-[5-(2-Fluoro-biphenyl-4-yl)-[1,2,4]oxadiazol-3-yl]-benzyl}piperidine-4,4-dicarboxylic acid (2-oxo-2-phenyl-ethyl)ester
1-{4-[5-(2-Fluoro-biphenyl-4-yl)-[1,2,4]oxadiazol-3-yl]-benzyl}piperidine-4,4-dicarboxylic acid (2-oxo-propyl) ester
1-{4-[5-(2-Fluoro-biphenyl-4-yl)-[1,2,4]oxadiazol-3-yl]-benzyl}-piperidine-4,4-dicarboxylic acid (2-furan-2-yl-2-oxo-ethyl)ester
1-{4-[5-(2-Fluoro-biphenyl-4-yl)-[1,2,4]oxadiazol-3-yl]-benzyl}-piperidine-4,4-dicarboxylic acid [2-(4-chlorophenyl)-2-oxo-ethyl]ester
1-{4-[5-(2-Fluoro-biphenyl-4-yl)-[1,2,4]oxadiazol-3-yl]-benzyl}piperidine-4,4-dicarboxylic acid (2-morpholin-4-yl-ethyl)ester
1-{4-[5-(2-Fluoro-biphenyl-4-yl)-[1,2,4]oxadiazol-3-yl]-benzyl}-piperidine-4,4-dicarboxylic acid ethoxycarbonylmethylester
1-{4-[5-(2-Fluoro-biphenyl-4-yl)-[1,2,4]oxadiazol-3-yl]-benzylpiperidine-4,4-dicarboxylic acid (3-methyl-2-oxo-butyl)ester
1-{4-[5-(2-Fluoro-biphenyl-4-yl)-[1,2,4]oxadiazol-3-yl]-benzyl}-piperidine-4,4-dicarboxylic acid [2-(4-methoxyphenyl)-2-oxo-ethyl]ester 1-{4-[5-(2-Fluoro-biphenyl-4-yl)-[1,2,4]oxadiazol-3-yl]-benzyl}-piperidine-4,4-dicarboxylic acid (2-cyclopropyl-2-oxo-ethyl)ester 1-{4-[5-(2-Fluoro-biphenyl-4-yl)[1,2,4]-oxadiazol-3-yl]-benzyl}-piperidine-4,4-dicarboxylic acid [2-oxo-2-(2-oxopyrrolidin-1-yl)-ethyl]ester 1-{4-[5-(2-Fluoro-biphenyl-4-yl)-[1,2,4]-oxadiazol-3-yl]-benzyl}-piperidine-4,4-dicarboxylic acid dimethylcarbamoylmethyl ester 1-{4-[5-(2-Fluoro-biphenyl-4-yl)-[1,2,4]-oxadiazol-3-yl]-benzyl}-piperidine-4,4-dicarboxylic acid benzyl ester 3,3-dimethyl-2-oxo-butyl ester 1-{4-[5-(2-Fluoro-biphenyl-4-yl)-[1,2,4]-oxadiazol-3-yl]-benzyl}-piperidine-4,4-dicarboxylic acid benzyl ester 3-methyl-2-oxo-butyl ester 1-{4-[5-(2-Fluoro-biphenyl-4-yl)-[1,2,4]-oxadiazol-3-yl]-benzyl}-piperidine-4,4-dicarboxylic acid methylcarbamoylmethyl ester 1-{4-[5-(2-Fluoro-biphenyl-4-yl)-[1,2,4]-oxadiazol-3-yl]-benzyl}-piperidine-4,4-dicarboxylic acid (tert-butylcarbamoyl-methyl)ester 1-{4-[5-(2-Fluoro-biphenyl-4-yl)-[1,2,4]-oxadiazol-3-yl]-benzyl}-piperidine-4,4-dicarboxylic acid ethylcarbamoylmethyl ester 1-{4-[5-(2-Fluoro-biphenyl-4-yl)-[1,2,4]-oxadiazol-3-yl]-benzyl}-piperidine-4,4-dicarboxylic acid [2-oxo-2-(pyrrolidin-1-yl)-ethyl]ester 1-{4-[5-(2-Fluoro-biphenyl-4-yl)-[1,2,4]-oxadiazol-3-yl]-benzyl}-piperidine-4,4-dicarboxylic acid [2-oxo-(2-piperidin-1-yl)-ethyl]ester 1-{4-[5-(2-Fluoro-biphenyl-4-yl)-[1,2,4]-oxadiazol-3-yl]-benzyl}-piperidine-4,4-dicarboxylic acid (isopropylcarbamoyl-methyl)ester 1-{4-[5-(2-Fluoro-biphenyl-4-yl)-[1,2,4]-oxadiazol-3-yl]-benzyl}-piperidine-4,4-dicarboxylic acid cyclopropylcarbamoylmethyl ester 1-{4-[5-(2-Fluoro-biphenyl-4-yl)-[1,2,4]-oxadiazol-3-yl]-benzyl}-piperidine-4,4-dicarboxylic acid (isobutylcarbamoyl-methyl)ester 1-{4-[5-(2-Fluoro-biphenyl-4-yl)-[1,2,4]oxadiazol-3-yl]-benzyl}-piperidine-4,4-dicarboxylic acid carbamoylmethyl ester 1-{4-[5-(2-Fluoro-biphenyl-4-yl)-[1,2,4]oxadiazol-3-yl]-benzyl}-piperidine-4,4-dicarboxylic acid butylcarbamoylmethyl ester 1-{4-[5-(2-Fluoro-biphenyl-4-yl)-[1,2,4]oxadiazol-3-yl]-benzyl}-piperidine-4,4-dicarboxylic acid cyclopentylcarbamoylmethyl ester 1-{4-[5-(2-Fluoro-biphenyl-4-yl)-[1,2,4]oxadiazol-3-yl]-benzyl}-piperidine-4,4-dicarboxylic acid (piperidin-1-ylcarbamoylmethyl)ester 1-{4-[5-(2-Fluoro-biphenyl-4-yl)-[1,2,4]-oxadiazol-3-yl]-benzyl}-piperidine-4,4-dicarboxylic acid cyclohexylcarbamoylmethyl ester 1-{4-[5-(2-Fluoro-biphenyl-4-yl)-[1,2,4]oxadiazol-3-yl]-benzyl}-piperidine-4,4-dicarboxylic acid cyclobutylcarbamoylmethyl ester 1-{4-[5-(2-Fluoro-biphenyl-4-yl)-[1,2,4]oxadiazol-3-yl]-benzyl}-piperidine-4,4-dicarboxylic acid butanoyloxymethyl ester 1-{4-[5-(2-Fluoro-biphenyl-4-yl)-[1,2,4]-oxadiazol-3-yl]-benzyl}-piperidine-4,4-dicarboxylic acid [(4-hydroxy-cyclohexyl-carbamoyl)methyl]ester 1-{4-[5-(2-Fluoro-biphenyl-4-yl)-[1,2,4]-oxadiazol-3-yl]-benzyl}-piperidine-4,4-dicarboxylic acid (pyridin-2-yl-carbamoylmethyl)ester 1-{4-[5-(2-Fluoro-biphenyl-4-yl)-[1,2,4]-oxadiazol-3-yl]-benzyl}-4-(piperidin-1-ylcarbamoyl)-piperidine-4-carboxylic acid 1-{4-[5-(2-Fluoro-biphenyl-4-yl)-[1,2,4]-oxadiazol-3-yl]-benzyl}-4-(pyrrolidin-1-ylcarbamoyl)-piperidine-4-carboxylic acid 1-{4-[5-(2-Fluoro-biphenyl-4-yl)-[1,2,4]oxadiazol-3-yl]-benzyl}-piperidine-4,4-dicarboxylic acid pentyl ester 1-{4-[5-(2-Fluoro-biphenyl-4-yl)-[1,2,4]-oxadiazol-3-yl]-benzyl}-piperidine-4,4-dicarboxylic acid phenethyl ester 1-{4-[5-(2-Fluoro-biphenyl-4-yl)-[1,2,4]-oxadiazol-3-yl]-benzyl}-piperidine-4,4-dicarboxylic acid (2,2,2-trifluoro-ethyl)ester 1-{4-[5-(2-Fluoro-biphenyl-4-yl)-[1,2,4]oxadiazol-3-yl]-benzyl}-piperidine-4,4-dicarboxylic acid (3-methyl-oxetan-3-ylmethyl)ester 1-{4-[5-(2-Fluoro-biphenyl-4-yl)[1,2,4]-oxadiazol-3-yl]-benzyl}-piperidine-3,3-dicarboxylic acid 1-{4-[5-(4-Isobutyl-phenyl)-[1,2,4]-oxadiazol-3-yl]-benzyl}-piperidine-3,3-dicarboxylic acid 1-{4-[5-(4-Cyclohexyl-phenyl)-[1,2,4]-oxadiazol-3-yl]-benzyl}-piperidine-3,3-dicarboxylic acid 1-[4-(5-Biphenyl-4-yl-[1,2,4]-oxadiazol-3-yl)-benzyl]-piperidine-3,3-dicarboxylic acid 1-{4-[5-(2-Fluoro-biphenyl-4-yl)-[1,2,4]-oxadiazol-3-yl]-benzyl}-4-isobutylcarbamoyl-piperidine-4-carboxylic acid 1-{4-[5-(2-Fluoro-biphenyl-4-yl)-[1,2,4]-oxadiazol-3-yl]-benzyl}-4-(2-hydroxy-ethyl-carbamoyl)-piperidine-4-carboxylic acid 1-{4-[5-(2-Fluoro-biphenyl-4-yl)-[1,2,4]-oxadiazol-3-yl]-benzyl}-4-isopropylcarbamoyl-piperidine-4-carboxylic acid 4-Cyclopropylcarbamoyl-1-{4-[5-(2-fluoro-biphenyl-4-yl)-[1,2,4]-oxadiazol-3-yl]-benzyl}-piperidine-4-carboxylic acid 4-tert-Butylcarbamoyl-1-{4-[5-(2-fluoro-biphenyl-4-yl)-[1,2,4]-oxadiazol-3-yl]-benzyl}-piperidine-4-carboxylic acid 4-[(I-Ethyl-pyrrolidin-2-ylmethyl)-carbamoyl]-1-{4-[5-(2-fluoro-biphenyl-4-yl)-[1,2,4]oxadiazol-3-yl]-benzyl}-piperidine-4-carboxylic acid 1-{4-[5-(2-Fluoro-biphenyl-4-yl)-[1,2,4]-oxadiazol-3-yl]-benzyl}-4-(2-hydroxy-1-hydroxymethyl-ethylcarbamoyl)-piperidine-4-carboxylic acid 4-(2,3-Dihydroxy-propylcarbamoyl)-1-{4-[5-(2-fluoro-biphenyl-4-yl)-[1,2,4]-oxadiazol-3-yl]-benzyl}-piperidine-4-carboxylic acid 1-{4-[5-(2-Fluoro-biphenyl-4-yl)-[1,2,4]-oxadiazol-3-yl]-benzyl}-4-methylcarbamoyl-piperidine-4-carboxylic acid 4-Ethylcarbamoyl-1-{4-[5-(2-fluoro-biphenyl-4-yl)-[1,2,4]oxadiazol-3-yl]-benzyl}-piperidine-4-carboxylic acid 1-{4-[5-(2-Fluoro-biphenyl-4-yl)-[1,2,4]-oxadiazol-3-yl]-benzyl}-4-(piperidine-1-carbonyl)-piperidine-4-carboxylic acid 1-{4-[5-(2-Fluoro-biphenyl-4-yl)-[1,2,4]-oxadiazol-3-yl]-benzyl}-4-[4-(2-hydroxy-ethyl)-piperazine-1-carbonyl]-piperidine-4-carboxylic acid 4-Dimethylcarbamoyl-1-{4-[5-(2-fluoro-biphenyl-4-yl)-[1,2,4]oxadiazol-3-yl]-benzyl}-piperidine-4-carboxylic acid 1-{4-[5-(2-Fluoro-biphenyl-4-yl)-[1,2,4]-oxadiazol-3-yl]-benzyl}-4-(pyrrolidin-1-yl-carbonyl)-piperidine-4-carboxylic acid 4-Cyclohexylcarbamoyl-1-{4-[5-(2-fluoro-biphenyl-4-yl)-[1,2,4]oxadiazol-3-yl]-benzyl}-piperidine-4-carboxylic acid 1-{4-[5-(2-Fluoro-biphenyl-4-yl)-[1,2,4]-oxadiazol-3-yl]-benzyl}-4-(morpholin-4-yl-carbonyl)piperidine-4-carboxylic acid 4-Cyclobutylcarbamoyl-1-{4-[5-(2-fluoro-biphenyl-4-yl)-[1,2,4]-oxadiazol-3-yl]-benzyl}-piperidine-4-carboxylic acid 4-Cyclopentylcarbamoyl-1-{4-[5-(2-fluoro-biphenyl-4-yl)-[1,2,4]-oxadiazol-3-yl]-benzyl}-piperidine-4-carboxylic acid 1-{4-[5-(2-Fluoro-biphenyl-4-yl)-[1,2,4]-oxadiazol-3-yl]-benzyl}-4-(4-hydroxy-cyclohexylcarbamoyl)-piperidine-4-carboxylic acid 1-{4-[5-(2-Fluoro-biphenyl-4-yl)-[1,2,4]-oxadiazol-3-yl]-benzyl}-4-[(2-hydroxy-ethyl)-methyl-carbamoyl]-piperidine-4-carboxylic acid benzyl ester 4-Cyclohexylcarbamoyl-1-{4-[5-(2-fluoro-biphenyl-4-yl)-[1,2,4]-oxadiazol-3-yl]-benzyl}-piperidine-4-carboxylic acid benzyl ester 4-Dimethyl carbamoyl-1-{4-[5-(2-fluoro-biphenyl-4-yl)-[1,2,4]-oxadiazol-3-yl]-benzyl}-piperidine-4-carboxylic acid benzyl ester 4-[Bis-(2-hydroxy-ethyl)-carbamoyl]-1-{4-[5-(2-fluoro-biphenyl-4-yl)-[1,2,4]oxadiazol-3-yl]-benzyl}-piperidine-4-carboxylic acid benzyl ester 1-{4-[5-(2-Fluoro-biphenyl-4-yl)-[1,2,4]-oxadiazol-3-yl]-benzyl}-4-[(2-hydroxy-ethyl)-methyl-carbamoyl]-piperidine-4-carboxylic acid 1-{4-[5-(2-Fluoro-biphenyl-4-yl)-[1,2,4]-oxadiazol-3-yl]-benzyl}-4-(3-hydroxy-pyrrolidin-1-yl-carbonyl)-piperidine-4-carboxylic acid 1-{4-[5-(2-Fluoro-biphenyl-4-yl)-[1,2,4]-oxadiazol-3-yl]-benzyl}-4-{4-[2-(2-hydroxy-ethoxy)-ethyl]-piperazin-1-yl-carbonyl}-piperidine-4-carboxylic acid 4-[Bis-(2-hydroxy-ethyl)-carbamoyl]-1-{4-[5-(2-fluoro-biphenyl-4-yl)-[1,2,4]-oxadiazol-3-yl]-benzyl}-piperidine-4-carboxylic acid mono(isopropoxycarbonyloxy)methyl 1-{4-[5-(6-methoxynaphthalen-2-yl)-1,2,4-oxadiazol-3-yl]benzyl}piperidine-4,4-dicarboxylate monobenzyl 1-{4-[5-(2-fluorobiphenyl-4-yl)-1,2,4-oxadiazol-3-yl]benzyl}piperidine-3,3-dicarboxylate monoethyl 1-{4-[5-(2-fluorobiphenyl-4-yl)-1,2,4-oxadiazol-3-yl]benzyl}piperidine-3,3-dicarboxylate benzyl (isopropoxycarbonyloxy)methyl 1-{4-[5-(2-fluorobiphenyl-4-yl)-1,2,4-oxadiazol-3-yl]benzyl}piperidine-4,4-dicarboxylate benzyl 5-methyl-2-oxo-[1,3]dioxol-4-ylmethyl 1-{4-[5-(2-fluorobiphenyl-4-yl)-1,2,4-oxadiazol-3-yl]benzyl}piperidine-4,4-dicarboxylate (isopropoxycarbonyloxy)methyl methyl 1-{4-[5-(4-isobutylphenyl)-1,2,4-oxadiazol-3-yl]benzyl}piperidine-4,4-dicarboxylate mono-n-propyl 1-{4-[5-(2-fluorobiphenyl-4-yl)-1,2,4-oxadiazol-3-yl]benzyl}piperidine-4,4-dicarboxylate mono-n-butyl 1-{4-[5-(2-fluorobiphenyl-4-yl)-1,2,4-oxadiazol-3-yl]benzyl}piperidine-4,4-dicarboxylate diethyl 1-{4-[5-(2-fluorobiphenyl-4-yl)-1,2,4-oxadiazol-3-yl]benzyl}piperidine-4,4-dicarboxylate dibenzyl 1-{4-[5-(2-fluorobiphenyl-4-yl)-1,2,4-oxadiazol-3-yl]benzyl}piperidine-4,4-dicarboxylate 1-{4-[5-(2-Fluoro-biphenyl-4-yl)-[1,2,4]oxadiazol-3-yl]-benzyl}-4-(pyridin-2-ylcarbamoyl)-piperidine-4-carboxylic acid benzyl ester 4-Dimethylcarbamoyl-1-{4-[5-(2-fluoro-biphenyl-4-yl)-[1,2,4]oxadiazol-3-yl]-benzyl}-piperidine-4-carboxylic acid ethyl ester 4-Dimethylcarbamoyl-1-{4-[5-(2-fluoro-biphenyl-4-yl)-[1,2,4]oxadiazol-3-yl]-benzyl}-piperidine-4-carboxylic acid butyryloxymethyl ester 1-{4-[5-(2-Fluoro-biphenyl-4-yl)-[1,2,4]oxadiazol-3-yl]-benzyl}-4-(3-hydroxy-pyrrolidine-1-carbonyl)-piperidine-4-carboxylic acid acetoxymethyl ester 4-Dimethylcarbamoyl-1-{4-[5-(2-fluoro-biphenyl-4-yl)-[1,2,4]oxadiazol-3-yl]-benzyl}-piperidine-4-carboxylic acid isopropoxycarbonyloxymethyl ester 1-{4-[5-(2-Fluoro-biphenyl-4-yl)-[1,2,4]oxadiazol-3-yl]-benzyl}-4-(3-hydroxy-pyrrolidine-1-carbonyl)-piperidine-4-carboxylic acid isopropoxycarbonyloxymethyl ester 4-Dimethylcarbamoyl-1-{4-[5-(2-fluoro-biphenyl-4-yl)-[1,2,4]oxadiazol-3-yl]-benzyl}-piperidine-4-carboxylic acid 3,3-dimethyl-2-oxo-butyl ester 1-{4-[5-(2-Fluoro-biphenyl-4-yl)-[1,2,4]-oxadiazol-3-yl]-benzyl}-4-(pyridin-2-ylcarbamoyl)-piperidine-4-carboxylic acid 1-{4-[5-(2-Fluoro-biphenyl-4-yl)-[1,2,4]-oxadiazol-3-yl]-benzyl}-4-(pyridin-4-ylcarbamoyl)-piperidine-4-carboxylic acid 1-{4-[5-(2-Fluoro-biphenyl-4-yl)-[1,2,4]-oxadiazol-3-yl]-benzyl}-4-(3-hydroxy-pyrrolidine-1-carbonyl)-piperidine-4-carboxylic acid 3,3-dimethyl-2-oxo-butyl ester 4-Cyclohexylcarbamoyl-1-{4-[5-(2-fluoro-biphenyl-4-yl)-[1,2,4]oxadiazol-3-yl]-benzyl}-piperidine-4-carboxylic acid 3,3-dimethyl-2-oxo-butyl ester 4-(3-Benzyloxycarbonylamino-piperidine-1-carbonyl)-1-{4-[5-(2-fluoro-biphenyl-4-yl)-[1,2,4]oxadiazol-3-yl]-benzyl}-piperidine-4-carboxylic acid benzyl ester as well as their enantiomers, diastereomers, mixtures thereof and pharmaceutically acceptable salts, free forms, hydrates and solvates.

Preferred embodiments of the present invention provide a compound of formula (I) which possesses a selectivity for the S1P1 receptor over the S1P3 receptor of at least 10 fold, preferably 100 fold, more preferably 1000 fold as measured by the ratio of $EC_{50}$ at the S1P1 receptor to the $EC_{50}$ at the S1P3 receptor as evaluated in the $^{35}$S-GTP□S binding assay. Preferably said compound possesses an $EC_{50}$ for binding to the S1P1 receptor of 100 nM or less, more preferably 10 nM or less, still more preferably 5 nM or less as evaluated by the $^{35}$S-GTPγS binding assay in transfected cells expressing these receptors in high levels.

Highly preferred embodiment of the present invention possess an $EC_{50}$ for binding to the S1P1 receptor of 1 nM or less as evaluated by the $^{35}$S-GTPγS binding assay.

According to one aspect, the present invention also provides the process of preparation of the compound of formula (I).

The compounds and process of the present invention may be prepared in a number of ways well known to those skilled in the art. The compounds can be synthesized, for example, by application or adaptation of the methods described below, or variations thereon as appreciated by the skilled artisan. The appropriate modifications and substitutions will be readily apparent and well known or readily obtainable from the scientific literature to those skilled in the art.

In particular, such methods can be found in R. C. Larock, *Comprehensive Organic Transformations*, VCH publishers, 1989

It will be appreciated that the compounds of the present invention may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

Compounds of the present invention may be prepared by a variety of synthetic routes. The reagents and starting materials are commercially available, or readily synthesized by well-known techniques by one of ordinary skill in the arts. All substituents, unless otherwise indicated, are as previously defined.

In the reactions described hereinafter, it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in *Protective Groups in Organic Synthesis*, John Wiley and Sons, 1991; J. F. W. McOmie in *Protective Groups in Organic Chemistry*, Plenum Press, 1973.

Some reactions may be carried out in the presence of a base. There is no particular restriction on the nature of the base to be used in this reaction, and any base conventionally used in reactions of this type may equally be used here, provided that it has no adverse effect on other parts of the molecule. Examples of suitable bases include: sodium hydroxide, potassium carbonate, triethylamine, alkali metal hydrides, such as sodium hydride and potassium hydride; alkyllithium compounds, such as methyllithium and butyllithium; and alkali metal alkoxides, such as sodium methoxide and sodium ethoxide.

Usually, reactions are carried out in a suitable solvent. A variety of solvents may be used, provided that it has no adverse effect on the reaction or on the reagents involved. Examples of suitable solvents include: hydrocarbons, which may be aromatic, aliphatic or cycloaliphatic hydrocarbons, such as hexane, cyclohexane, benzene, toluene and xylene; amides, such as dimethyl-formamide; alcohols such as ethanol and methanol and ethers, such as diethyl ether and tetrahydrofuran.

The reactions can take place over a wide range of temperatures. In general, we find it convenient to carry out the reaction at a temperature of from 0° C. to 150° C. (more preferably from about room temperature to 100° C.). The time required for the reaction may also vary widely, depending on many factors, notably the reaction temperature and the nature of the reagents. However, provided that the reaction is effected under the preferred conditions outlined above, a period of from 3 hours to 20 hours will usually suffice.

The compound thus prepared may be recovered from the reaction mixture by conventional means. For example, the compounds may be recovered by distilling off the solvent from the reaction mixture or, if necessary after distilling off the solvent from the reaction mixture, pouring the residue into water followed by extraction with a water-immiscible organic solvent and distilling off the solvent from the extract. Additionally, the product can, if desired, be further purified by various well known techniques, such as recrystallization, reprecipitation or the various chromatography techniques, notably column chromatography or preparative thin layer chromatography.

According to one synthetic process, the compound of formula (I) where R7 is H and/or R8 is OH may be obtained from a corresponding compound of formula (I) wherein R7 and/or R8 represent(s) an ester function.

Preferably, a saponification is carried out, e.g. in the presence of a base, preferably a mineral base such as OH⁻, e.g. KOH or NaOH.

According to another synthetic process, said compound of formula (I) wherein $CO_2R7$ and/or COR8 represent(s) an ester function is obtained from a corresponding compound of formula (II):

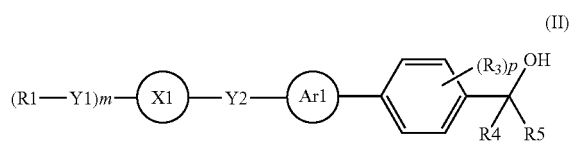

wherein R1, Y1, m, X1, Y2, Ar1, R3, R4, R5 and p are defined as in formula (I). Generally, this reaction is conducted by forming, as an intermediate, the mesylate derivative of (II), by reacting a suitable sulfonating reagent, such as methanesulfonyl chloride. The mesylate derivative is then coupled with a compound of formula (III):

where R6, Z, R7 and R8 are defined as in formula (I).

Generally, this reaction is carried out in the presence of a base, such as an organic base, preferably N,N-diisopropylethylamine, triethylamine or an inorganic base, preferably potassium, cesium or sodium carbonate or bicarbonate.

The reaction from (II) may be conducted as a one step reaction or may comprise the step of isolating the mesylate intermediate which is formed.

The above synthetic process may be illustrated by the scheme 1 below:

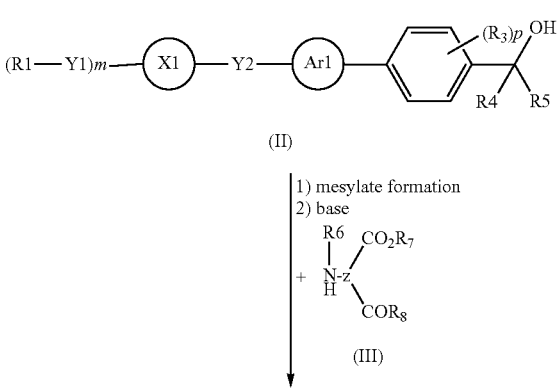

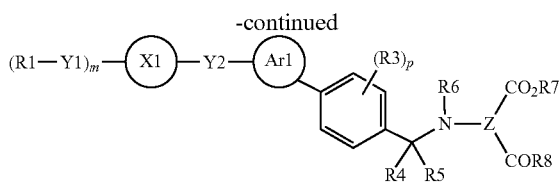

According to yet another synthetic process, the compound of formula (I), wherein $CO_2R7$ and/or COR8 represent(s) an ester function is obtained by reacting a corresponding compound of formula (IV):

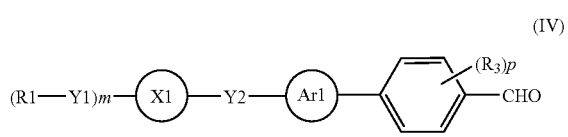

wherein R1, Y1, m, X1, Y2, Ar1, R3 and p are defined as in formula (I) with a compound of formula (III) as defined above. Generally, this reaction is conducted in the presence of a hydride or hydrogen. Preferred hydrides are triacetoxyborohydride and cyanoborohydride. When hydrogen is used, a catalyst is generally necessary, preferred catalysts are palladium, nickel and platinum. Hydrogen can also be replaced with hydrogen donnors, preferably formic acid, formic acid triethylamine eutectic mixture, cyclohexene or cyclohexadiene.

The obtained product may then be (partly) hydrolyzed as above.

According to another synthetic process, the compound of formula (I) may be obtained by reducing a corresponding compound of formula (V):

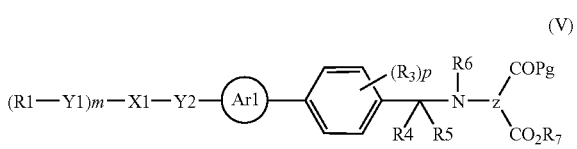

wherein R1, Y1, m, X1, Y2, Ar1, R3, R4, R5, p, R6, Z, R7 are defined as in formula (I) and Pg represents a protective group of the —COR8 group with R representing OH.

Generally, when Pg is a benzyl group or a substituted benzyl group, this reaction is carried out by hydrogenation or transfer hydrogenation, in the presence of Pd/C or nickel or platinum, this reaction can also be carried out with a Lewis acid such as aluminum trichloride and an electron rich aromatic such as anisole, when Pg is a trimethylsilylethyl, this reaction is carried out with fluoride ion, when Pg is a mono or polymethoxybenzyl group, this reaction is carried out with an oxidant such as cerium ammonium nitrate.

The compound of formula (V) may be obtained by reacting the corresponding compound of formula (VI):

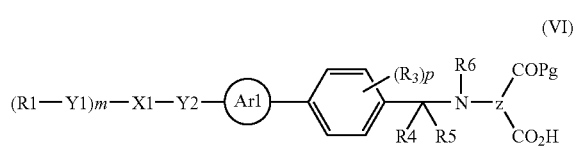

wherein R1, Y1, m, X1, Y2, Ar1, R3, R4, R5, p, R6, Z are defined as in formula (I) and Pg represents a protective group of the —COR8 function, with the compound of formula (VII):

where Hal represents a halogen atom and R7 is defined as in formula (I).

Generally, this reaction is carried out in the presence of an inorganic base such as sodium, potassium or cesium carbonate or bicarbonate or an organic base such as triethylamine, 1,5-diazabicyclo[4,3,0]non-5-ene or 1,8-diazabicyclo[5,4,0]undec-7-ene in a polar solvent such as N,N-dimethylacetamide or N,N-dimethylformamide.

The compound of formula (VI) may be obtained by saponifying the corresponding protected compound of formula (VIII):

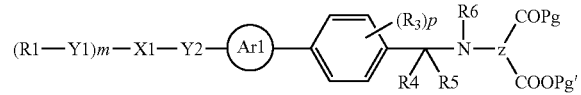

wherein R1, Y1, m, X1, Y2, Ar1, R3, R4, R5, p, R6, Z are defined as in formula (I), Pg represents a protective group of the —COR8 function and Pg' represents a protective group of the COOR7 function, by reacting a base, such as sodium or lithium hydroxide.

The compound of formula (VIII) may be obtained by coupling the corresponding of formula (IX)

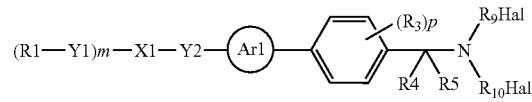

with the compound of formula (X):

where Hal represent a halogen atom and R9 and R10 are such that they form together with the N atom to which they are attached and carbon atom of (X) the desired ring formed by N, Z and R6.

Generally, this reaction is carried out in basic conditions with an inorganic base such as sodium, potassium or cesium carbonate in the presence of a phase transfer catalyst such as tetrabutylammonium bromide, triethylbenzylammonium chloride or aliquat.

The process of the invention may also include the additional step of isolating the obtained product of formula (I).

The starting products and/or reagents may be commercially available, or may be readily prepared by the skilled person by applying or adapting the procedures disclosed in the experimental part below.

According to a still further object, the present invention is also concerned with the use of a compound of formula (I) as defined above for the preparation of a medicament for decreasing circulating lymphocytes in blood in a human patient in the need thereof.

According to a preferred aspect, such medicament is suitable as immunosuppressive/depressive agent. More preferably, such medicament is particularly suitable for the treatment and/or prevention transplant rejection, tissue graft rejection, auto-immune diseases, inflammatory and chronic inflammatory conditions that include rheumatoid arthritis, asthma, pollinosis, psoriasis, myocarditis, atopic dermatitis, lymphocytic leukemias, lymphomas, multiple sclerosis, lupus erythematosus, inflammatory bowel diseases, diabetes mellitus, glomerulonephritis, atherosclerosis, multiorgan failure, sepsis, pneumonia, optic neuritis, polymyalgia rheumatica, uveitis, vasculitis, osteoarthritis, respiratory distress syndrome, ischemia reperfusion injury, chronic obstructive pulmonary disease, infection associated with inflammation, viral inflammation, influenza, hepatitis, Guillian-Barre syndrome, chronic bronchitis, restenosis, granulomatous disease, sarcoidosis, leprosy, scleroderma, Alzheimer's disease as well as disorders related to impaired vascular integrity, cancer, disregulated angiogenesis, excessive neoangiogenesis, in particular in cancer metastasis or other disorders.

Said disregulated angiogenesis or excessive neoangiogenesis is preferably selected from ocular angiogenic diseases selected from the group consisting of diabetic retinopathy, choroidal neovascularization, macular degeneration.

Said cancer is selected in particular from the group consisting of solid tumors, hematopoietic cancers and tumor metastases.

More preferably, said medicament is for treating and/or preventing tissue graft rejection.

According to a still further object, the present invention is also concerned with the use of a compound of formula (I) for the preparation of a medicament interacting with sphingosine phosphate receptor, preferably acting selectively as agonist of human S1P1 receptor, to be administered to a patient in the need thereof. Preferably, such medicament is substantially inactive at S1P3 receptors.

According to a still further object, the present invention also concerns the methods of treatment comprising administering an effective amount of a compound of the invention for treating and/or preventing the above conditions or disorders.

The present invention also provides methods for interacting with S1P receptors, preferably acting as agonist, preferably interacting selectively with S1P1 receptors, comprising administering an effective amount of a compound of the invention to a patient in the need thereof. Preferably, such methods are devoid of any substantial interaction with S1P3 receptors.

The identification of those subjects who are in need of treatment of herein-described diseases and conditions is well within the ability and knowledge of one skilled in the art. A clinician skilled in the art can readily identify, by the use of clinical tests, physical examination and medical/family history, those subjects who are in need of such treatment.

A therapeutically effective amount can be readily determined by the attending diagnostician, as one skilled in the art, by the use of conventional techniques and by observing results obtained under analogous circumstances. In determining the therapeutically effective amount, a number of factors are considered by the attending diagnostician, including, but not limited to: the species of subject; its size, age, and general health; the specific disease involved; the degree of involvement or the severity of the disease; the response of the individual subject; the particular compound administered; the mode of administration; the bioavailability characteristic of the preparation administered; the dose regimen selected; the use of concomitant medication; and other relevant circumstances.

The amount of a compound of formula (I), which is required to achieve the desired biological effect, will vary depending upon a number of factors, including the dosage of the drug to be administered, the chemical characteristics (e.g. hydrophobicity) of the compounds employed, the potency of the compounds, the type of disease, the diseased state of the patient, and the route of administration.

In general terms, the compounds of this invention may be provided in an aqueous physiological buffer solution containing 0.1 to 10% w/v compound for parenteral administration. Typical dose ranges are from 1 μg/kg to 0.1 g/kg of body weight per day; a preferred dose range is from 0.01 mg/kg to 10 mg/kg of body weight per day. A preferred daily dose for adult humans includes 1, 5, 50, 100 and 200 mg, and an equivalent dose in a human child. The preferred dosage of drug to be administered is likely to depend on such variables as the type and extent of progression of the disease or disorder, the overall health status of the particular patient, the relative biological efficacy of the compound selected, and formulation of the compound excipient, and its route of administration.

The compounds of the present invention are capable of being administered in unit dose forms, wherein the term "unit dose" means a single dose which is capable of being administered to a patient, and which can be readily handled and packaged, remaining as a physically and chemically stable unit dose comprising either the active compound itself, or as a pharmaceutically acceptable composition, as described hereinafter. As such, typical daily dose ranges are from 0.01 to 10 mg/kg of body weight. By way of general guidance, unit doses for humans range from 0.1 mg to 1000 mg per day. Preferably, the unit dose range is from 1 to 500 mg administered one to four times a day, and even more preferably from 1 mg to 300 mg, once a day. Compounds provided herein can be formulated into pharmaceutical compositions by admixture with one or more pharmaceutically acceptable excipients. Such compositions may be prepared for use in oral administration, particularly in the form of tablets or capsules; or parenteral administration, particularly in the form of liquid solutions, suspensions or emulsions; or intranasally, particularly in the form of powders, nasal drops, or aerosols; or dermally, for example, topically or via trans-dermal patches or ocular administration, or intravaginal or intra-uterine administration, particularly in the form of pessaries or by rectal administration.

The compositions may conveniently be administered in unit dosage form and may be prepared by any of the methods well known in the pharmaceutical art, for example, as described in Remington: *The Science and Practice of Pharmacy*, $20^{th}$ ed.; Gennaro, A. R., Ed.; Lippincott Williams & Wilkins: Philadelphia, Pa., 2000. Pharmaceutically compatible binding agents and/or adjuvant materials can be included as part of the composition. Oral compositions will generally include an inert diluent carrier or an edible carrier.

The tablets, pills, powders, capsules, troches and the like can contain one or more of any of the following ingredients, or compounds of a similar nature: a binder such as microcrystalline cellulose, or gum tragacanth; a diluent such as starch or lactose; a disintegrant such as starch and cellulose derivatives; a lubricant such as magnesium stearate; a glidant such as colloidal silicon dioxide; a sweetening agent such as sucrose or saccharin; or a flavoring agent such as peppermint, or methyl salicylate. Capsules can be in the form of a hard capsule or soft capsule, which are generally made from gelatin blends optionally blended with plasticizers, as well as a starch capsule. In addition, dosage unit forms can contain various other materials that modify the physical form of the dosage unit, for example, coatings of sugar, shellac, or enteric agents. Other oral dosage forms syrup or elixir may contain sweetening agents, preservatives, dyes, colorings, and flavorings. In addition, the active compounds may be incorporated into fast dissolve, modified-release or sustained-release preparations and formulations, and wherein such sustained-release formulations are preferably bi-modal.

Preferred formulations include pharmaceutical compositions in which a compound of the present invention is formulated for oral or parenteral administration, or more preferably those in which a compound of the present invention is formulated as a tablet. Preferred tablets contain lactose, cornstarch, magnesium silicate, croscarmellose sodium, povidone, magnesium stearate, or talc in any combination. It is also an aspect of the present disclosure that a compound of the present invention may be incorporated into a food product or a liquid.

Liquid preparations for administration include sterile aqueous or non-aqueous solutions, suspensions, and emulsions. The liquid compositions may also include binders, buffers, preservatives, chelating agents, sweetening, flavoring and coloring agents, and the like. Non-aqueous solvents include alcohols, propylene glycol, polyethylene glycol, acrylate copolymers, vegetable oils such as olive oil, and organic esters such as ethyl oleate. Aqueous carriers include mixtures of alcohols and water, hydrogels, buffered media, and saline. In particular, biocompatible, biodegradable lactide polymer, lactide/glycolide copolymer, or polyoxyethylene-polyoxypropylene copolymers may be useful excipients to control the release of the active compounds. Intravenous vehicles can include fluid and nutrient replenishers, electrolyte replenishers, such as those based on Ringer's dextrose, and the like. Other potentially useful parenteral delivery systems for these active compounds include ethylene-vinyl acetate copolymer particles, osmotic pumps, implantable infusion systems, and liposomes.

Alternative modes of administration include formulations for inhalation, which include such means as dry powder, aerosol, or drops. They may be aqueous solutions containing, for example, polyoxyethylene-9-lauryl ether, glycocholate and deoxycholate, or oily solutions for administration in the form of nasal drops, or as a gel to be applied intranasally. Formulations for buccal administration include, for example, lozenges or pastilles and may also include a flavored base, such as sucrose or acacia, and other excipients such as glycocholate. Formulations suitable for rectal administration are preferably presented as unit-dose suppositories, with a solid based carrier, such as cocoa butter, and may include a salicylate. Formulations for topical application to the skin preferably take the form of an ointment, cream, lotion, paste, gel, spray, aerosol, or oil. Carriers which can be used include petroleum jelly, lanolin, polyethylene glycols, alcohols, or their combinations. Formulations suitable for transdermal administration can be presented as discrete patches and can be lipophilic emulsions or buffered, aqueous solutions, dissolved and/or dispersed in a polymer or an adhesive.

Alternative administrations include also solutions, ointments or other formulations acceptable for ocular administration.

According to a particular aspect, the compound of the invention may be administered by the cutaneous, ocular or inhalation route as disclosed above. These formulations are particularly advantageous as they ensure a local treatment, without associated lymphopenia which may occur with systemic administration routes.

Other features of the invention will become apparent in the course of the following description of exemplary embodiments that are given for illustration of the invention and not intended to be limiting thereof.

Preparation of Intermediates

Preparation of 2-fluorobiphenyl-4-carboxylic acid

Scheme:

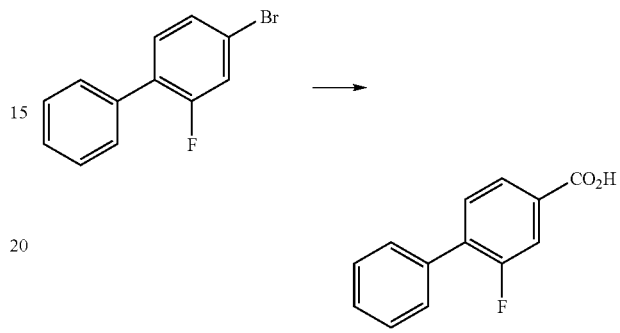

Few crystals of iodine are added to tetrahydrofuran (1400 mL) containing magnesium turnings (25.17 g, 1.035 mol). The mixture is heated at 60-70° C. A solution of 4-bromo-2-fluorobiphenyl (200 g, 0.797 mol) in tetrahydrofuran (600 mL) is added dropwise to the reaction mixture and refluxed for 1 hr. Reaction mixture is brought to room temperature and then cooled to −20° C. Carbon dioxide gas is passed through the reaction mixture for 45 minutes. The reaction mixture is treated with 3N HCl (500 mL) and extracted with ethyl acetate (2×500 mL). Combined organic layer is dried over sodium sulphate. Removal of solvent under reduced pressure gives a solid which is washed with diethyl ether (2×200 mL) and then dried to furnish 2-fluorobiphenyl-4-carboxylic acid.

Preparation of 4-(cyclopropylmethyl)benzoic acid

Step-I

Scheme

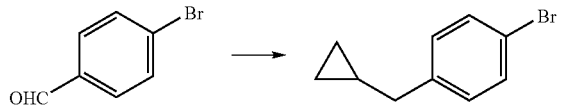

Solution of cyclopropyl magnesium bromide is prepared from cyclopropyl bromide (12 g, 0.099 mol) and magnesium turnings (3.0 g, 0.123 mol) in tetrahydrofuran (60 mL) by using standard Grignard reaction procedure. This reagent solution is cooled to 5° C. and a solution of 4-bromobenzaldehyde (15.0 g, 0.081 mol) in tetrahydrofuran (30 mL) is added to it over a period of 15 minute at 10-15° C. The reaction mixture is treated with aqueous ammonium chloride solution and extracted with ethyl acetate (50 mL). The organic layer is concentrated under reduced pressure and the residue is purified by column chromatography (silica gel 230-400 mesh) to give (4-bromophenyl)-cyclopropylmethanol.

(4-Bromophenyl)cyclopropylmethanol (15.0 g) is treated with triethylsilane (30 mL) and trifluoroacetic acid (30 mL) and stirred at room temperature overnight. The reaction mixture is concentrated under reduced pressure and the residue is purified by column chromatography (silica gel 230-400 mesh, ethyl acetate:n-hexane 3:97) to furnish 1-bromo-4-cyclopropylmethylbenzene.

Step-II

Scheme

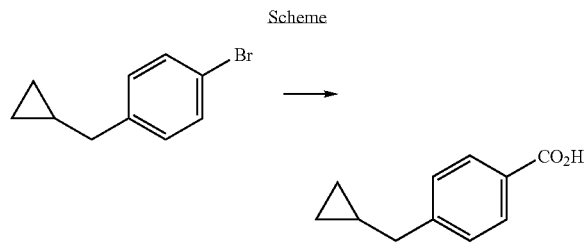

A solution of 1-bromo-4-cyclopropylmethylbenzene (10 g, 0.047 mol) in tetrahydrofuran (20 mL) is added to magnesium turnings (2.5 g, 0.1 mol) in tetrahydrofuran (20 mL) to generate the Grignard reagent which is cooled to 5° C. and N,N-dimethylformamide (8.0 g, 0.109 mol) is added to it. The reaction mixture is stirred at 10° C. for 1 hour. It is then treated with aqueous ammonium chloride solution and extracted with ethyl acetate (50 mL). The organic layer is concentrated under reduced pressure.

This residue is dissolved in tetrahydrofuran (240 mL), treated with chromic acid solution (25 mL) and stirred overnight at room temperature. It is extracted with ethyl acetate (50 mL). The organic layer is concentrated under reduced pressure. The residue is purified by usual acid-base treatment to furnish 4-(cyclopropylmethyl)benzoic acid.

Preparation of 4-isobutyrylbenzoic acid

Scheme

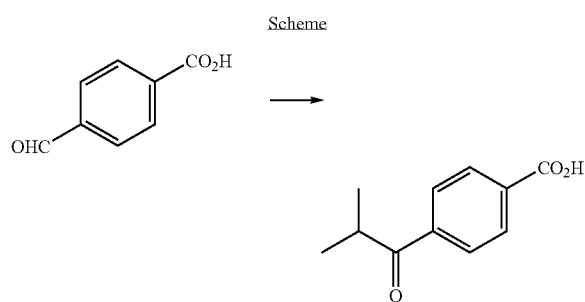

A solution of isopropylmagnesium bromide is prepared from isopropyl bromide (41.0 g, 0.33 mol) and magnesium turnings (10.0 g, 0.41 mol) in tetrahydrofuran (150 mL) by using standard Grignard reaction procedure. This solution is added to a solution of 4-formylbenzoic acid (5.0 g, 0.033 mol) in tetrahydrofuran (50 mL) at −20° C. over a period of 30 minutes. It is then stirred at −20° C. for 1 hour and then treated with aqueous ammonium chloride solution (150 mL). The organic layer is separated and concentrated under reduced pressure. This residue is dissolved in tetrahydrofuran (60 mL) and the solution is treated with an aqueous solution (8 mL) of sodium dichromate (1.5 g, 0.006 mol) and concentrated sulfuric acid (2 mL). The reaction mixture is stirred overnight at room temperature. It is then extracted with ethyl acetate (50 mL). The organic layer is dried and concentrated under reduced pressure. The residue is recrystallized from ethyl acetate:n-hexane mixture to give 4-isobutyrylbenzoic acid.

Preparation of 4'-fluorobiphenyl-4-carboxylic acid

Step I

Scheme:

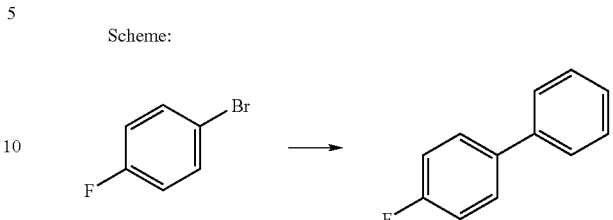

A solution of sodium carbonate (3.3 g, 0.031 mol) in demineralized water (25 mL) is added to a solution containing 4-fluorobromobenzene (4.55 g, 0.026 mol), phenylboronic acid (3.3 g, 0.027 mol), Pd (II) acetate (18 mg) and triphenylphosphine (65 mg) in n-propanol (50 mL). The reaction mixture is stirred at 80-90° C. for 1 hour. It is allowed to cool back to room temperature. Demineralized water (100 mL) is added and the aqueous layer is extracted with ethyl acetate (200 mL). The organic layer is concentrated and the residue is purified by column chromatography (silica gel 230-400 mesh, ethyl acetate:n-hexane 10:90) to furnish 4-fluorobiphenyl.

Step II

Scheme

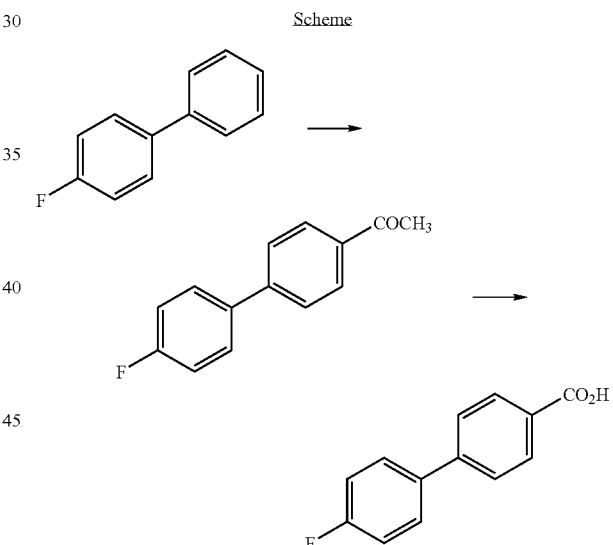

Anhydrous aluminum chloride (6.0 g, 0.045 mol) is added portionwise to a mixture of 4-fluorobiphenyl (4.0 g, 0.023 mol) and acetyl chloride (4.0 g, 0.051 mol) in dichloromethane (40 mL) at 5° C. The reaction mixture is stirred for 3 hours at room temperature, then quenched with demineralized water (20 mL) and dichloromethane. The organic layer is separated and concentrated under reduced pressure. Tetrahydrofuran (40 mL) is added to the residue. An aqueous solution (12 mL) of sodium hydroxide (4.0 g, 0.1 mol) followed by potassium permanganate (4.0 g, 0.025 mol) are added. The reaction mixture is stirred overnight at room temperature and filtered through celite bed. Filtrate is concentrated, Demineralized water (20 mL) is added to the residue and pH is brought to ~2 with 1N HCl. Aqueous layer is extracted with ethyl acetate (3×20 mL). Combined ethyl acetate layers are washed with brine (1×15 mL) and dried over sodium sulphate.

Removal of ethyl acetate gives crude material which is purified by column chromatography (silica gel 230-400 mesh, ethyl acetate:n-hexane) to give 4'-fluorobiphenyl-4-carboxylic acid.

Preparation of
2,2-dimethyl-2,3-dihydro-1-benzofuran-5-carboxylic acid

Step-I

Scheme

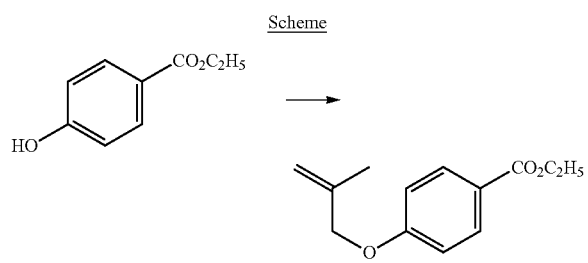

3-Chloro-2-methylpropene (2.1 mL, 0.021 mol) is added to a stirred N,N-dimethylformamide solution (30 mL) of ethyl 4-hydroxybenzoate (3 g, 0.018 mol). Potassium carbonate (3.2 g, 0.023 mol) is introduced and the mixture is heated at 90° C. for one hour. The reaction mixture is cooled to room temperature and filtered to remove inorganic salts. N,N-dimethylformamide is removed under reduced pressure, Demineralized water (20 mL) is added to the residue and the aqueous layer is extracted with ethyl acetate (3×20 mL). Combined organic layers are washed with demineralized water (2×15 mL) followed by brine and dried over sodium sulphate. Removal of ethyl acetate under reduced pressure gives a viscous liquid which is purified by column chromatography (silica gel 230-400 mesh, n-hexane:ethyl acetate, 90:10) to give 4-(2-methylprop-2-enyloxy)benzoic acid ethyl ester.

Step-II

Scheme:

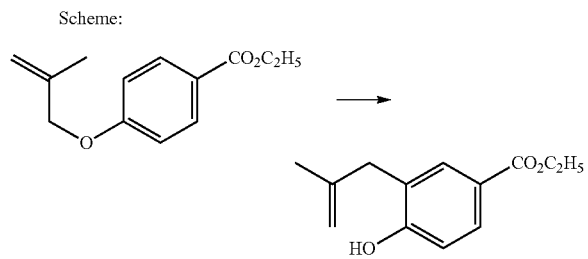

A mixture of 4-(2-methylprop-2-enyloxy)benzoic acid ethyl ester (15 g) and 1-methyl-2-pyrrolidinone (150 mL) is heated at reflux for nine hours. The reaction mixture is cooled to room temperature and made basic (pH ~10) by using aqueous sodium hydroxide solution. The aqueous layer is washed with toluene (2×20 mL) and then made acidic (pH ~2) with 2N HCl. The aqueous layer is extracted with ethyl acetate (3×20 mL). Combined organic layers are washed with brine (1×15 mL) and dried over sodium sulphate. Removal of solvent gives a dark brown liquid which is purified by column chromatography (silica gel 230-400 mesh, n-hexane:ethyl acetate, 80:20) to give 4-hydroxy-3-(2-methylprop-2-enyl)benzoic acid ethyl ester.

Step-III

Scheme

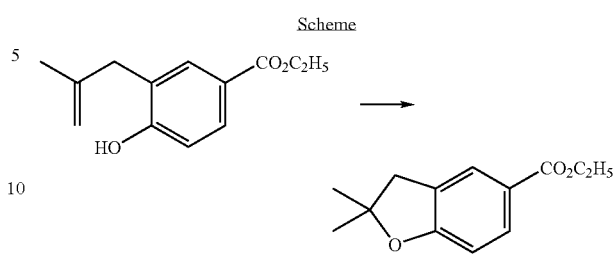

A mixture of formic acid (12 mL) and 4-hydroxy-3-(2-methylprop-2-enyl)benzoic acid ethyl ester (4.8 g, 0.022 mol) is heated at 110° C. for 15 minutes. The reaction mixture is cooled to room temperature and formic acid is removed under reduced pressure. Demineralized water is added to the residue and the aqueous layer is extracted with dichloromethane (3×15 mL). Combined organic layers are washed with demineralized water (1×15 mL) followed by brine (1×15 mL) and dried over sodium sulphate. Removal of solvent gives a viscous liquid which is purified by column chromatography (silica gel 230-400 mesh, n-hexane:ethyl acetate, 90:10) to give 2,2-dimethyl-2,3-dihydro-1-benzofuran-5-carboxylic acid ethyl ester.

Step-IV

Scheme

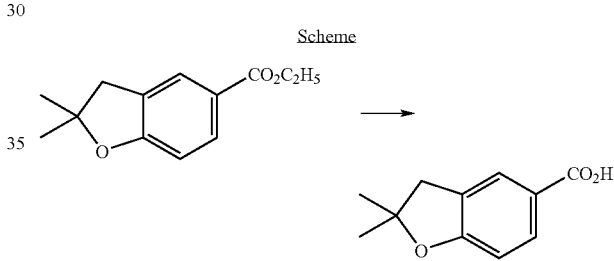

An aqueous solution (10 mL) of sodium hydroxide (0.78 g, 0.0195 mol) is added to an ethanolic solution (30 mL) of 2,2-dimethyl-2,3-dihydrobenzofuran-5-carboxylic acid ethyl ester (3.9 g, 0.018 mol). The reaction mixture is heated at 75° C. for four and an half hours. Ethanol is removed under reduced pressure. Demineralized water is added to the residue and pH is brought to ~3 with 1 N HCl. Solid thus obtained is filtered, washed with demineralized water and dried under reduced pressure to give 2,2-dimethyl-2,3-dihydrobenzofuran-5-carboxylic acid.

Preparation of
1,1-dimethyl-1,3-dihydro-2-benzofuran-5-carboxylic acid

Step-I & Step-II

Scheme:

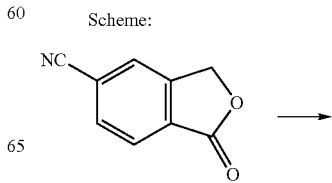

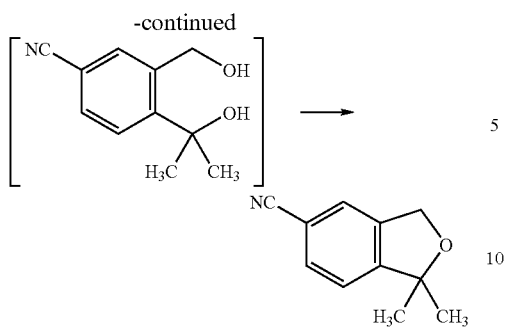

5-Cyano-1-oxo-2-benzofuran (75.0 g, 0.47 mol) is added to in situ prepared Grignard solution of methylmagnesium iodide (470.5 g, 2.83 mol) in tetrahydrofuran at −30° C. and stirred for one hour at −30° C. The reaction mixture is quenched with ammonium chloride solution and aqueous layer is extracted with ethyl acetate. Combined organic layers are washed with demineralized water (1×40 mL) followed by brine (1×30 mL) and finally dried over sodium sulphate. Removal of ethyl acetate under reduced pressure gives a viscous liquid which is purified by column chromatography (silica gel 230-400 mesh, n-hexane:ethyl acetate, 80:20) to give 3-hydroxymethyl-4-(1-hydroxy-1-methylethyl)benzonitrile.

A mixture of orthophosphoric acid (147.5 mL) and demineralized water (29.5 mL) is added to a stirred toluene solution (300 mL) of 3-hydroxymethyl-4-(1-hydroxy-1-methylethyl)benzonitrile (29.5 g, 0.154 mol) at 0-5° C. The reaction mixture is stirred at room temperature for 3.0 hrs. The toluene layer is separated and the aqueous layer is extracted with toluene (3×50 mL). Combined organic layers are washed with saturated sodium bicarbonate solution (1×40 mL) followed by demineralized water (1×40 mL). Evaporation of the toluene layer under reduced pressure gives a viscous liquid which is purified by column chromatography (silica gel 230-400 mesh,) to give 1,1-dimethyl-1,3-dihydro-2-benzofuran-5-carbonitrile.

Step-III

Scheme:

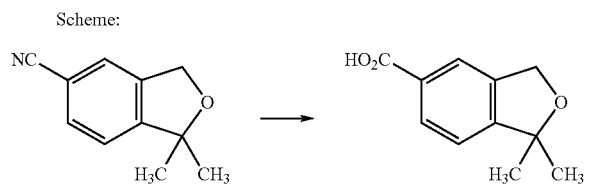

An aqueous solution (15 mL) of sodium hydroxide (0.09 mol) is added to a stirred ethanolic solution (10 mL) of 1,1-dimethyl-1,3-dihydro-2-benzofuran-5-carbonitrile (1.5 g, 0.0087 mol). The reaction mixture is heated at 85° C. for one and an half hour. Ethanol is removed under reduced pressure. Demineralized water (15 mL) is added to the residue and the aqueous layer is washed with ethyl acetate. The aqueous layer is made acidic (pH ~3) by using 1N HCl and extracted with ethyl acetate (3×15 mL). Combined organic layers are washed with demineralized water (1×10 mL) followed by brine (1×10 mL) and finally dried over sodium sulphate. Removal of ethyl acetate gives 1,1-dimethyl-1,3-dihydro-2-benzofuran-5-carboxylic acid.

General method of preparation of 4-(3-substituted-1,2,4-oxadiazol-5-yl)phenylmethanol derivatives Preparation of 4-[3-(2-fluorobiphenyl-4-yl)-1,2,4-oxadiazol-5-yl]phenylmethanol Step I Scheme

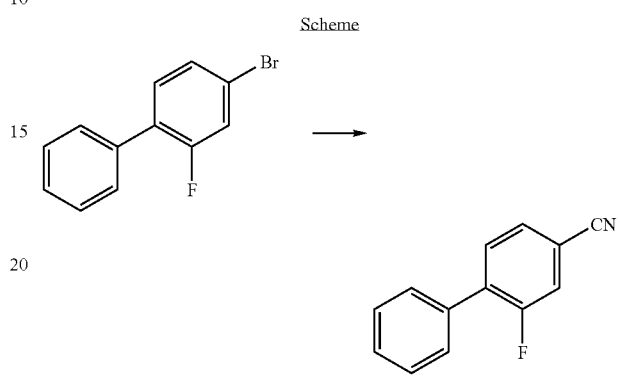

Copper (I) cyanide (10.69 g, 0.12 mol) and potassium iodide (6.21 g, 0.037 mol) are added to a stirred pyridine solution (10 mL) of 4-bromo-2-fluorobiphenyl (10 g, 0.040 mol). The reaction mixture is heated at 150-152° C., 5 mL pyridine is distilled out and heating is continued at 150-152° C. for 24 hrs. The reaction mixture is cooled to 95-1000, toluene (100 mL) is added to it. It is cooled to 35-40° C. and an aqueous ammonia solution (25%, 100 mL) is added. After stirring for half an hour, toluene layer is separated and washed with aqueous ammonia solution (2×50 mL), then demineralized water (3×100 mL). The toluene layer is charcoalized and concentrated to give 2-fluorobiphenyl-4-carbonitrile.

Step II

Scheme

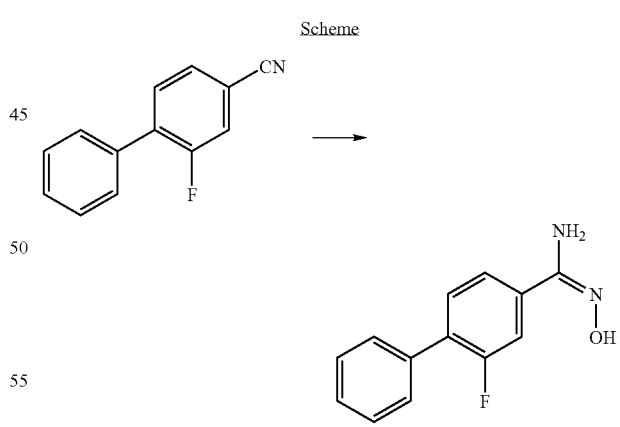

A solution of 2-fluorobiphenyl-4-carbonitrile (1.97 g, 0.01 mol), hydroxylamine hydrochloride (2.09 g, 0.03 mol) and sodium hydrogen carbonate (4.2 g, 0.05 mol) in methanol (50 mL) is heated to reflux for 7 hrs. The reaction mixture is then cooled to room temperature and filtered. The solid is washed with methanol (20 mL). The combined methanol solution is concentrated to dryness to get 2-fluoro-N-hydroxybiphenyl-4-carboxamidine which is used as such for the next step without further purification.

Step III

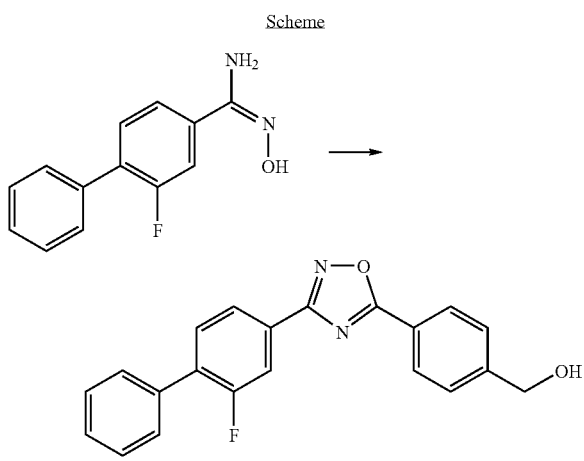

1-Hydroxybenzotriazole hydrate (1.35 g, 0.01 mol) and 1-(3-dimethylaminopropyl)-3-ethylcarbodiimide HCl (1.95 g, 0.01 mol) are added to a stirred N,N-dimethylformamide solution (20 mL) of 4-hydroxymethylbenzoic acid (1.52 g, 0.01 mol). 2-Fluoro-N-hydroxybiphenyl-4-carboxamidine (2.3 g, 0.01 mol) is added to the reaction mixture which is then heated at 130-140° C. for 4 hrs. The reaction mixture is cooled to room temperature, Demineralized water (60 mL) is added and the aqueous layer is extracted with ethyl acetate (3×20 mL). Combined organic layers are washed with demineralized water (2×10 mL) followed by brine (1×20 mL) and finally dried over sodium sulphate. Removal of ethyl acetate under reduced pressure gives a crude liquid which is purified by column chromatography (silica gel 230-400 mesh, ethyl acetate:n-hexane 30:70) to furnish {4-[3-(2-fluorobiphenyl-4-yl)-1,2,4-oxadiazol-5-yl]phenyl}methanol.

General method of preparation of 4-(5-substituted-1,2,4-oxadiazol-3-yl)phenylmethanol derivatives Preparation of 4-[5-(4-trifluoromethylphenyl)-1,2,4-oxadiazol-3-yl]phenylmethanol

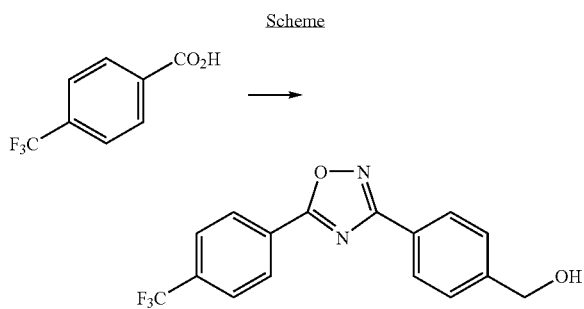

A mixture of 4-trifluoromethylbenzoic acid (6 g, 0.032 mol), 1-(3-dimethylaminopropyl)-3-ethyl-carbodiimide (6.05 g, 0.0315 mol) and 1-hydroxy-benzotriazole hydrate (4.82 g, 0.032 mol) in N,N-dimethylformamide (30 mL) is stirred at room temperature for 30 minutes. N-Hydroxy-4-hydroxymethylbenzamidine (6.97 g, 90%, 0.038 mol) is added and the reaction mixture is heated at reflux for 3 hrs, then allowed to come to room temperature and solvent is removed under reduced pressure. An aqueous solution (100 mL) of sodium bicarbonate is added to the residue and the aqueous layer is extracted with ethyl acetate (2×100 mL). Combined organic layers are dried over anhydrous sodium sulphate and concentrated under reduced pressure. The residue is purified by column chromatography (silica gel 230-400 mesh, n-hexane:ethyl acetate, 65:35) to give 4-[5-(4-trifluoromethylphenyl)-1,2,4-oxadiazol-3-yl]phenylmethanol.

Preparation of (Z)-4-[5-(furan-2-yl)methoxyiminomethyl-1,2,4-oxadiazol-3-yl]benzaldehyde Step-I (Z)-Furan-2-yl-[3-(4-hydroxymethyl phenyl)-1,2,4-oxadiazol-5-yl]methanone-O-methyl oxime is prepared by following the same general method as described earlier using (furan-2-yl)methoxyiminoacetic acid and N-hydroxy-4-hydroxy-methylbenzamidine.

Step-II

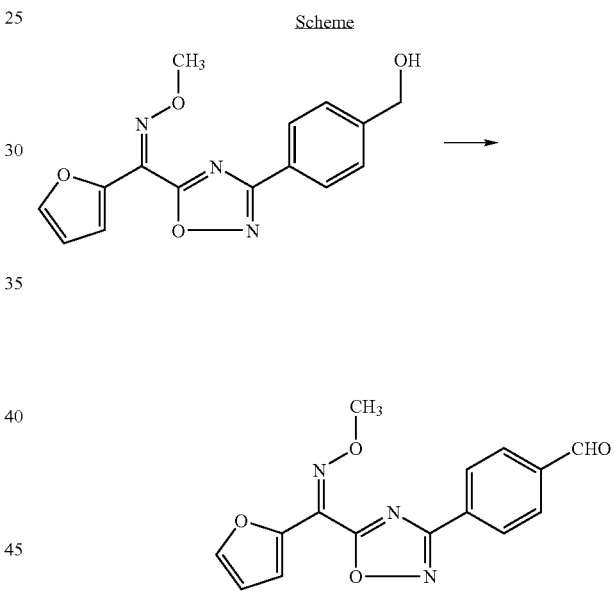

Dimethyl sulfoxide (1.1 g, 0.014 mol) is added to a solution of oxalyl chloride (1.0 g, 0.0079 mol) in dichloromethane (10 mL) at −78° C. over a period of 15 minutes. A solution of (Z)-furan-2-yl-[3-(4-hydroxymethylphenyl)-1,2,4-oxadiazol-5-yl]methanone-O-methyl oxime (1.0 g, 0.003 mol) in dichloromethane (10 mL) is added to the reaction mixture at −78° C. over a period of 15 minutes followed by the addition of N,N-diisopropylethylamine (3 mL). The reaction mixture is allowed to come to room temperature over a period of 1 to 2 hrs. The reaction mixture is then treated with a saturated aqueous solution (5 mL) of ammonium chloride. Dichloromethane layer is separated and concentrated under reduced pressure to give the product, which is purified by column chromatography (silica gel 230-400 mesh, n-hexane:ethyl acetate, 70:30) to furnish (Z)-4-[5-(furan-3-yl)methoxy-iminomethyl)-1,2,4-oxadiazol-3-yl]benzaldehyde.

Preparation of piperidine-4,4-dicarboxylic acid diethyl ester

Step I

Scheme

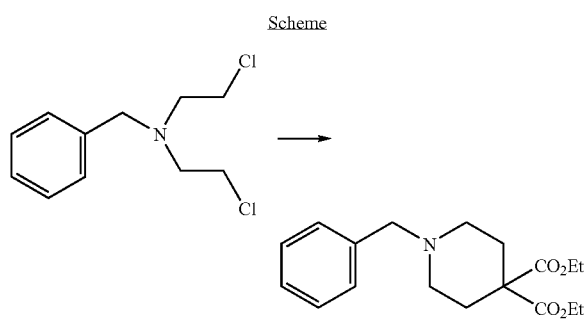

Potassium carbonate (79.22 g, 0.572 mol) and tetrabutylammonium bromide (6.16 g, 0.019 mol) are added to a solution of benzyl-bis-(2-chloroethyl)amine (47.5 g, 0.205 mol) and diethyl malonate (30.62 g, 0.191 mol) in N,N-dimethylformamide (450 mL). The reaction mixture is heated at 80° C. for 1.5 hours and then concentrated under reduced pressure. The residue is treated with demineralized water (200 mL) and the aqueous layer is extracted with ethyl acetate (3×100 mL). Combined organic layers are washed with brine (1×40 mL) and dried over sodium sulphate. Removal of solvent gives a viscous liquid which is purified by column chromatography (silica gel 230-400 mesh, n-hexane:ethyl acetate 80:20) to give 1-benzylpiperidine-4,4-dicarboxylic acid diethyl ester.

Step II

Scheme

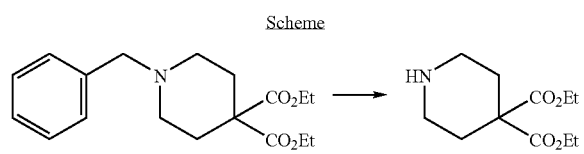 [SMILES: CCOC(=O)C1(C(=O)OCC)CCN(Cc2ccccc2)CC1 ; CCOC(=O)C1(C(=O)OCC)CCNCC1]

To a solution of benzylpiperidine-4,4-dicarboxylic acid diethyl ester (21.5 g, 0.067 mol) in ethanol (300 mL) is added 5% Pd/C (25 g, 50% wet). The reaction mixture is stirred under 40 psi pressure of hydrogen for 3 hrs, then filtered through a celite bed and the filtrate is concentrated to give a crude viscous liquid which is purified by column chromatography (silica gel 230-400 mesh, methanol:dichloromethane 10:90) to furnish piperidine-4,4-dicarboxylic acid diethyl ester as pale yellow liquid.

Alternative Method of Preparation of piperidine-4,4-dicarboxylic acid diethyl ester Step I Scheme

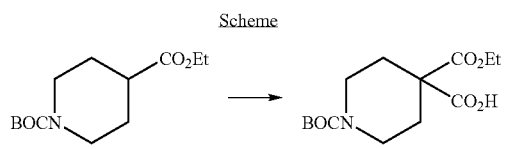

Lithium diisopropylamide (6.5 mL 25% solution in tetrahydrofuran, 0.013 mol) is added to a solution of N,N,N',N'-tetramethylethylenediamine (4.5 mL, 0.030 mol) and piperidine-1,4-dicarboxylic acid 1-tert-butyl 4-ethyl ester (3 g, 0.0117 mol) in dry tetrahydrofuran (40 mL) at −70° C. After stirring for 30 minutes the temperature is raised to −40° C. The reaction mixture is again cooled to −70° C. and carbon dioxide gas is bubbled through it. The reaction mixture is slowly allowed to come to 0° C. and is treated with a saturated aqueous ammonium chloride solution (10 mL). The organic layer is separated and concentrated. The residue is treated with an aqueous sodium hydrogen carbonate solution (20 mL). The aqueous layer is washed with n-hexane (2×10 mL), then acidified to pH ~5 with 2N HCl and extracted with ethyl acetate (2×20 mL). Combined organic layers are dried over anhydrous sodium sulphate and concentrated to give piperidine-1,4,4-tricarboxylic acid 1-tert-butyl 4-ethyl ester.

Step II

Scheme

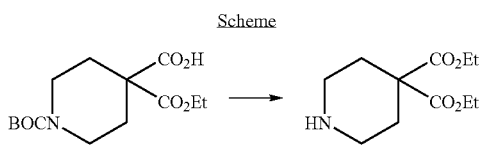

Ethanolic HCl (40 mL) is added to piperidine-1,4,4-tricarboxylic acid 1-tert-butyl 4-ethyl ester (2.35 g, 0.0078 mol) and the reaction mixture is heated under reflux for 5 hrs. The reaction mixture is concentrated under reduced pressure to give piperidine-4,4-dicarboxylic acid diethyl ester as hydrochloride salt.

Preparation of Dicarboxylic Acids

Method-A

Preparation of 1-{4-[5-(4-trifluoromethylphenyl)-1,2,4-oxadiazol-3-yl]benzyl}piperidine-4,4-dicarboxylic acid Step-I Scheme

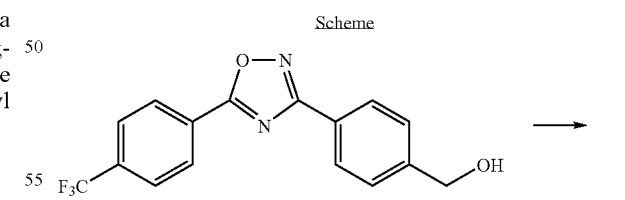

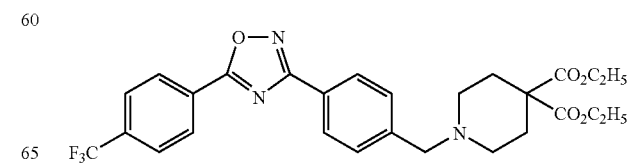

Methanesulfonyl chloride (1.07 g, 0.009 mol) is added a stirred solution of 4-[5-(4-trifluoromethylphenyl)-1,2,4-oxadiazol-3-yl]phenylmethanol (2 g, 0.0062 mol) and triethylamine (1.25 g, 0.0124 mol) in dichloromethane (30 mL) at 0-5° C. The reaction mixture is stirred at 10° C. for 20 minutes, then treated with demineralized water (10 mL). The dichloromethane layer is separated and the aqueous layer is extracted with dichloromethane (2×15 mL). Combined organic layers are dried over sodium sulphate and concentrated to furnish the crude mesylated product.

To a stirred solution of this mesylate in N,N-dimethylformamide (20 mL), N,N-diisopropylethylamine (1.2 g, 0.009 mol) and piperidine-4,4-dicarboxylic acid diethyl ester (1.7 g, 0.007 mol) are added. The reaction mixture is heated at 80° C. for 1 hour and then concentrated under reduced pressure. Demineralized water (15 mL) is added to the residue and the aqueous layer is extracted with ethyl acetate (2×30 mL). Combined organic layers are concentrated under reduced pressure and the residue is purified by column chromatography (silica gel 230-400 mesh, n-hexane:ethyl acetate 75:25) to furnish 1-{4-[5-(4-trifluoromethylphenyl)-1,2,4-oxadiazol-3-yl]benzyl}piperidine-4,4-dicarboxylic acid diethyl ester.

Step-II

Scheme

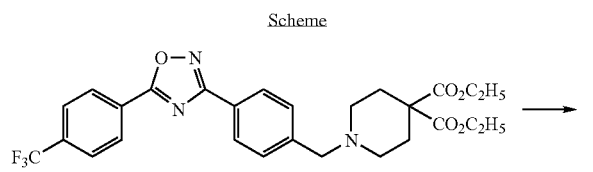

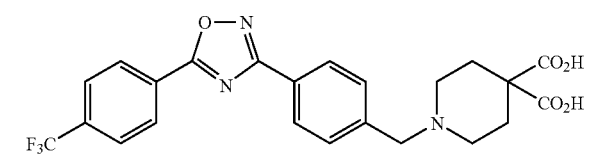

An aqueous solution (10 mL) of sodium hydroxide (0.86 g, 0.0215 mol) is added to a stirred solution of 1-{4-[5-(4-trifluoromethylphenyl)-1,2,4-oxadiazol-3-yl]benzyl}piperidine-4,4-dicarboxylic acid diethyl ester (2.3 g, 0.004 mol) in a mixture of ethanol (50 mL) and tetrahydrofuran (10 mL). The reaction mixture is refluxed for 20 hrs, then is concentrated under reduced pressure. The residue is acidified with 3N HCl to pH ~2. The solid thus formed is filtered, washed with a mixture of methanol:ether (30 mL, 10:90), then tetrahydrofuran (20 mL) and dried to furnish 1-{4-[5-(4-trifluoromethylphenyl)-1,2,4-oxadiazol-3-yl]benzyl}-piperidine-4,4-dicarboxylic acid (e.g. 14).

Method-B

Preparation of 1-{4-[5-(furan-2-yl)methoxyiminomethyl-1,2,4-oxadiazol-3-yl]benzyl}piperidine-4,4-dicarboxylic acid diethyl ester Step-I Scheme

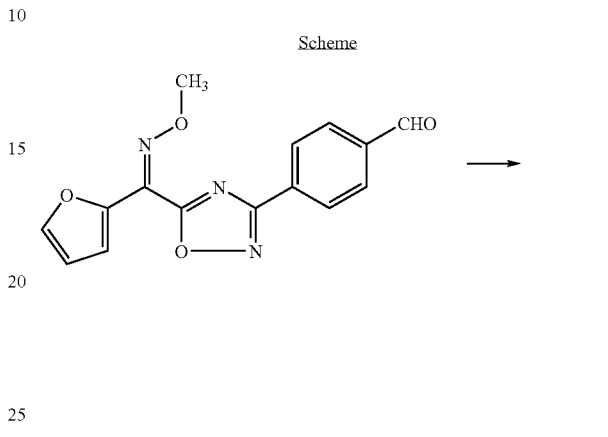

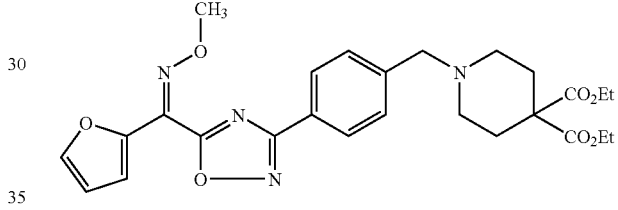

(Z)-4-[5-(Furan-2-yl)methoxyiminomethyl]-1,2,4-oxadiazol-3-yl]benzaldehyde (0.7 g, 0.0023 mol) is added to a solution of diethyl piperidine-4,4-dicarboxylate (0.5 g, 0.002 mol) in a mixture of acetic acid (1 mL) and methanol (30 mL). The reaction mixture is stirred at room temperature for 1 hour. A solution of sodium cyanoborohydride (0.1 g, 0.0016 mol) in methanol (10 mL) is added to the reaction mixture portion wise over a period of 30 minutes at room temperature and stirred overnight at room temperature. The reaction mixture is concentrated under reduced pressure, the residue is treated with ammonium hydroxide (3 mL) and extracted with dichloromethane (50 mL). The organic layer is concentrated and the residue is dissolved in a tetrahydrofuran (5 mL) and ethanol (10 mL) mixture. An aqueous solution (10 mL) of sodium hydroxide (1.0 g, 0.025 mol) is added to the mixture and allowed to stir overnight at room temperature. It is then concentrated under reduced pressure. The residue is acidified with 3N HCl to pH ~2 to give an off white solid which is filtered, washed with ethyl acetate (3×5 mL) and dried to furnish (Z)-1-{4-[5-(furan-2-yl)methoxyiminomethyl-1,2,4-oxadiazol-3-yl]benzyl}-piperidine-4,4-dicarboxylic acid diethyl ester.

This diethyl ester derivative is hydrolysed to the corresponding diacid as described in the previous procedure (e.g. 22).

Partial hydrolysis of diesters can be performed to result in the formation of mono acid esters (e.g. 52).

Examples 1-37 are prepared either by method A or by method B.

Compound
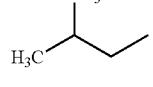
| Ex. | R | R₁ | R₂ | R₃ | R₄ | R₅ | R₆ | MS(ESI⁺) |
|---|---|---|---|---|---|---|---|---|
| 1 | 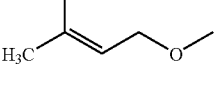 | H | H | H | H | OH | OH | 464.1 |
| 2 |  | H | H | H | H | OH | OH | 492.22 |
| 3 | Ph | F | H | H | H | OH | OH | 502.19 |
| 4 | Ph | F | H | H | H | OH | OMe | 516.17 |
| 5 | 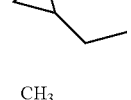 | H | H | H | H | OH | OH | 462.07 |
| 6 | 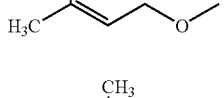 | H | H | H | H | OH | OMe | 476.19 |
| 7 | 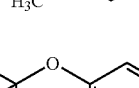 | H | H | H | H | OH | OMe | 506.21 |
| 8 | 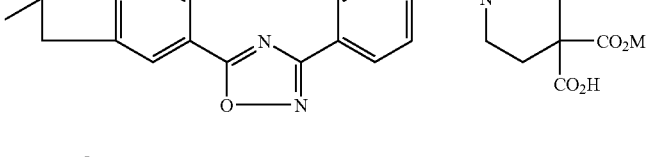 | H | H | H | H | OH | OMe | 478.2 |
| 9 | 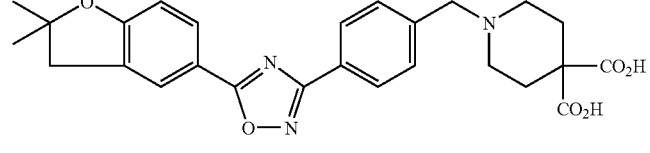 | | | | | | | 492.0 |
| 10 | 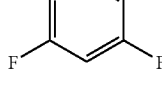 | | | | | | | 478.1 |
| 11 | 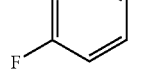 | H | H | H | H | OH | OH | 520.1 |
| 12 |  | H | H | H | H | OH | OH | 502.1 |

-continued
Compound
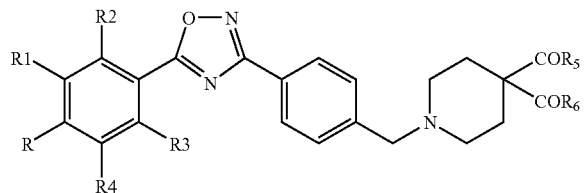
| Ex. | R | R₁ | R₂ | R₃ | R₄ | R₅ | R₆ | MS(ESI⁺) |
|---|---|---|---|---|---|---|---|---|
| 13 | 3,5-difluorophenyl | H | H | H | H | OH | OH | 520.1 |
| 14 | CF₃ | H | H | H | H | OH | OH | 476.1 |
| 15 | Ph | H | H | H | H | OH | OH | 484.1 |
| 16 | F₃CO | H | H | H | H | OH | OH | 492.0 |
| 17 | H | F | F | H | H | OH | OH | |
| 18 | H₃CO₂S | H | H | H | H | OH | OH | 486.1 |
| 19 | 4-(4-chlorophenyl)cyclohexyl substituent | | | | | | | 524.1 |
| 20 | 3,3-dimethyl-1,3-dihydroisobenzofuran-5-yl substituent | | | | | | | 478.1 |
| 21 | F₃C-CH₂-O-CH₂- | H | H | H | H | OH | OH | 506.1 |
| 22 | furan-2-yl(methoxyimino)methyl substituent | | | | | | | 455.1 |
| 23 | Bn | H | H | H | H | OH | OH | 498.1 |
| 24 | 4-isopropylcyclohexyl substituent | | | | | | | 456.2 |

-continued

Compound

[Structure: phenyl ring with R1–R4 substituents, connected to 1,2,4-oxadiazole, linked to phenyl-CH2-N-piperidine bearing COR5 and COR6 groups]

| Ex. | R | R₁ | R₂ | R₃ | R₄ | R₅ | R₆ | MS(ESI⁺) |
|---|---|---|---|---|---|---|---|---|
| 25 | [4-isopropenylcyclohexyl-oxadiazole-phenyl-CH2-piperidine-(CO2H)2 structure] | | | | | | | 452.1 |
| 26 | [dimethyl-dihydroisobenzofuran-oxadiazole-phenyl-CH2-piperidine-(CO2H)2 structure] | | | | | | | 478.1 |
| 27 | [2-fluorobiphenyl-oxadiazole-phenyl-CH2-piperidine-(CO2H)2 structure] | | | | | | | 500.2 (M⁻) |
| 28 | [pinene-CH2-oxadiazole-phenyl-CH2-piperidine-(CO2H)2 structure] | | | | | | | 466.1 |
| 29 | [PhC(O)-] | H | H | H | H | OH | OH | 512.1 |
| 30 | [6-methoxynaphthyl-oxadiazole-phenyl-CH2-piperidine-(CO2H)2 structure] | | | | | | | 485.99 (M⁻) |
| 31 | Bn | F | F | H | H | OH | OH | 534.1 |
| 32 | [(CH3)2CH-C(O)-] | H | H | H | H | OH | OH | 478.2 |

Compound

| Ex. | R | R1 | R2 | R3 | R4 | R5 | R6 | MS(ESI+) |
|---|---|---|---|---|---|---|---|---|
| 33 | 2,3-difluoro-ethylphenyl (F, F, ethyl) | H | H | H | H | OH | OH | 534.1 |
| 34 | H5C2O | H | H | H | H | OH | OH | 452.19 |
| 35 | (CH3)3C | H | H | H | H | OH | OH | 464.22 |
| 36 | (CH3)2CH-O-CH3 (isopropoxymethyl) | H | H | H | H | OH | OH | 463.99 (M⁻) |
| 37 | cyclohexyl | H | H | H | H | OH | OH | 490.1 |

M⁻, ESI negative ion mode.

Preparation of Dicarboxylic Acid Ester Derivatives

Preparation of 1-{4-[5-(2-fluorobiphenyl-4-yl)-1,2,4-oxadiazol-3-yl]benzyl}piperidine-4,4-dicarboxylic acid mono (2,2-dimethylpropionyl-oxymethyl)ester Step-I

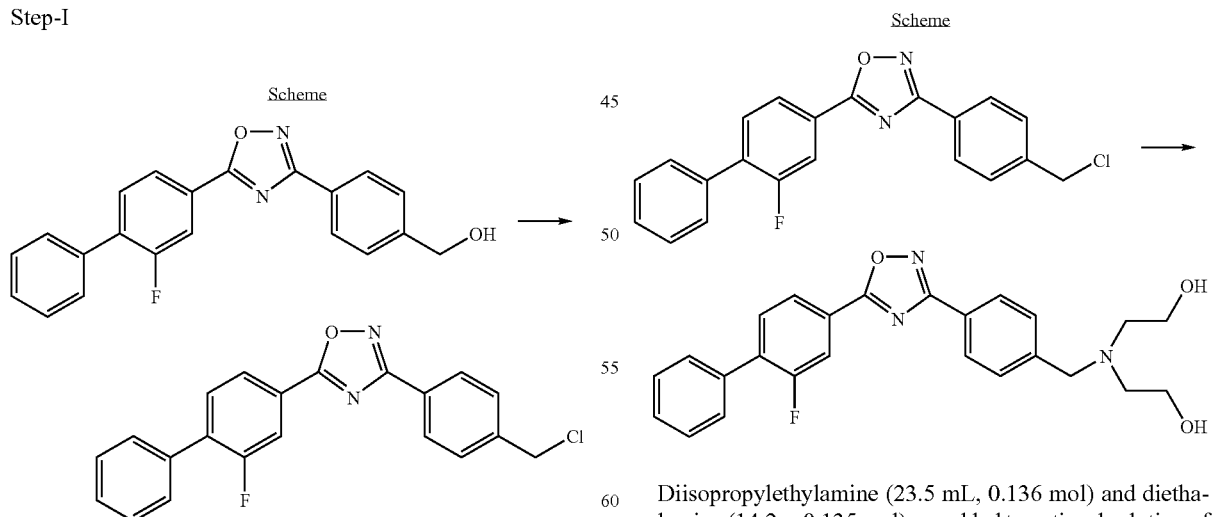

Thionyl chloride (20 mL, 0.274 mol) and N,N-dimethyl-formamide (2 mL) are added to a stirred solution of 4-[5-(2-fluorobiphenyl-4-yl)-1,2,4-oxadiazole-3-yl]phenylmethanol (32 g, 0.092 mol) in dichloromethane (150 mL) at 0° C. The reaction mixture is heated at 80° C. for 1 hour and then concentrated under reduced pressure. The residue is neutralized with a saturated aqueous sodium bicarbonate solution (150 mL) to furnish a solid which is filtered and washed with n-hexane (150 mL) to give 3-(4-chloromethylphenyl)-5-(2-fluorobiphenyl-4-yl)-1,2,4-oxadiazole.

Step-II

Diisopropylethylamine (23.5 mL, 0.136 mol) and diethanolamine (14.2 g, 0.135 mol) are added to a stirred solution of 3-(4-chloromethylphenyl)-5-(2-fluorobiphenyl-4-yl)-1,2,4-oxadiazole (33 g, 0.090 mol) in N,N-dimethyl-formamide (200 mL). The reaction mixture is heated at 90° C. for 2.5 hrs, the solvent is removed under reduced pressure and the residue is treated with demineralized water (200 mL) to get a solid which is filtered and washed with n-hexane (150 mL) and diethyl ether (100 mL) to furnish 2-[{4-[5-(2-fluorobiphenyl-4-yl)-1,2,4-oxadiazole-3-yl]benzyl}(2-hydroxyethyl)amino]ethanol.

Step-III

Scheme

Step-IV

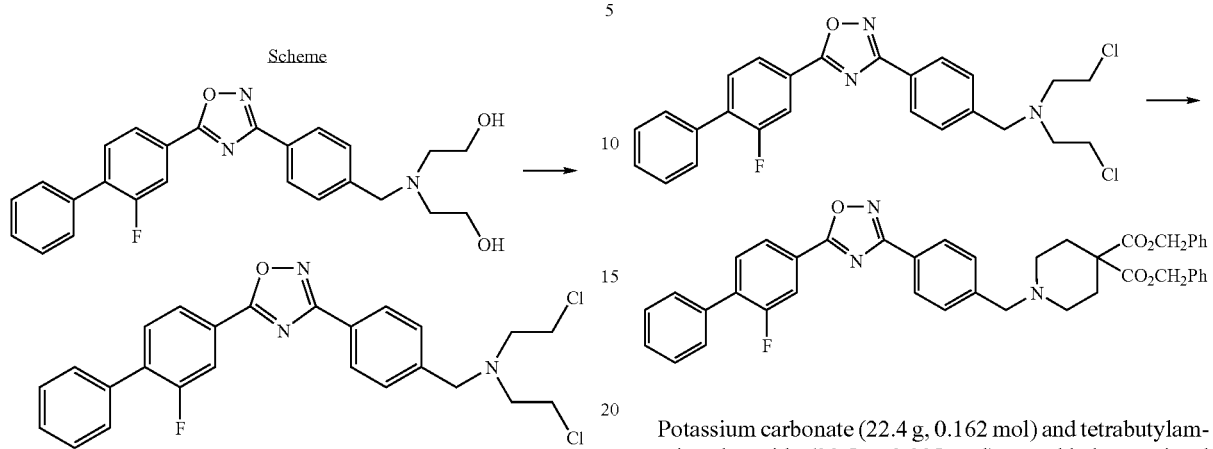

Thionyl chloride (52 mL, 0.716 mol) is added drop wise to a stirred solution of 2-[{4-[5-(2-fluoro-biphenyl-4-yl)-1,2,4-oxadiazole-3-yl]benzyl}(2-hydroxyethyl)-amino]ethanol (31 g, 0.0715 mol) in dichloromethane (150 mL) at 0° C. N,N-Dimethylformamide (2 mL) is added and the reaction mixture is heated at 80° C. for 1 h. Excess thionyl chloride is removed under reduced pressure and the residue is made alkaline (pH ~9) by the addition of an aqueous sodium hydroxide solution (4N, 150 mL) at room temperature. The aqueous layer is extracted with ethyl acetate (2×100 mL) and combined organic layers are dried over sodium sulphate. Removal of solvent under reduced pressure gives a viscous liquid, which is purified by column chromatography (silica gel 230-400 mesh, n-hexane:ethyl acetate 7:3) to give bis-(2-chloroethyl){4-[5-(2-fluorobiphenyl-4-yl)-1,2,4-oxadiazole-3-yl]benzyl}amine.

Potassium carbonate (22.4 g, 0.162 mol) and tetrabutylammonium bromide (30.5 g, 0.095 mol) are added to a stirred solution of bis-(2-chloroethyl){4-[5-(2-fluorobiphenyl-4-yl)-1,2,4-oxadiazole-3-yl]benzylamine (28 g, 0.059 mol) and dibenzyl malonate (15.3 g, 0.054 mol) in N,N-dimethylformamide (250 mL). The reaction mixture is heated at 100° C. for 4 hrs and concentrated under reduced pressure. The residue is treated with demineralized water (200 mL) followed by brine (25 mL) and the aqueous layer is extracted with tetrahydrofuran (2×150 mL). Combined organic layers are dried over sodium sulphate and concentrated under reduced pressure to give a viscous liquid, which is purified by column chromatography (silica gel 230-400 mesh, n-hexane:ethyl acetate 70:30) to give 1-{4-[5-(2-fluoro-biphenyl-4-yl)-1,2,4-oxadiazole-3-yl]benzyl}piperidine-4,4-dicarboxylic acid dibenzyl ester.

Step-V

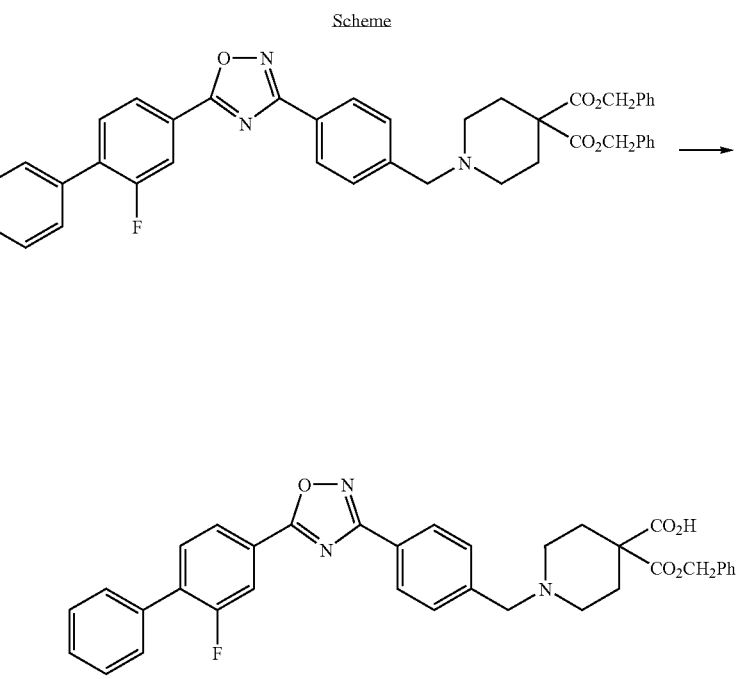

An aqueous solution (50 mL) of sodium hydroxide (1.7 g, 0.043 mol) is added to a stirred solution of 1-{4-[5-(2-fluorobiphenyl-4-yl)-1,2,4-oxadiazole-3-yl]benzyl}piperidine-4,4-dicarboxylic acid dibenzyl ester (18.3 g, 0.027 mol) in tetrahydrofuran (150 mL). The reaction mixture is stirred overnight at room temperature and then concentrated under reduced pressure. The residue is acidified to pH ~6 with diluted hydrochloric acid to give a solid which is filtered and washed with diethylether (100 mL) to furnish 1-{4-[5-(2-fluorobiphenyl-4-yl)-1,2,4-oxadiazole-3-yl] benzyl}piperidine-4,4-dicarboxylic acid mono benzyl ester.

Step-VI

Scheme

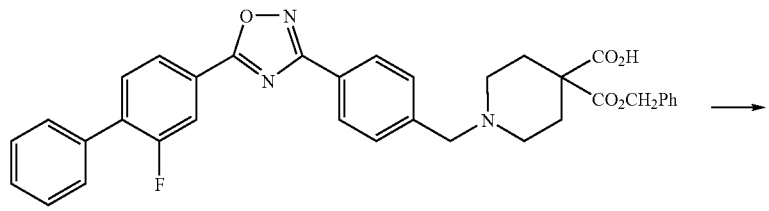

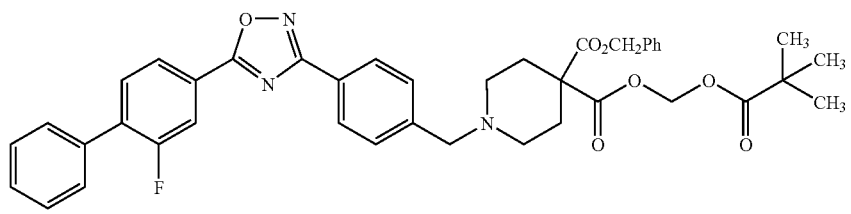

Sodium carbonate (0.125 g, 0.0012 mol) is added to a solution of 1-{4-[5-(2-fluorobiphenyl-4-yl)-1,2,4-oxadiazole-3-yl]benzyl}piperidine-4,4-dicarboxylic acid mono benzyl ester (0.35 g, 0.00059 mol) in N,N-dimethylacetamide (3.5 mL). The reaction mixture is stirred for 30 minutes at room temperature. Chloromethyl pivalate (0.187 g, 0.0012 mol) is added to the reaction mixture which is then heated at 65° C. for 4 hrs. The reaction mixture is treated with demineralized water (5 mL) and extracted in ethyl acetate (2×5 mL). Sodium chloride (0.25 g) is added to the ethyl acetate layer and stirred for 15 minutes. Demineralized water (5 mL) is added to the ethyl acetate layer and the layers are separated. The ethyl acetate layer is dried over sodium sulphate. Removal of solvent under reduced pressure gives a viscous liquid, which is purified by column chromatography (silica gel 230-400 mesh, n-hexane:ethyl acetate 70:30) to furnish 1-{4-[5-(2-fluorobiphenyl-4-yl)-1,2,4oxadiazol-3-yl]benzyl}-piperidine-4,4-dicarboxylic acid benzyl ester (2,2-dimethylpropanoyloxymethyl) ester.

Step-VII

Scheme

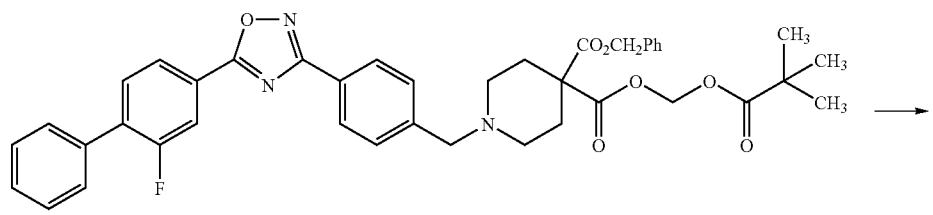

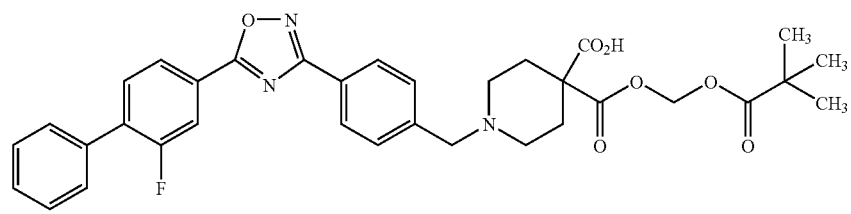

To a solution of 1-{4-[5-(2-fluorobiphenyl-4-yl)-1,2,4-oxadiazol-3-yl]benzyl}-piperidine-4,4-dicarboxylic acid benzyl ester (2,2-dimethyl-propanoyl-oxymethyl) ester (0.37 g, 0.00052 mol) in a mixture of ethanol and ethyl acetate (20 mL, 1:1) is added 5% Pd/C (0.133 g). The reaction mixture is stirred at room temperature and hydrogen gas is bubbled through it. This process is continued for 2.5 hours. The reaction mixture is filtered through a celite bed, washed with tetrahydrofuran (2×30 mL) and the filtrate is concentrated under reduced pressure to give a solid mass which is purified by column chromatography (silica gel 230-400 mesh, methanol:dichloromethane 15:85) to give 1-{4-[5-(2-fluorobiphenyl-4-yl)-1,2,4-oxadiazol-3-yl]benzyl}-piperidine-4,4-dicarboxylic acid (2,2-dimethyl-propanoyloxymethyl)ester (e.g. 39).

Alternate preparations of 1-{4-[5-(2-fluorobiphenyl-4-yl)-1,2,4oxadiazol-3-yl]benzyl}piperidine-4,4-dicarboxylic acid benzyl ester (2,2-dimethylpropanoyl-oxymethyl) ester.

N,N-Bis(2-chloroethyl)carbamic acid tert-butyl ester

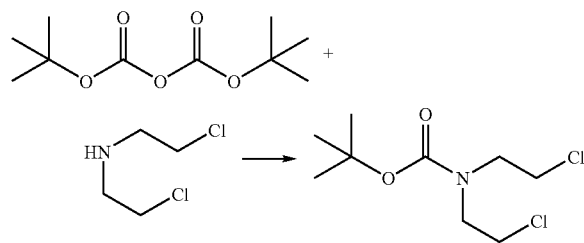

To a mixture of di-tert-butyldicarbonate (6.2 g 0.28 mol) and bis(2-chloroethyl)amine, hydrochloride (5.5 g 0.31 mol) in dichloromethane (40 mL) is added triethylamine (4.2 mL 0.3 mol). pH is then adjusted to 9-9.5 by further addition of triethylamine (0.5 mL) and the mixture is stirred for 2 h at room temperature, diluted with dichloromethane, washed with water, dried over magnesium sulfate and concentrated under reduced pressure to give crude N,N-bis(2-chloroethyl)carbamic acid tert-butyl ester used without further purification in the next step.

Piperidine-1,3,3-tricarboxylic acid 1-tert-butyl 3,3-dibenzyl ester

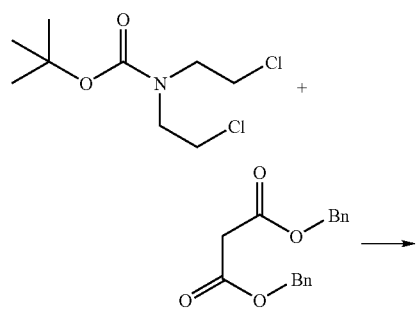

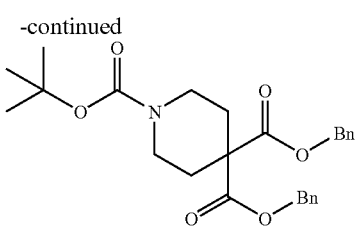

A mixture of N,N-bis(2-chloroethyl)carbamic acid tert-butyl ester (1.22 g 5 mmol), dibenzyl malonate (1.42 g 5 mmol), potassium carbonate (1.38 g 10 mmol) and tetrabutylammonium bromide (0.5 g 1.55 mmol) in toluene (20 mL) is heated under reflux. Additional portion of tetrabutylammonium bromide (0.5 g 1.55 mmol) is added after 2 h reflux (twice). After further heating for 2 h (overall 6 h heating) the mixture is cooled back to room temperature and diethyl oxyde is added (50 mL). The organic phase is washed with water, dried and concentrated under reduced pressure. Purification by column chromatography affords piperidine-1,3,3-tricarboxylic acid 1-tert-butyl 3,3-dibenzyl ester as an oil.

Piperidine-1,3,3-tricarboxylic acid 1-tert-butyl 3-benzyl ester

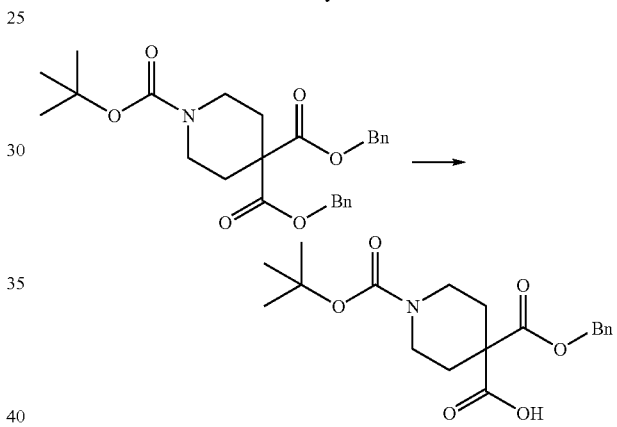

To a solution of piperidine-1,3,3-tricarboxylic acid 1-tert-butyl 3,3-dibenzyl ester (3.59 g 7.9 mmol) in N,N-dimethylformamide (100 mL) cooled with a water/ice bath, is added dropwise a solution of potassium hydroxyde (0.68 g 85% 10 mmol) in water (29 mL). The mixture is further stirred with cooling for 2 h, then allowed to warm to room temperature and acidified with acetic acid (1.05 eq). After concentration under reduced pressure, the crude product is dissolved in diisopropyl oxyde, washed with water, dried over magnesium sulphate and concentrated under reduced pressure to give piperidine-1,3,3-tricarboxylic acid 1-tert-butyl 3-benzyl ester as an oil.

Piperidine-1,3,3-tricarboxylic acid 1-tert-butyl 3-benzyl 3-(3,3-dimethyl-2-oxobutyl)ester

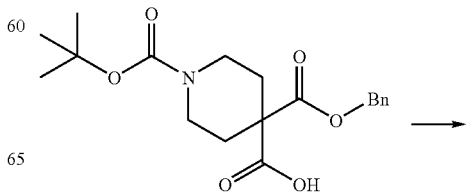

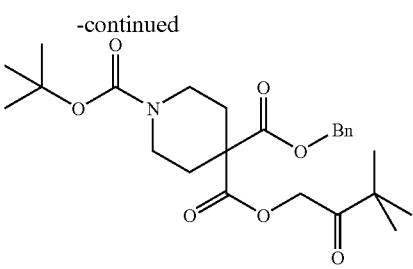

A mixture of piperidine-1,3,3-tricarboxylic acid 1-tert-butyl 3-benzyl ester (2.85 g 7.85 mmol), potassium carbonate (1.4 g 10 mmol) and bromopinacolone (1.73 mL 17 mmol) in butan-2-one is stirred at room temperature for 6 h. The mixture is washed with water, dried over magnesium sulphate and concentrated under reduced pressure. After purification by column chromatography, the product is crystallized in heptane to give piperidine-1,3,3-tricarboxylic acid 1-tert-butyl 3-benzyl 3-(3,3-dimethyl-2-oxobutyl)ester melting at 60° C.

Piperidine-3,3-dicarboxylic acid 3-benzyl 3-(3,3-dimethyl-2-oxobutyl)ester

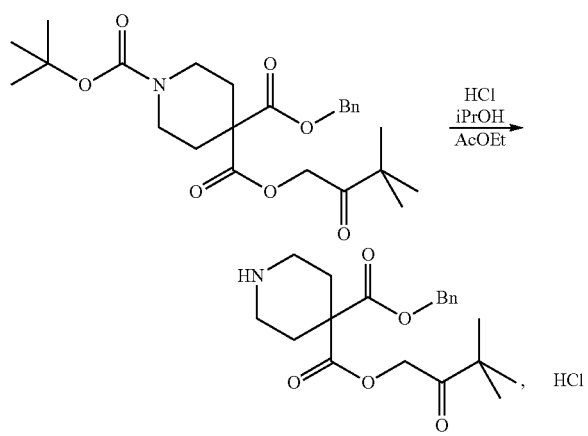

To a solution of piperidine-1,3,3-tricarboxylic acid 1-tert-butyl 3-benzyl 3-(3,3-dimethyl-2-oxobutyl)ester (250 mg 0.54 mmol) in ethyl acetate (3 mL) is added a solution of hydrogen chloride in isopropanol (3 mL 5-6N). The mixture is stirred at room temperature for 3 h, then concentrated under reduced pressure. The solid is triturated in diisopropyl oxide to give piperidine-3,3-dicarboxylic acid 3-benzyl 3-(3,3-dimethyl-2-oxobutyl)ester, hydrochloride melting at 1500.

Bis(2-chloroethyl)benzylamine

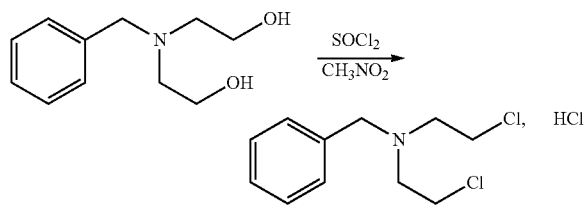

To a solution of bis(2-hydroxyethyl)benzylamine (19.5 g 0.1 mol) in nitromethane (150 mL) cooled with a water/ice bath is added thionyl chloride (60 mL). The mixture is stirred at room temperature for 2 h, then at 80° C. for 1 h 30. After cooling again with a water/ice bath, diisopropyl oxyde (350 mL) is added, causing the hydrochloride to precipitate. This is filtrated, rinsed with diisopropyl oxide and dried to give bis(2-chloroethyl)benzylamine hydrochloride.

1-Benzylpiperidine-3,3-dicarboxylic acid 3,3-dibenzyl ester

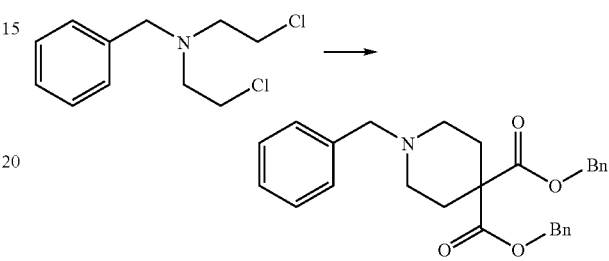

A solution of bis(2-chloroethyl)benzylamine, hydrochloride (3.4 g 12.6 mmol) in iced water (10 mL) is made alcaline with a 5N aqueous solution of sodium hydroxyde. Extraction with ethyl acetate, drying of the organic phase over magnesium sulphate and evaporation under reduced pressure affords bis(2-chloroethyl)benzylamine.

Part of the latter (2.5 g) is dissolved in ethyl acetate/DMSO (1/1 25 mL). Dibenzylmalonate (5.3 g 18.6 mmol) and potassium carbonate (5 g, 36 mmol) are added followed by a solution of tetrabutylammonium bromide in ethyl acetate/DMSO (1/1 25 mL), and the mixture is heated under reflux for 3 h. Solvents are evaporated under reduced pressure. The residue is dissovled in diethyl oxyde, washed with water, dried over magnesium sulfate and concentrated under reduced pressure. Purification of the residue by column chromatography gives 1-benzylpiperidine-3,3-dicarboxylic acid 3,3-dibenzyl ester.

Piperidine-1,3,3-tricarboxylic acid 1-(2,2,2-trichloroethyl) 3,3-dibenzyl ester

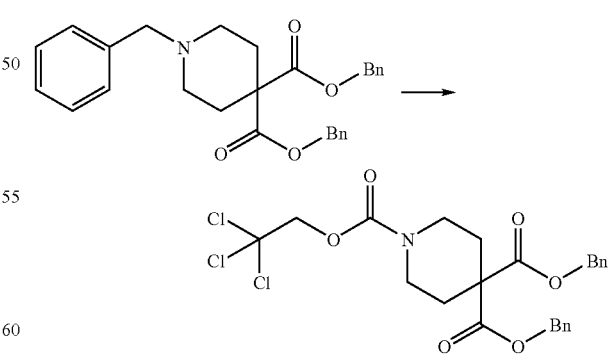

To a mixture of 1-benzylpiperidine-3,3-dicarboxylic acid 3,3-dibenzyl ester (19.6 g 41.8 mmol) and sodium carbonate (5.1 g, 48.1 mmol) in chloroform cooled with a water/ice bath, is added 2,2,2-trichloroethyl chloroformate (11 g, 51.8 mmol). The mixture is stirred overnight at room temperature and concentrated under reduced pressure. The residue is dissolved in diethyl oxide, washed with water, dried over magnesium sulphate and concentrated under reduced pressure to give piperidine-1,3,3-tricarboxylic acid 1-(2,2,2-trichloroethyl) 3,3-dibenzyl ester which cristallizes upon standing.
Melting point 76° C.

Piperidine-1,3,3-tricarboxylic acid 1-tert-butyl 3-benzyl ester

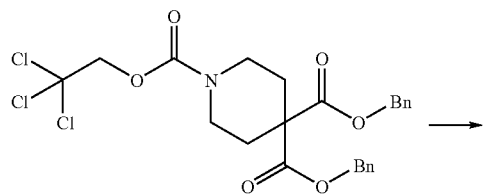

To a solution of piperidine-1,3,3-tricarboxylic acid 1-(2,2,2-trichloroethyl) 3,3-dibenzyl ester (5.5 g 15 mmol) in N,N-dimethylformamide (200 mL) cooled with a water/ice bath, is added potassium hydroxyde (0.9 g 85% 14 mmol) dissolved in water (40 mL). The mixture is stirred with cooling for 2 h, allowed to warm to room temperature, acidified with acetic acid (1.05 ew) and concentrated under reduced pressure. Addition of water cristallizes the crude which is filtered, dissolved in ethyl acetate, washed with water, dried over magnesium sulphate and concentrated under reduced pressure. Cristallisation with heptane affords piperidine-1,3,3-tricarboxylic acid 1-(2,2,2-trichloroethyl) 3-benzyl ester.

Piperidine-1,3,3-tricarboxylic acid 1-(2,2,2-trichloroethyl) 3-benzyl 3-(3,3-dimethyl-2-oxobutyl)ester

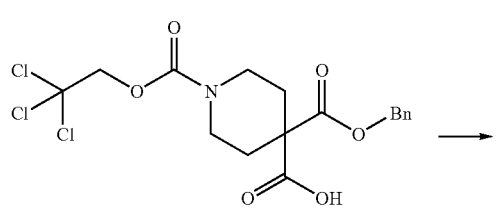

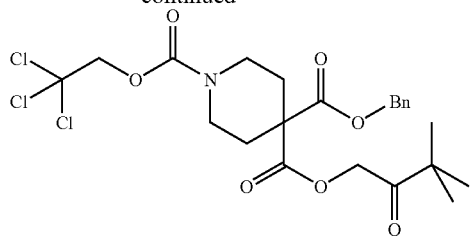

A mixture of piperidine-1,3,3-tricarboxylic acid 1-(2,2,2-trichloroethyl) 3-benzyl ester (3.9 g 8.8 mmol), potassium carbonate (1.83 g 13 mmol) and bromopinacolone (2.31 g 13 mmol) in N,N-dimethylformamide (55 mL) is heated at 60° C. for 2 h. The mixture is cooled back to room temperature, neutralized with acetic acid (13 mmol) and concentrated under reduced pressure. the residue is dissolved in ethyl acetate, washed with water and concentrated. Cristallization in diethyl oxide gives piperidine-1,3,3-tricarboxylic acid 1-(2,2,2-trichloroethyl) 3-benzyl 3-(3,3-dimethyl-2-oxobutyl)ester melting at 114° C.

Piperidine-3,3-dicarboxylic acid 3-benzyl 3-(3,3-dimethyl-2-oxobutyl)ester

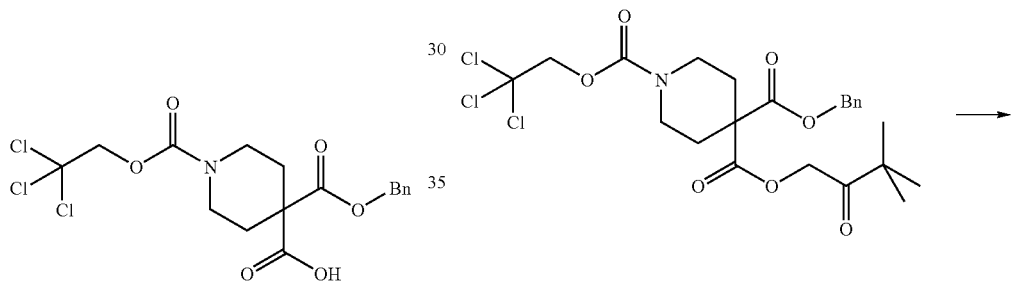

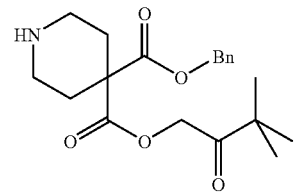

A mixture of piperidine-1,3,3-tricarboxylic acid 1-(2,2,2-trichloroethyl) 3-benzyl 3-(3,3-dimethyl-2-oxobutyl)ester (1.6 g 3 mmol) and zinc (10.5 g 0.16 mol) in a mixture of tetrahydrofurane (25 mL) and 1M aqueous solution of ammonium acetate (13 mL) is stirred overnight at room temperature, diluted with tetrahydrofurane (20 mL) and filtrated over clarcel. The filtrate is diluted with dichloromethane, washed with water dried over magnesium sulfate and concentrated under reduced pressure to give piperidine-3,3-dicarboxylic acid 3-benzyl 3-(3,3-dimethyl-2-oxobutyl)ester as an oil 1-{4-[5-(2-Fluorobiphenyl-4-yl)[1,2,4]oxadiazol-3-yl]benzyl}piperidine-4,4-dicarboxylic acid benzyl ester 3,3-dimethyl-2-oxobutyl ester

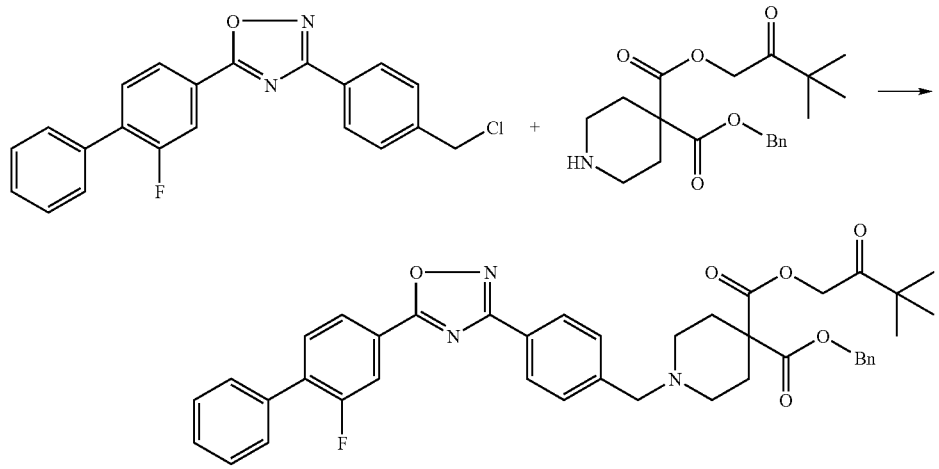

Condensation of piperidine-3,3-dicarboxylic acid 3-benzyl 3-(3,3-dimethyl-2-oxobutyl)ester onto 3-(4-chloromethylphenyl)-5-(2-fluorobiphenyl-4-yl)[1,2,4]oxadiazole is performed as described in step II for the preparation of 2-[{4-[5-(2-fluorobiphenyl-4-yl)-1,2,4-oxadiazole-3-yl]benzyl}(2-hydroxyethyl)amino]-ethanol, with piperidine-3,3-dicarboxylic acid 3-benzyl 3-(3,3-dimethyl-2-oxobutyl)ester replaced by diethanolamine. This procedures affords 1-{4-[5-(2-fluorobiphenyl-4-yl)[1,2,4]oxadiazol-3-yl]benzyl}piperidine-4,4-dicarboxylic acid benzyl ester 3,3-dimethyl-2-oxobutyl ester.

Examples 38-47 are prepared in a similar manner.

| Ex. | R | $R_1$ | $R_2$ | $R_3$ | $R_4$ | $R_5$ | $R_6$ | MS(ESI$^+$) |
|---|---|---|---|---|---|---|---|---|
| 38 | Ph | F | H | H | H | OH | -O-CH(CH₃)-O-C(O)-CH₃ | 588.1 |
| 39 | Ph | F | H | H | H | OH | -O-CH₂-O-C(O)-C(CH₃)₂-CH₃ | 616.1 |
| 40 | Ph | F | H | H | H | OH | (4-methyl-5-methoxymethyl-1,3-dioxol-2-one) | 614 |
| 41 | Ph | F | H | H | H | OH | -O-CH₂-O-C(O)-O-CH(CH₃)₂ | 618.1 |
| 42 | Ph | F | H | H | H | OH | -O-CH(CH₃)-O-C(O)-O-cyclohexyl | 672.2 |

-continued
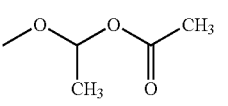
| Ex. | R | R₁ | R₂ | R₃ | R₄ | $R_5$ | $R_6$ | MS(ESI⁺) |
|---|---|---|---|---|---|---|---|---|
| 43 | Ph | F | H | H | H | OMe | 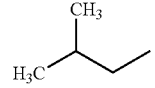 | 602.1 |
| 44 | sec-Bu (CH₃ / H₃C-CH-CH₂-) | H | H | H | H | OMe | 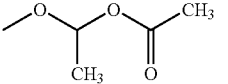 | 564.2 |
| 45 | Ph | F | H | H | H | OMe | 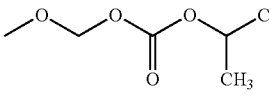 | 632.1 |
| 46 | Ph | F | H | H | H | OMe | 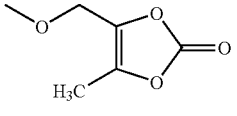 | 628.1 |
| 47 | Ph | F | H | H | H | 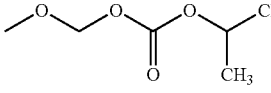 | 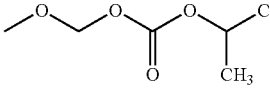 | 734.24 |
Following compounds of cycloalkane derivatives are also prepared by employing either Method A or Method B.
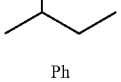
| Ex. | R | R1 | R2 | R3 | R4 | R6 | R7 | R8 | MS(ES⁺) |
|---|---|---|---|---|---|---|---|---|---|
| 48 | 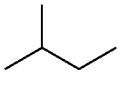 | H | H | H | H | H | H | OH | 450 |
| 49 | Ph | F | H | H | H | H | H | OH | |
| 50 | 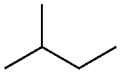 | H | H | H | H | CH₃ | H | OH | 464.17 |
| 51 | Ph | F | H | H | H | CH₃ | H | OH | 502.03 |
| 52 | Ph | F | H | H | H | CH₃ | H | OMe | 516.1 |
| 53 | iso-Bu | H | H | H | H | CH₃ | H | OMe | 478.12 (Isomer A) |

-continued

| | Compound | | | | | | | | |
|---|---|---|---|---|---|---|---|---|---|

Structure: R1, R2, R3, R4, R substituents on phenyl; phenyl-oxadiazole-phenyl-CH2-N(R6)-cyclobutane with CO2R7 and COR8

| Ex. | R | R1 | R2 | R3 | R4 | R6 | R7 | R8 | MS(ES+) |
|---|---|---|---|---|---|---|---|---|---|
| 54 | sec-butyl | H | H | H | H | CH3 | H | OMe | 478.13 (Isomer B) |

| 55 | [4-isobutylphenyl-oxadiazole-phenyl-CH2-NH-cyclopentane(CO2H)2] | 464.1 |
|---|---|---|

| 56 | [4-(cyclopropylmethyl)phenyl-oxadiazole-phenyl-CH2-NH-cyclopentane(CO2H)2] | 462.1 |
|---|---|---|

| 57 | [4-isobutylphenyl-oxadiazole-phenyl-CH2-NH-cyclohexane(CO2H)2] | 478.0 |
|---|---|---|

| 58 | [2-fluoro-biphenyl-oxadiazole-phenyl-CH2-NH-cyclohexane(CO2H)2] | 516.1 |
|---|---|---|

| 59 | [2-fluoro-biphenyl-oxadiazole-phenyl-CH2-N(CH3)-cyclohexane(CO2H)2] | 530.5 |
|---|---|---|

¹H-NMR Data

Example 1 as HCl

¹H NMR: (CDCl$_3$+TFA; 400.13 MHz; δ ppm)
0.94 (d, J=6.64 Hz, 6H); 1.96 (septet, J=6.68 Hz, 1H); 2.60-2.72 (br m, 6H); 3.00-3.10 (br s, 2H); 3.77-3.82 (br s, 2H); 4.39 (s, 2H); 7.39 (d, J=8.16 Hz, 2H); 7.61-7.70 (br s, 2H); 8.10 (d, J=8.20 Hz, 2H); 8.16-8.23 (br d, 2H) Three exchangeable protons.

Example 2 as HCl

¹H NMR: (CDCl$_3$+TFA; 400.13 MHz; δ ppm)
1.77 (s, 3H); 1.81 (s, 3H); 2.38-2.50 (br m, 2H); 2.65-2.78 (br d, 2H); 3.10-3.25 (br s, 2H); 3.73-3.85 (br s, 2H); 4.43 (s, 2H); 4.89 (d, J=7.47 Hz, 2H); 5.41 (t, J=7.38 Hz, 1H); 7.10 (d, J=8.42 Hz, 2H); 7.58-7.69 (s, 2H); 8.15 (d, J=8.24 Hz, 4H) Three exchangeable protons.

Example 3 as HCl

¹H NMR: (CDCl$_3$+CD$_3$OD+TFA; 400.13 MHz; δ ppm)
2.40-2.80 (br m, 4H); 3.10-3.31 (br s, 2H); 3.62-3.83 (br s, 2H); 4.32-4.54 (br s, 2H); 7.45-7.55 (m, 3H); 7.62-7.77 (m, 5H); 8.03 (d, J=10.56 Hz, 1H); 8.10 (d, J=7.98 Hz, 1H); 8.21-8.29 (br s, 2H) Three exchangeable protons.

Example 4 in the Free Form

¹H NMR: (CDCl$_3$+CD$_3$OD+TFA; 400.13 MHz; δ ppm)
2.32-2.48 (br m, 2H); 2.59-2.71 (br d, 2H); 3.08-3.24 (br s, 2H); 3.63-3.76 (br t, 2H); 3.81 & 3.86 (s, 3H); 4.34-4.45 (br s, 2H); 7.44-7.56 (m, 3H); 7.60-7.68 (br d, 4H); 7.72 (t, J=7.77 Hz, 1H); 8.02 (d, J=10.51 Hz, 1H); 8.10 (d, J=8.02 Hz, 1H); 8.22-8.29 (br s, 2H) One exchangeable proton.

Example 5 as HCl

¹H NMR: (CDCl$_3$+TFA+DMSO-d$_6$+D$_2$O; 400.13 MHz; δ ppm)
0.22-0.29 (m, 2H); 0.56-0.62 (m, 2H); 0.99-1.14 (m, 1H); 2.20-2.30 (m, 2H); 2.55 (d, J=14.70 Hz, 2H); 2.65 (d, J=6.90 Hz, 2H); 3.07 (t, J=12.26 Hz, 2H); 3.54 (d, J=12.47 Hz, 2H); 4.28 (s, 2H); 7.47 (d, J=8.14 Hz, 2H); 7.56 (d, J=8.17 Hz, 2H); 8.12 (d, J=8.14 Hz, 2H); 8.22 (d, J=8.14 Hz, 2H) Three exchangeable protons.

Example 6 as HCl

¹H NMR: (CDCl$_3$+TFA+DMSO-d$_6$+D$_2$O; 400.13 MHz; δ ppm)
0.23-0.29 (m, 2H); 0.56-0.62 (m, 2H); 1.00-1.09 (m, 1H); 2.21-2.39 (m, 2H); 2.54 (d, J=15.10 Hz, 2H), 2.65 (d, J=6.90 Hz, 2H); 2.90-2.99 (br t, 1H); 3.02-3.10 (br t, 1H); 3.54-3.64 (br t, 2H); 3.73-3.82 (s, 3H); 4.28 (s, 2H); 7.47 (d, J=8.16 Hz, 2H); 7.56 (d, J=8.20 Hz, 2H); 8.14 (d, J=8.21 Hz, 2H); 8.24 (dd, J$_1$=8.17 Hz, J$_2$=2.51 Hz, 2H) Two exchangeable protons.

Example 7 as HCl

¹H NMR: (CDCl$_3$+TFA; 400.13 MHz; δ ppm)
1.79 (s, 3H); 1.83 (s, 3H); 2.30-2.44 (br m, 2H); 2.57-2.67 (br d, 2H); 3.04-3.20 (br m, 2H); 3.63-3.73 (br d, 2H); 3.80 & 3.85 (s, 3H); 4.36 (s, 2H); 4.67 (d, J=6.76 Hz, 2H); 5.52 (t, J=6.72 Hz, 1H); 7.11 (d, J=8.85 Hz, 2H); 7.62 (d, J=6.68 Hz, 2H); 8.13-8.22 (m, 4H). One exchangeable proton.

Example 8 in the Free Form

¹H NMR: (CDCl$_3$+CD$_3$OD+TFA; 400.13 MHz; δ ppm)
0.95 (d, J=6.65 Hz, 6H); 1.97 (septet, J=6.75 Hz, 1H); 2.26-2.42 (br m, 2H); 2.62 (d, J=7.12 Hz, 2H); 2.60-2.69 (br d, 2H); 3.05-3.23 (br m, 2H); 3.62-3.73 (br d, 2H); 3.81 & 3.86 (s, 3H); 4.38 (s, 2H); 7.40 (d, J=8.20 Hz, 2H); 7.57-7.64 (br, 2H); 8.12 (d, J=8.16 Hz, 2H); 8.18-8.24 (br, 2H). One exchangeable proton.

Example 9 in the Free Form

¹H NMR: (CDCl$_3$+TFA; 400.13 MHz; δ ppm)
1.55 (s, 6H); 2.31-2.43 (br t, 2H); 2.54-2.64 (br d, 2H); 3.00-3.10 (m, 2H); 3.12 (s, 2H); 3.67-3.78 (br m, 2H); 3.79 & 3.87 (s, 3H); 4.35 (s, 2H); 6.91 (d, J=8.37 Hz, 1H); 7.54 (d, J=7.62 Hz, 2H); 7.97-8.04 (m, 2H); 8.17 (t, J=7.52 Hz, 2H). One exchangeable proton.

Example 10 as HCl

¹H NMR: (CDCl$_3$+TFA; 400.13 MHz; δ ppm)
1.56 (s, 6H); 2.30-2.45 (br t, 2H); 2.59-2.69 (br d, 2H); 3.01-3.12 (br m, 2H); 3.12 (s, 2H); 3.76 (d, J=10.26 Hz, 2H); 4.36 (s, 2H); 6.91 (d, J=8.37 Hz, 1H); 7.55 (d, J=7.40 Hz, 2H); 7.95-8.05 (m, 2H); 8.16 (d, J=7.54 Hz, 2H). Three exchangeable protons.

Example 11 as HCl

¹H NMR: (CDCl$_3$+CD$_3$OD+TFA; 400.13 MHz; δ ppm)
2.24-2.40 (br t, 2H); 2.57 (d, J=14.34 Hz, 2H); 3.01-3.15 (br t, 2H); 3.56 (d, J=11.17 Hz, 2H); 4.31 (s, 2H); 6.94-7.07 (m, 2H); 7.45-7.55 (m, 1H); 7.64 (d, J=7.77 Hz, 2H); 7.73 (d, J=7.42 Hz, 2H); 8.25 (d, J=7.75 Hz, 2H); 8.28 (d, J=8.33 Hz, 2H) Three exchangeable protons.

Example 12 as HCl

¹H NMR: (CDCl$_3$+TFA+DMSO-d$_6$; 400.13 MHz; δ ppm)
2.33-2.47 (br m, 2H); 2.60-2.70 (br t, 2H); 3.15-3.28 (br s, 2H); 3.60-3.72 (br d, 2H); 4.39 (s, 2H); 7.20 (t, J=8.65 Hz, 2H); 7.62-7.71 (m, 4H); 7.80 (d, J=8.34 Hz, 2H); 8.24 (d, J=7.22 Hz, 2H); 8.29 (d, J=8.34 Hz, 2H); Three exchangeable protons.

Example 13 as HCl

¹H NMR: (CDCl$_3$+TFA+CD$_3$OD; 400.13 MHz; δ ppm)
2.32-2.49 (br t, 2H); 2.70 (d, J=13.62 Hz, 2H); 3.12-3.24 (br s, 2H); 3.75-3.82 (br d, 2H); 4.42 (s, 2H); 6.89 (t, J=8.67 Hz, 1H); 7.20 (d, J=6.20 Hz, 2H); 7.61 (d, J=6.29 Hz, 2H); 7.81 (d, J=8.15 Hz, 2H); 8.22 (d, J=6.44 Hz, 2H); 8.30 (d, J=8.16 Hz, 2H). Two exchangeable protons.

Example 14 as HCl

¹H NMR: (CDCl$_3$+CD$_3$OD+TFA; 400.13 MHz; δ ppm)
2.27-2.42 (br m, 2H); 2.53-2.66 (br d, 2H); 3.00-3.18 (br s, 2H); 3.60-3.72 (br d, 2H); 4.34 (s, 2H); 7.59 (d, J=6.37 Hz, 2H); 7.86 (d, J=8.26 Hz, 2H); 8.24 (d, J=6.67 Hz, 2H); 8.35 (d, J=8.15 Hz, 2H) Three exchangeable protons.

Example 15 as HCl $^1$H NMR: (CDCl$_3$+TFA+CD$_3$OD+D$_2$O; 400.13 MHz; δ ppm)

2.26 (t, J=13.10 Hz, 2H); 2.55 (d, J=14.74 Hz, 2H); 3.06 (t, J=12.70 Hz, 2H); 3.57 (d, J=12.26 Hz, 2H); 4.30 (s, 2H); 7.39-7.46 (m, 1H); 7.49 (t, J=7.60 Hz, 2H); 7.57 (d, J=8.06 Hz, 2H); 7.66 (d, J=7.36 Hz, 2H); 7.79 (d, J=8.25 Hz, 2H); 8.20-8.30 (m, 4H). Three exchangeable protons.

Example 16 as HCl $^1$H NMR: (CDCl$_3$+CD$_3$OD+TFA; 400.13 MHz; δ ppm)

2.27-2.43 (br t, 2H); 2.62 (br, J=13.34 Hz, 2H); 3.05-3.20 (br, 2H); 3.59-3.72 (br, 2H); 4.36 (s, 2H); 7.43 (d, J=8.36 Hz, 2H); 7.61 (d, J=5.79 Hz, 2H); 8.23 (d, J=5.66 Hz, 2H); 8.28 (d, J=8.71 Hz, 2H); Three exchangeable protons.

Example 17 as HCl $^1$H NMR: (CDCl$_3$+CD$_3$OD+TFA; 400.13 MHz; δ ppm)

2.25 (t, J=12.69 Hz, 2H); 2.57 (d, J=14.67 Hz, 2H); 3.08 (t, J=12.35 Hz, 2H); 3.54 (d, J=12.14 Hz, 2H); 4.31 (s, 2H); 7.61 (d, J=8.00 Hz, 2H); 7.73 (dd, J$_1$=11.87 Hz, J$_2$=8.78 Hz, 1H); 7.82-7.89 (m, 1H); 8.18 (d, J=7.89 Hz, 3H) Three exchangeable protons.

Example 18 as HCl $^1$H NMR: (CDCl$_3$+CD$_3$OD+TFA; 400.13 MHz; δ ppm)

2.30-2.45 (br m, 2H); 2.61-2.71 (br d, 2H); 3.10-3.21 (br m, 2H); 3.24 (s, 3H); 3.65-3.77 (br d, 2H); 4.39 (s, 2H); 7.54-7.65 (br d, 2H); 8.18 (d, J=8.16 Hz, 2H); 8.22-8.29 (br, 2H); 8.48 (d, J=8.24 Hz, 2H) Three exchangeable protons.

Example 19 as HCl $^1$H NMR: (CDCl$_3$+CD$_3$OD+TFA; 400.13 MHz; δ ppm)

1.55-1.70 (m, 2H); 1.80-1.93 (m, 2H); 2.09 (d, J=11.24 Hz, 2H); 2.25-2.40 (br m, 4H); 2.55 (d, J=14.62 Hz, 2H); 2.59-2.69 (m, 1H); 2.96-3.07 (br t, 2H); 3.07-3.16 (m, 1H); 3.56 (d, J=11.95 Hz, 2H); 4.28 (s, 2H); 7.27-7.33 (m, 4H); 7.56 (d, J=8.12 Hz, 2H); 8.13 (d, J=8.09 Hz, 2H) Three exchangeable protons.

Example 20 as HCl $^1$H NMR: (CDCl$_3$+TFA; 400.13 MHz; δ ppm)

1.69 (s, 6H); 2.38-2.52 (br s, 2H); 2.65-2.78 (br s, 2H); 3.11-3.27 (br s, 2H); 3.74-3.89 (br s, 2H); 4.44 (s, 2H); 5.35 (s, 2H); 7.41 (d, J=7.91 Hz, 1H); 7.58-7.70 (br s, 2H); 8.12 (s, 1H); 8.22 (d, J=6.60 Hz, 3H). Three exchangeable protons.

Example 21 as HCl $^1$H NMR: (CDCl$_3$+TFA+DMSO-d$_6$+D$_2$O; 400.13 MHz; δ ppm)

2.23-2.35 (br t, 2H); 2.53 (d, J=14.27 Hz, 2H); 3.10 (t, J=12.14 Hz, 2H); 3.54 (d, J=11.61 Hz, 2H); 4.28 (s, 2H); 4.50 (q, J=8.01 Hz, 2H); 7.13 (d, J=8.88 Hz, 2H); 7.59 (d, J=8.20 Hz, 2H); 8.21 (dd, J$_1$=8.06 Hz, J$_2$=4.02 Hz, 4H). Three exchangeable protons.

Example 22 as HCl $^1$H NMR: (CDCl$_3$+TFA+DMSO-d$_6$+D$_2$O; 400.13 MHz; δ ppm)

2.22-2.35 (m, 2H); 2.53 (d, J=14.44 Hz, 2H); 3.01 (t, J=11.94 Hz, 2H); 3.56 (d, J=12.43 Hz, 2H); 4.27 (s, 2H); 4.28 (s, 3H); 6.62-6.65 (m, 1H); 7.51 (d, J=3.80 Hz, 1H); 7.55-7.62 (m, 3H); 8.22 (d, J=8.20 Hz, 2H); Three exchangeable protons.

Example 23 as HCl $^1$H NMR: (CDCl$_3$+CD$_3$OD+TFA; 400.13 MHz; δ ppm)

2.35-2.47 (br t, 2H); 2.55 (d, J=14.59 Hz, 2H); 3.03 (t, J=12.12 Hz, 2H); 3.48-3.56 (br m, 2H); 4.10 (s, 2H); 4.29 (s, 2H); 7.2-7.28 (m, 3H); 7.32 (d, J=7.56 Hz, 2H); 7.41 (d, J=8.21 Hz, 2H); 7.71 (d, J=8.09 Hz, 2H); 8.14 (d, J=8.23 Hz, 2H); 8.24 (d, J=8.02 Hz, 2H) Three exchangeable protons.

Example 24 as HCl $^1$H NMR: (CDCl$_3$+TFA+CD$_3$OD+D$_2$O; 200.13 MHz; δ ppm)

0.87 (d, J=6.74 Hz, 6H); 1.01-1.25 (br s, 3H); 1.35-1.75 (br m, 3H); 1.75-1.99 (br s, 2H); 2.05-2.35 (br d, 4H); 2.35-2.60 (br d, 2H); 2.79-3.18 (br m, 3H); 3.35-3.60 (br d, 2H); 4.23 (s, 2H); 7.51 (d, J=8.13 Hz, 2H); 8.04 (d, J=8.22 Hz, 2H) Three exchangeable protons.

Example 25 as HCl $^1$H NMR: (CDCl$_3$+CD$_3$OD+TFA; 400.13 MHz; δ ppm)

1.60-1.71 (m, 1H); 1.79 (s, 3H); 2.01-2.09 (m, 1H); 2.23-2.47 (m, 2H); 2.45-2.55 (br m, 6H); 2.70-2.79 (br d, 1H); 3.00-3.13 (br s, 2H); 3.60-3.73 (br s, 2H); 4.33 (s, 2H); 4.77 (s, 1H); 4.83 (s, 1H); 7.30 (s, 1H); 7.64 (s, 2H); 8.10 (s, 2H). Three exchangeable protons.

Example 26 as HCl $^1$H NMR: (CDCl$_3$+DMSO-d$_6$+TFA; 400.13 MHz; δ ppm)

1.55 (s, 6H); 2.48-2.55 (br d, 4H); 2.94-3.06 (br m, 2H); 3.42-3.50 (m, 2H); 4.27 (s, 2H); 5.14 (s, 2H); 7.28 (d, J=7.86 Hz, 1H); 7.87 (d, J=8.17 Hz, 2H); 8.00 (s, 1H); 8.09 (d, J=7.87 Hz, 1H); 8.27 (d, J=8.10 Hz, 2H) Three exchangeable protons.

Example 27 as HCl $^1$H NMR: (DMSO-d6+TFA; 400.13 MHz; δ ppm)

2.08-2.20 (br t, 2H); 2.42 (d, J=14.19 Hz, 2H); 3.00-3.13 (br m, 2H); 3.47 (d, J=11.91 Hz, 2H); 4.54 (s, 2H); 7.50-7.55 (m, 1H); 7.59 (t, J=7.43 Hz, 2H); 7.70 (d, J=8.00 Hz, 2H); 7.85 (t, J=8.06 Hz, 1H); 7.89 (d, J=8.24 Hz, 2H); 8.02 (dd, J$_1$=11.18 Hz, J$_2$=1.27 Hz, 1H); 8.08 (dd, J$_1$=7.94 Hz, J$_2$=1.40 Hz, 1H); 8.36 (d, J=8.24 Hz, 2H) Three exchangeable protons.

Example 28 as HCl $^1$H NMR: (CDCl$_3$+CD$_3$OD+TFA; 400.13 MHz; δ ppm)

1.26 (s, 3H); 1.34 (s, 3H); 1.42-1.46 (m, 1H); 1.49 (d, J=10.13 Hz, 1H); 1.97-2.17 (m, 2H); 2.33-2.60 (br m, 4H); 2.67-2.74 (m, 1H); 2.80-3.06 (br m, 3H); 3.32-3.40 (m, 2H); 3.46-3.56 (br d, 2H); 4.27 (s, 2H); 6.18 (s, 1H); 7.65 (d, J=8.15 Hz, 2H); 8.17 (d, J=8.15 Hz, 2H) Three exchangeable protons.

Example 29 as HCl $^1$H NMR: (DMSO-$d_6$+TFA+$D_2O$; 400.13 MHz; δ ppm)
2.02-2.05 (br t, 2H); 2.42 (d, J=14.14 Hz, 2H); 3.04 (t, J=11.57 Hz, 2H); 3.42-3.54 (br d, 2H); 4.45 (s, 2H); 7.64 (t, J=7.71 Hz, 2H); 7.74-7.81 (m, 3H); 7.83 (d, J=7.24 Hz, 2H); 8.01 (d, J=8.26 Hz, 2H); 8.23 (d, J=8.20 Hz, 2H); 8.41 (d, J=8.28 Hz, 2H) Three exchangeable protons.

Example 30 as HCl $^1$H NMR: ($CDCl_3$+TFA+$CD_3OD$; 400.13 MHz; δ ppm)
2.22-2.36 (br t, 2H); 2.59 (d, J=14.49 Hz, 2H); 3.09 (t, J=12.28 Hz, 2H); 3.58 (d, J=12.21 Hz, 2H); 3.99 (s, 3H); 4.32 (s, 2H); 7.63 (d, J=8.05 Hz, 2H); 7.89-7.99 (m, 2H); 8.19 (dd, $J_1$=8.55 Hz, $J_2$=1.16 Hz 1H); 8.28 (d, J=8.02 Hz, 2H) 8.70 (s, 1H) Two aromatic protons are merged between 6.5-7.5 Three exchangeable protons.

Example 31 as HCl $^1$H NMR: ($CDCl_3$+TFA+$CD_3OD$; 400.13 MHz; δ ppm)
2.22-2.40 (br t, 2H); 2.56 (d, J=14.20 Hz, 2H); 3.02 (t, J=11.30 Hz, 2H); 3.50-3.63 (br d, 2H); 4.12 (s, 2H); 4.29 (s, 2H); 7.09-7.17 (br t, 1H); 7.21-7.40 (br m, 5H); 7.61 (d, J=7.26 Hz, 2H); 7.85-7.95 (br t, 1H); 8.24 (d, J=7.12 Hz, 2H) Three exchangeable protons.

Example 32 as HCl $^1$H NMR: (DMSO-$d_6$+TFA; 400.13 MHz; δ ppm)
1.18 (d, J=6.8 Hz, 6H); 2.04-2.18 (br t, 2H); 2.43 (d, J=14.12 Hz, 2H); 3.00-3.15 (br s, 2H); 3.49 (d, J=11.86 Hz, 2H); 3.75 (quintet, J=6.82 Hz, 1H); 4.51 (s, 2H); 7.80 (d, J=8.14 Hz, 2H); 8.25 (2d, J=7.59 Hz, 4H); 8.38 (d, J=8.38 Hz, 2H) Three exchangeable protons.

Example 33 as HCl $^1$H NMR: (DMSO-$d_6$+TFA; 400.13 MHz; δ ppm)
2.05-2.20 (br t, 2H); 2.41 (d, J=14.13 Hz, 2H); 2.96-3.13 (br m, 2H); 3.40-3.52 (br d, 2H); 4.20 (s, 2H); 4.49 (s, 2H); 7.15-7.25 (br, 1H); 7.25-7.38 (m, 2H); 7.54 (d, J=7.90 Hz, 2H); 7.78 (d, J=7.79 Hz, 2H); 8.17 (d, J=8.02 Hz, 2H); 8.21 (d, J=7.80 Hz, 2H) Three exchangeable protons.

Example 34 as HCl $^1$H NMR: (DMSO-$d_6$+TFA; 400.13 MHz; δ ppm)
1.38-1.50 (br t, 3H); 2.07-2.20 (br m, 2H); 2.36-2.48 (br d, 2H); 2.97-3.12 (br s, 2H); 3.40-3.55 (br d, 2H); 4.16-4.28 (br m, 2H); 4.50 (s, 2H); 7.19-7.29 (br d, 2H); 7.76-7.86 (br d, 2H); 8.13-8.28 (br m, 4H) Three exchangeable protons.

Example 35 as HCl $^1$H NMR: ($CDCl_3$+$CD_3OD$+TFA; 400.13 MHz; δ ppm)
1.39 (s, 9H); 2.25-2.38 (br t, 2H); 2.49-2.59 (br d, 2H); 2.94-3.05 (br t, 2H); 3.50-3.59 (br d, 2H); 4.29 (s, 2H); 7.60 (d, J=3.72 Hz, 2H); 7.62 (d, J=3.36 Hz, 2H); 8.14 (d, J=8.40 Hz, 2H); 8.23 (d, J=8.12 Hz, 2H); Three exchangeable protons.

Example 36 as HCl $^1$H NMR: (DMSO-$d_6$+TFA; 400.13 MHz; δ ppm)
1.37 (d, J=6.04 Hz, 6H); 2.14-2.25 (br t, 2H); 2.40 (d, J=13.98 Hz, 2H); 2.95-3.08 (m, 2H); 3.45 (d, J=11.99 Hz, 2H); 4.48 (s, 2H); 4.84 (quintet, J=6.03 Hz, 1H); 7.22 (d, J=8.88 Hz, 2H); 7.84 (d, J=8.19 Hz, 2H); 8.16 (d, J=8.88 Hz, 2H); 8.20 (d, J=8.16 Hz, 2H); Three exchangeable protons.

Example 37 as HCl $^1$H NMR: ($CDCl_3$+$CD_3OD$+TFA; 400.13 MHz; δ ppm)
1.23-1.35 (br m, 1H); 1.37-1.55 (m, 4H); 1.79 (d, J=12.51 Hz, 1H); 1.84-1.97 (br t, 4H); 2.28 (t, J=13.06 Hz, 2H); 2.55 (d, J=14.66 Hz, 2H); 2.58-2.67 (br m, 1H); 3.00 (t, J=12.40 Hz, 2H); 3.55 (d, J=12.14 Hz, 2H); 4.29 (s, 2H); 7.41 (d, J=8.20 Hz, 2H); 7.59 (d, J=8.08 Hz, 2H); 8.13 (d, J=8.18 Hz, 2H); 8.23 (d, J=8.04 Hz, 2H) Three exchangeable protons.

Example 38 in the Free Form $^1$H NMR: ($CDCl_3$+$CD_3OD$; 400.13 MHz; δ ppm)
1.53 (d, J=5.34 Hz, 3H); 2.11 (s, 3H); 2.09-2.25 (br t, 1H); 2.25-2.32 (br s, 2H); 2.35-2.44 (br d, 1H); 2.46-2.59 (br s, 1H); 2.60-2.73 (br s, 1H); 3.13-3.21 (br s, 2H); 3.85-4.04 (br s, 2H); 6.89 (q, J=5.28 Hz, 1H); 7.41-7.53 (m, 4H); 7.55-7.68 (m, 4H); 7.99 (dd, $J_1$=10.62 Hz $J_2$=1.22 Hz-1H); 8.06 (d, $J_1$=8.09 Hz $J_2$=1.30 Hz, 1H); 8.17 (d, J=8.09 Hz, 2H) One exchangeable proton.

Example 39 in the Free Form $^1$H NMR: ($CDCl_3$+$CD_3OD$; 400.13 MHz; δ ppm)
1.22 (s, 9H); 2.20-2.31 (br m, 2H); 2.32-2.42 (br d, 2H); 2.55-2.66 (br t, 2H); 3.06-3.18 (br s, 2H); 3.94 (s, 2H); 5.87 (s, 2H); 7.42-7.57 (m, 5H); 7.6-7.69 (m, 3H); 8.01 (d, J=10.57 Hz, 1H); 8.08 (dd, $J_1$=7.99 Hz, $J_2$=1.13 Hz, 1H); 8.18 (d, J=8.09 Hz, 2H) One exchangeable proton.

Example 40 in the Free Form $^1$H NMR: ($CDCl_3$+$CD_3OD$; 400.13 MHz; δ ppm)
2.19 (s, 3H); 2.22-2.38 (br m, 4H); 2.55-2.66 (br s, 2H); 3.04-3.15 (br s, 2H); 3.94 (s, 2H); 4.98 (s, 2H); 7.42-7.70 (m, 8H); 8.01 (d, J=10.61 Hz, 1H); 8.08 (dd, $J_1$=8.08 Hz, $J_2$=1.23 Hz, 1H); 8.17 (d, J=8.14 Hz, 2H) One exchangeable proton.

Example 41 in the Free Form $^1$H NMR: ($CDCl_3$+$CD_3OD$; 400.13 MHz; δ ppm)
1.31 (d, J=6.24 Hz, 6H); 2.22-2.42 (br m, 4H); 2.54-2.67 (br t, 2H); 3.03-3.18 (br s, 2H); 3.92 (s, 2H); 4.91 (septet, J=6.24 Hz, 1H); 5.85 (s, 2H); 7.42-7.69 (m, 8H); 8.01 (dd, $J_1$=10.56 Hz, $J_2$=1.30 Hz, 1H); 8.07 (dd, $J_1$=8.04 Hz, $J_2$=1.42 Hz, 1H); 8.17 (d, J=8.12 Hz, 2H) One exchangeable proton.

Example 42 in the Free Form $^1$H NMR: ($CDCl_3$; 400.13 MHz; δ ppm)
1.32-1.55 (m, 6H); 1.57 (d, J=5.34 Hz, 3H); 1.71-1.82 (br m, 2H); 1.86-1.99 (br m, 2H); 2.10-2.20 (br m, 1H); 2.27-2.35 (br s, 2H); 2.37-2.45 (br m, 1H); 2.50-2.61 (br s, 1H); 2.65-2.75 (br m, 1H); 3.03-3.15 (br s, 2H); 3.85-3.98 (br s, 2H); 4.58-4.68 (m, 1H); 6.81 (q, J=5.20 Hz, 1H); 7.41-7.7 (m, 8H); 8.01 (d, J=10.64 Hz, 1H); 8.07 (d, J=7.97 Hz, 1H); 8.16 (d, J=8.10 Hz, 2H) One exchangeable proton.

Example 43 in the Free Form $^1$H NMR: (CDCl$_3$; 400.13 MHz; δ ppm)
1.47 (d, J=5.43 Hz, 3H); 2.07 (s, 3H); 2.10-2.30 (br m, 4H); 2.38-2.56 (br m, 4H); 3.54 (s, 2H); 3.74 (s, 3H); 6.87 (q, J=5.40 Hz, 1H); 7.42-7.54 (m, 5H); 7.59-7.67 (m, 3H); 8.02 (d, J=10.7 Hz, 1H); 8.07 (d, J=6.99 Hz, 1H); 8.12 (d, J=8.05 Hz, 2H)

Example 44 in the Free Form $^1$H NMR: (CDCl$_3$; 400.13 MHz; δ ppm)
0.93 (d, J=6.17 Hz, 6H); 1.47 (d, J=4.83 Hz, 3H); 1.87-2.0 (br m, 1H); 2.07 (s, 3H); 2.12-2.23 (br s, 4H); 2.36-2.55 (br m, 4H); 2.57 (d, J=6.76 Hz, 2H); 3.53 (s, 2H); 3.73 (s, 3H); 6.83-6.92 (br q, 1H); 7.32 (d, J=7.51 Hz, 2H); 7.45 (d, J=7.35 Hz, 2H); 8.11 (t, J=6.49 Hz, 4H)

Example 45 in the Free Form $^1$H NMR: (CDCl$_3$; 400.13 MHz; δ ppm)
1.32 (d, J=6.20 Hz, 6H); 2.13-2.25 (br m, 4H); 2.36-2.47 (br d, 2H); 2.48-2.57 (br m, 2H); 3.53 (s, 2H); 3.74 (s, 3H); 4.92 (sept, J=6.20 Hz, 1H); 5.79 (s, 2H); 7.41-7.53 (m, 5H); 7.59-7.68 (m, 3H); 8.02 (dd, J$_1$=10.67 Hz, J$_2$=1.09 Hz, 1H); 8.07 (dd, J$_1$=8.10 Hz, J$_2$=1.29 Hz, 1H); 8.11 (d, J=8.12 Hz, 2H)

Example 46 in the Free Form $^1$H NMR: (CDCl$_3$; 400.13 MHz; δ ppm)
2.12-2.23 (br s, 7H); 2.33-2.45 (br s, 2H); 2.47-2.57 (br m, 2H); 3.53 (s, 2H); 3.73 (s, 3H); 4.90 (s, 2H); 7.41-7.54 (m, 5H); 7.59-7.68 (m, 3H); 8.02 (d, J=10.50 Hz, 1H); 8.08 (d, J=8.03 Hz, 1H); 8.12 (d, J=7.72 Hz, 2H)

Example 47 as Fumarate $^1$H NMR: (CDCl$_3$+CD$_3$OD; 400.13 MHz; δ ppm)
1.32 (d, J=6.08 Hz, 12H); 2.17-2.26 (br t, 4H); 2.50-2.59 (br s, 4H); 3.59 (s, 2H); 4.92 (quintet, J=6.29 Hz, 2H); 5.78 (s, 4H); 6.82 (s, 2H); 7.42-7.54 (m 5H); 7.60-7.69 (m, 3H); 8.01 (d, J=10.71 Hz, 1H); 8.09 (d, J=8.17 Hz, 1H); 8.12 (d, J=7.95 Hz, 2H) Two exchangeable protons.

Example 48 as HCl $^1$H NMR: (CDCl$_3$; 400.13 MHz; δ ppm)
0.95 (d, J=6.66 Hz, 6H); 1.95 (septet, J=6.75 Hz, 1H); 2.61 (d, J=7.21 Hz, 2H); 3.02 (s, 4H); 4.09-4.18 (br s, 1H); 4.33 (s, 2H); 7.39 (d, J=8.16 Hz, 2H); 7.59 (d, J=6.70 Hz, 2H); 8.10 (d, J=8.21 Hz, 2H); 8.18 (d, J=6.63 Hz, 2H) Four exchangeable protons.

Example 49 in the Free Form $^1$H NMR: (CDCl$_3$+CD$_3$OD+TFA; 400.13 MHz; δ ppm)
2.88-2.99 (br m, 2H); 2.99-3.09 (br m, 2H); 4.05-4.17 (br s, 1H); 4.32 (s, 2H); 7.44-7.55 (m, 3H); 7.58-7.67 (m, 4H); 7.71 (t, J=7.81 Hz, 1H); four aromatic protons are merged in 7.93-8.30. Four exchangeable protons.

Example 50 in the Free Form $^1$H NMR: (CDCl$_3$+DMSO-d$_6$; 400.13 MHz; δ ppm)
0.95 (d, J=5.99 Hz, 6H); 1.82-2.03 (br m, 1H); 2.57-2.72 (m, 7H); 2.79-2.9 (br t, 2H); 3.83-3.95 (br t, 1H); 4.27-4.41 (br s, 2H); 7.44-7.55 (br d, 2H); 7.77-7.87 (br d, 2H); 8.12-8.19 (br d, 2H); 8.19-8.26 (br, 2H). Three exchangeable protons.

Example 51 as HCl $^1$H NMR: (CDCl$_3$+TFA+CD$_3$OD; 400.13 MHz; δ ppm)
2.80 (br s, 3H); 3.00-3.21 (br d, 4H); 3.94-4.10 (br s, 1H); 4.14-4.25 (br d, 1H); 4.50-4.60 (br d, 1H); 7.45-7.56 (m, 3H); 7.61-7.68 (d, J=6.87 Hz, 4H); 7.72 (t, J=7.75 Hz, 1H); 8.02 (d, J=10.51 Hz, 1H); 8.10 (d, J=7.99 Hz, 1H); 8.28 (d, J=6.32 Hz, 2H) Three exchangeable protons.

Example 52 in the Free Form $^1$H NMR: (CDCl$_3$+TFA+CD$_3$OD; 400.13 MHz; δ ppm)
2.78 (s, 3H); 2.92-3.18 (br d, 4H); 3.84 & 3.86 (s, 3H); 3.90-4.03 (br t, 1H); 4.10-4.23 (br d, 1H); 4.45-4.56 (br d, 1H); 7.44-7.57 (m, 3H); 7.60-7.69 (br d, 4H); 7.72 (t, J=7.69 Hz, 1H); 8.02 (d, J=10.42 Hz, 1H); 8.10 (d, J=8.03 Hz, 1H); Two aromatic proton are merged in 8.20-8.70. One exchangeable proton.

Example 53 in the Free Form $^1$H NMR: (CDCl$_3$; 400.13 MHz; δ ppm)
0.93 (d, J=6.63 Hz, 6H); 1.94 (septet, J=6.74 Hz, 1H); 2.40 (s, 3H); 2.57 (d, J=7.17 Hz, 2H); 2.82-2.91 (br t, 2H); 3.16-3.28 (br s, 2H); 3.28-3.38 (br s, 1H); 3.82 (s, 3H); 4.02-4.15 (br s, 2H); 7.33 (d, J=8.08 Hz, 2H); 7.59 (d, J=7.74 Hz, 2H); 8.11 (d, J=8.08 Hz, 2H); 8.19 (d, J=7.90 Hz, 2H); One exchangeable proton

Example 54 in the Free Form $^1$H NMR: (CDCl$_3$; 400.13 MHz; δ ppm)
0.91 (d, J=6.55 Hz, 6H); 1.90 (septet, J=6.75 Hz, 1H); 2.35 (s, 3H); 2.53 (d, J=7.14 Hz, 2H); 2.71-2.88 (br m, 4H); 3.55-3.65 (br m, 1H); 3.77 (s, 3H); 3.89 (s, 2H); 7.28 (d, J=8.20 Hz, 2H); 7.56 (d, J=8.07 Hz, 2H); 8.06 (d, J=8.14 Hz, 2H); 8.13 (d, J=8.11 Hz, 2H); One exchangeable proton.

Example 55 as HCl $^1$H NMR: (CDCl$_3$+CD$_3$OD+TFA; 400.13 MHz; δ ppm)
0.94 (d, J=6.60 Hz, 6H); 1.89-1.99 (m, 2H); 2.27-2.52 (m, 4H); 2.59 (d, J=7.18 Hz, 2H); 2.59-2.65 (m, 1H); 3.72-3.83 (m, 1H); 4.26 (s, 2H); 7.36 (d, J=8.14 Hz, 2H); 7.60 (d, J=8.18 Hz, 2H); 8.12 (d, J=8.16 Hz, 2H); 8.22 (d, J=8.14 Hz, 2H) Four exchangeable protons.

Example 56 as HCl $^1$H NMR: (CDCl3+TFA+DMSO-d$_6$+D$_2$O; 400.13 MHz; δ ppm)
0.23-0.29 (m, 2H); 0.56-0.63 (m, 2H); 1.00-1.08 (m, 1H); 1.59-2.00 (m, 1H); 2.21-2.35 (m, 3H); 2.39-2.50 (m, 2H); 2.66 (d, J=6.96 Hz, 2H); 3.68-3.78 (m, 1H); 4.23 (s, 2H); 7.47 (d, J=8.20 Hz, 2H); 7.60 (d, J=8.15 Hz, 2H); 8.13 (d, J=8.20 Hz, 2H); 8.22 (d, J=8.15 Hz, 2H) Four exchangeable protons.

Example 57 in the Free Form

¹H NMR: (CDCl₃+CD₃OD+TFA; 400.13 MHz; δ ppm)
0.95 (d, J=6.58 Hz, 6H); 1.64-1.80 (br m, 4H); 1.94 (septet, J=6.72 Hz, 1H); 2.12-2.18 (br d, 2H); 2.50-2.57 (br d, 2H); 2.58 (d, J=7.19 Hz, 2H); 3.06-3.16 (br m, 1H); 4.22 (s, 2H); 7.35 (d, J=8.12 Hz, 2H); 7.58 (d, J=8.15 Hz, 2H); 8.11 (d, J=8.12 Hz, 2H); 8.19 (d, J=8.16 Hz, 2H) Three exchangeable protons.

Example 58 in the Free Form

¹H NMR: (CDCl₃; 400.13 MHz; δ ppm)
1.63-1.80 (br m, 4H); 2.15 (d, J=9.60 Hz, 2H); 2.53 (d, J=10.84 Hz, 2H); 3.04-3.14 (br m, 1H); 4.23 (s, 2H); 7.42-7.54 (m, 3H); 7.57-7.64 (br m, 4H); 7.67 (t, J=7.85 Hz, 1H); 8.01 (d, J=10.63 Hz, 1H); 8.08 (d, J=8.15 Hz, 1H); 8.23 (d, J=8.10 Hz, 2H) Three exchangeable protons.

Example 59 in the Free Form

¹H NMR: (CDCl₃+CD₃OD+TFA; 400.13 MHz; δ ppm)
1.68-1.90 (br t, 4H); 2.07-2.24 (br d, 2H); 2.53-2.64 (br s, 2H); 2.71 (s, 3H); 3.28-3.38 (br s, 1H); 4.18 (d, J=12.51 Hz, 1H); 4.45 (d, J=12.85 Hz, 1H); 7.42-7.54 (m, 3H); 7.57-7.63 (br m, 4H); 7.66 (t, J=7.81 Hz, 1H); 8.01 (d, J=11.40 Hz, 1H); 8.07 (d, J=8.17 Hz, 1H); 8.25 (d, J=7.90 Hz, 2H) Two exchangeable protons.

Preparation of Intermediates

Preparation of 2-fluorobiphenyl-4-carboxylic acid

Scheme:

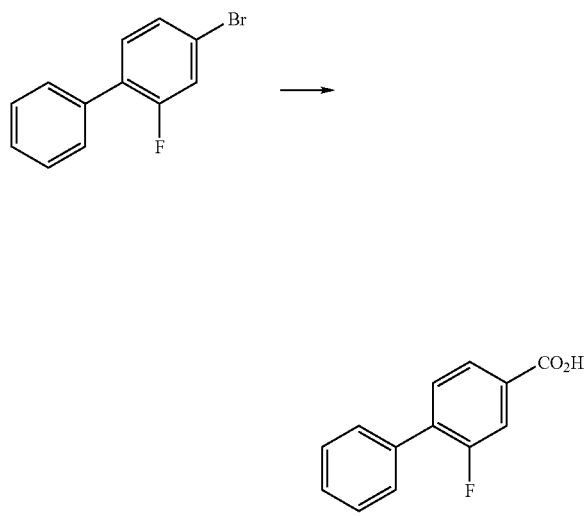

Few crystals of iodine are added to tetrahydrofuran (1400 mL) containing magnesium turnings (25.17 g, 1.035 mol). The mixture is heated at 60-70° C. A solution of 4-bromo-2-fluorobiphenyl (200 g, 0.797 mol) in tetrahydrofuran (600 mL) is added dropwise to the reaction mixture and refluxed for 1 hr. Reaction mixture is brought to room temperature and then cooled to −20° C. Carbon dioxide gas is passed through the reaction mixture for 45 minutes. The reaction mixture is treated with 3N HCl (500 mL) and extracted with ethyl acetate (2×500 mL). Combined organic layer is dried over sodium sulphate. Removal of solvent under reduced pressure gives a solid which is washed with diethyl ether (2×200 mL) and then dried to furnish 2-fluorobiphenyl-4-carboxylic acid.

Preparation of the 4-(5-substituted-1,2,4-oxadiazol-3-yl)phenylmethanol derivatives Preparation of 4-[5-(2-fluorobiphenyl-4-yl)-1,2,4-oxadiazol-3-yl]phenylmethanol

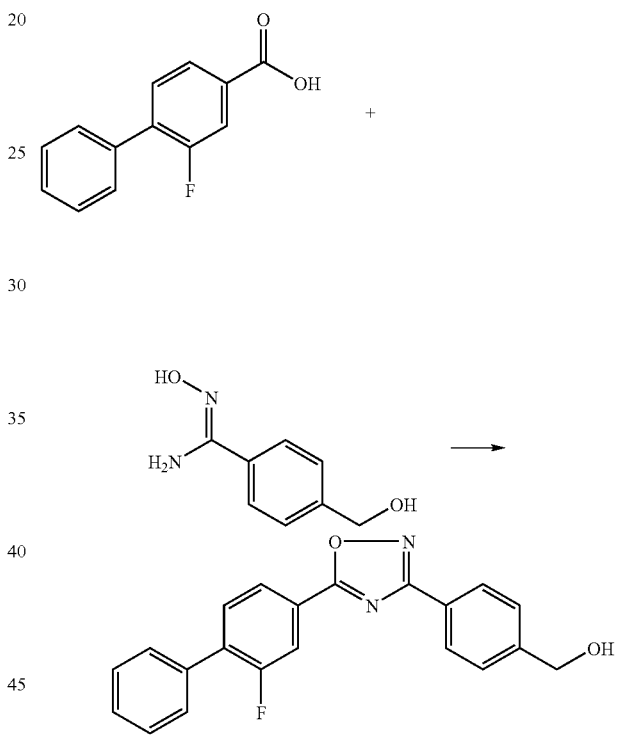

100 g of 2-fluorobiphenyl-4-carboxylic acid, 93 g of N-hydroxy-4-hydroxymethylbenz-amidine, 85 g of N-hydroxybenzotriazole, 115 g of N,N'-dicyclohexylcarbodiimide are introduced into a round bottomed flask containing 800 mL of N,N-dimethylformamide. The reaction mixture is heated under stirring to 130-140° C. for 2-3 hrs, then cooled back to 20-25° C., filtered and washed with 500 mL dichloromethane. The filtrate is evaporated under vacuum. To the resultant thick slurry are added 200 mL isopropyl alcohol and 800 mL demineralized water under stirring at room temperature. The slurry is filtered and washed with 1000 mL demineralized water.

The solid is added to a round bottomed flask containing 500 mL cyclohexane. The resultant slurry is stirred at room temperature for 10-15 mins and filtered, washed with 500+300 mL of cyclohexane and dried by suction. The product is then dried at 40-50° C. to yield 4-[5-(2-fluorobiphenyl-4-yl)[1,2,4]oxadiazol-3-yl]phenyl}-methanol.

The above crude product is purified from ethyl acetate and dichloromethane mixture.

Alternative procedure of preparing 4-[5-(2-fluoro biphenyl-4-yl)-[1,2,4]oxadiazol-3-yl] phenyl}methanol Scheme

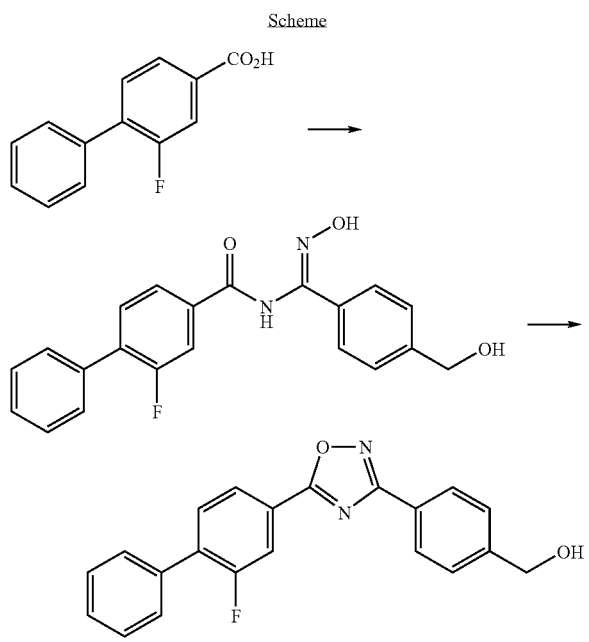

Triethylamine (52 mL, 0.373 mol) is added to a stirred solution of 2-fluorobiphenyl-4-carboxylic acid (40 g, 0.185 mol) in tetrahydrofuran (800 mL). The reaction mixture is cooled to 5-15° C., iso-butyl chloroformate (36.5 mL, 0.28 mol) is added over a period of 20 minutes and stirred for 2 hrs at 15-20° C. A solution of N-hydroxy-4-hydroxymethylbenzamidine (36.9 g, 0.22 mol) in tetrahydrofuran (400 mL) is added to the reaction mixture and stirred for 2 hrs at 20-25° C. The reaction mixture is concentrated under reduced pressure, demineralized water (400 mL) is added to the residue and stirred for one hour at 5-10° C. The slurry is filtered, washed with demineralized water (400 mL) and dried under reduced pressure. The solid is stirred in 5% aqueous sodium bicarbonate solution (600 mL), filtered, washed with demineralized water and dried under reduced pressure. Finally the solid is washed with cyclohexane (600 mL) and dried under reduced pressure at 40-50° C. to give 2-fluorobiphenyl-4-carboxylic acid [hydroxyimino(4-hydroxy-methylphenyl)methyl] amide.

p-Toluenesulfonic acid (0.6 g) is added to a stirred solution of 2-fluoro-biphenyl-4-carboxylic acid [hydroxyimino(4-hydroxymethylphenyl)methyl]amide (60 g, 0.164 mol) in a mixture of toluene and N,N-dimethylacetamide (10:1, 660 mL) and heated at 105-115° C. for 2-3 hrs. Iso-Propyl alcohol (240 mL) is added to the reaction mixture which is then concentrated under reduced pressure. The residue is suspended in a mixture of iso-propyl alcohol and demineralized water (1:3, 1200 mL), cooled to 10-15° C., filtered and was held with demineralized water (600 mL). The solid is dried under reduced pressure at 50-60° C. to yield 4-[5-(2-fluoro-biphenyl-4-yl)[1,2,4]oxadiazol-3-yl]phenyl}methanol.

Preparation of Dicarboxylic Acid Ester Derivatives

Preparation of 1-{-4-[5-(2-fluorobiphenyl-4-yl)-1,2, 4-oxadiazol-3-yl]benzyl}piperidine-4,4-dicarboxylic acid mono (2,2-dimethylpropionyl-oxymethyl)ester Step-I Scheme

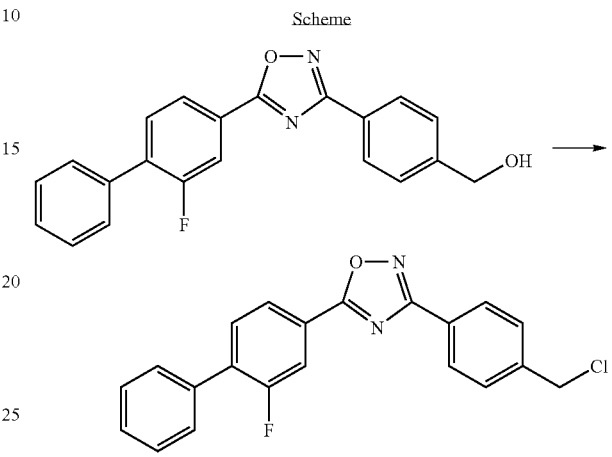

Thionyl chloride (20 mL, 0.274 mol) and N,N-dimethylformamide (2 mL) are added to a stirred solution of 4-[5-(2-fluorobiphenyl-4-yl)-1,2,4-oxadiazole-3-yl]phenylmethanol (32 g, 0.092 mol) in dichloromethane (150 mL) at 0° C. The reaction mixture is heated at 80° C. for 1 hour and then concentrated under reduced pressure. The residue is neutralized with a saturated aqueous sodium bicarbonate solution (150 mL) to furnish a solid which is filtered and washed with n-hexane (150 mL) to give 3-(4-chloromethylphenyl)-5-(2-fluorobiphenyl-4-yl)-1,2,4-oxadiazole.

Step-II

Scheme

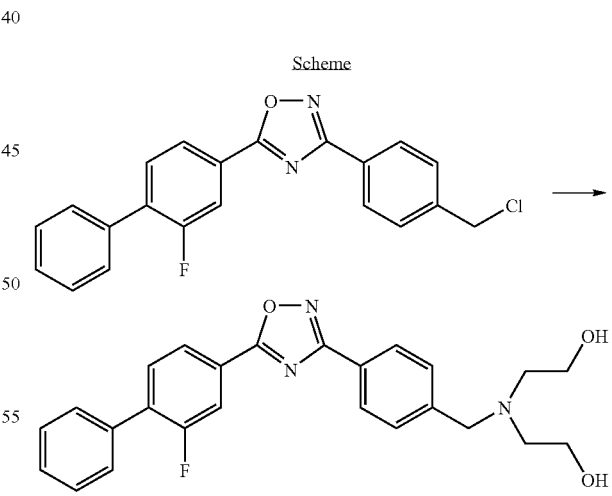

Diisopropylethylamine (23.5 mL, 0.136 mol) and diethanolamine (14.2 g, 0.135 mol) are added to a stirred solution of 3-(4-chloromethylphenyl)-5-(2-fluorobiphenyl-4-yl)-1,2,4-oxadiazole (33 g, 0.090 mol) in N,N-dimethyl-formamide (200 mL). The reaction mixture is heated at 90° C. for 2.5 hrs, the solvent is removed under reduced pressure and the residue is treated with demineralized water (200 mL) to get a solid which is filtered and washed with n-hexane (150 mL) and diethyl ether (100 mL) to furnish 2-[{4-[5-(2-fluorobiphenyl-4-yl)-1,2,4-oxadiazole-3-yl]benzyl}(2-hydroxyethyl)amino]ethanol.

Step-III

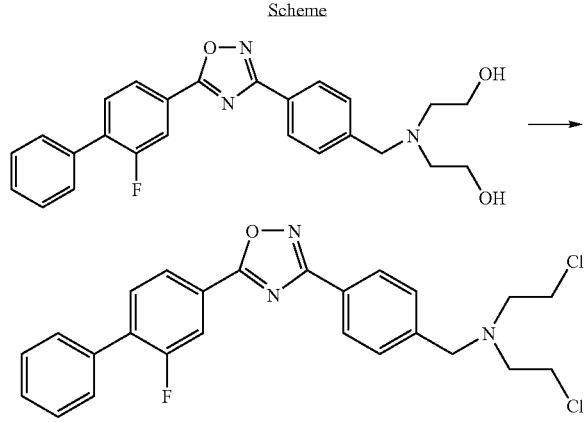

Scheme

Thionyl chloride (52 mL, 0.716 mol) is added drop wise to a stirred solution of 2-[{4-[5-(2-fluoro-biphenyl-4-yl)-1,2,4-oxadiazole-3-yl]benzyl}(2-hydroxyethyl)-amino]ethanol (31 g, 0.0715 mol) in dichloromethane (150 mL) at 0° C. N,N-Dimethylformamide (2 mL) is added and the reaction mixture is heated at 80° C. for 1 h. Excess thionyl chloride is removed under reduced pressure and the residue is made alkaline (pH ~9) by the addition of an aqueous sodium hydroxide solution (4N, 150 mL) at room temperature. The aqueous layer is extracted with ethyl acetate (2×100 mL) and combined organic layers are dried over sodium sulphate. Removal of solvent under reduced pressure gives a viscous liquid, which is purified by column chromatography (silica gel 230-400 mesh, n-hexane:ethyl acetate 7:3) to give bis-(2-chloroethyl){4-[5-(2-fluorobiphenyl-4-yl)-1,2,4-oxadiazole-3-yl]benzyl}amine.

Step-IV

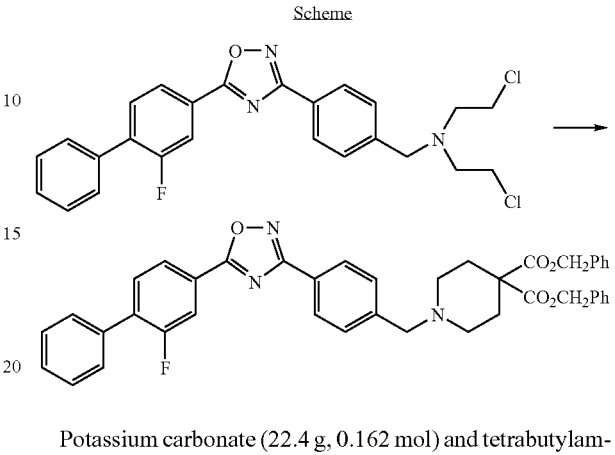

Scheme

Potassium carbonate (22.4 g, 0.162 mol) and tetrabutylammonium bromide (30.5 g, 0.095 mol) are added to a stirred solution of bis-(2-chloroethyl){4-[5-(2-fluorobiphenyl-4-yl)-1,2,4-oxadiazole-3-yl]benzylamine (28 g, 0.059 mol) and dibenzyl malonate (15.3 g, 0.054 mol) in N,N-dimethylformamide (250 mL). The reaction mixture is heated at 100° C. for 4 hrs and concentrated under reduced pressure. The residue is treated with demineralized water (200 mL) followed by brine (25 mL) and the aqueous layer is extracted with tetrahydrofuran (2×150 mL). Combined organic layers are dried over sodium sulphate and concentrated under reduced pressure to give a viscous liquid, which is purified by column chromatography (silica gel 230-400 mesh, n-hexane:ethyl acetate 70:30) to give 1-{4-[5-(2-fluoro-biphenyl-4-yl)-1,2,4-oxadiazole-3-yl]benzyl}piperidine-4,4-dicarboxylic acid dibenzyl ester.

Step-V

Scheme

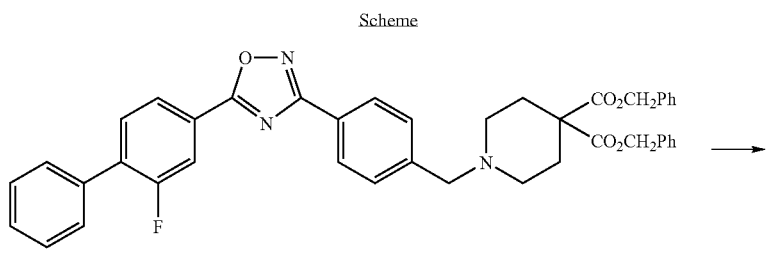

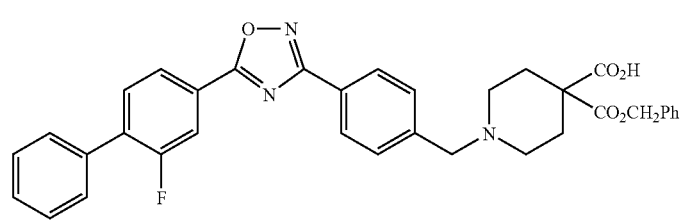

An aqueous solution (50 mL) of sodium hydroxide (1.7 g, 0.043 mol) is added to a stirred solution of 1-{4-[5-(2-fluorobiphenyl-4-yl)-1,2,4-oxadiazole-3-yl]benzyl}piperidine-4,4-dicarboxylic acid dibenzyl ester (18.3 g, 0.027 mol) in tetrahydrofuran (150 mL). The reaction mixture is stirred overnight at room temperature and then concentrated under reduced pressure. The residue is acidified to pH ~6 with diluted hydrochloric acid to give a solid which is filtered and washed with diethylether (100 mL) to furnish 1-{4-[5-(2-fluorobiphenyl-4-yl)-1,2,4-oxadiazole-3-yl]benzyl}piperidine-4,4-dicarboxylic acid mono benzyl ester.

Preparation of 1-{4-[5-(2-fluoro-biphenyl-4-yl)-[1,2,4]oxadiazol-3-yl]-benzyl}-piperidine-4,4-dicarboxylic acid (2-oxo-3,3-dimethylbutyl)ester Step-I Scheme

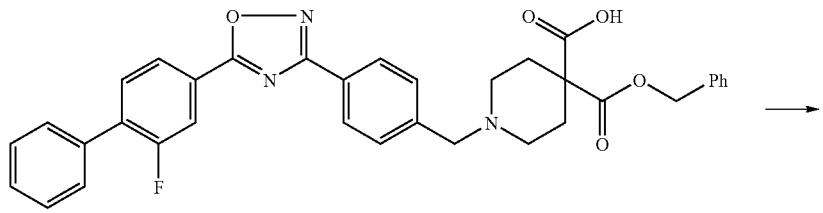

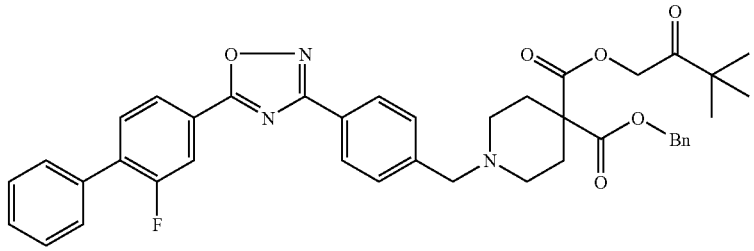

50 mL N,N-dimethylformamide, 5 g of 1-{4-[5-(2-fluoro-biphenyl-4-yl)[1,2,4]oxadiazol-3-yl]benzyl}piperidine-4,4-dicarboxylic acid benzyl ester, 1.8 g of anhydrous potassium carbonate and 2.3 mL of 1-bromo-3,3-dimethylbutan-2-one are added into a 3 neck round bottomed flask. The reaction mixture is heated to 55-60° C. and stirred for 20-60 min. After completion of reaction, the mixture is cooled to 25-30° C. and 100 mL of ice water are added. The slurry is stirred at 25-30° C. for about 30 min and filtered. The product is washed with 50 mL demineralized water, then by 20 mL isopropyl alcohol and suck dried for about 30 mins. Finally the product is dried at 35-40° C. under vacuum to yield 1-{4-[5-(2-fluorobiphenyl-4-yl)[1,2,4]oxadiazol-3-yl]benzyl}piperidine-4,4-dicarboxylic acid benzyl ester 3,3-dimethyl-2-oxobutyl ester.

Step-II

Scheme

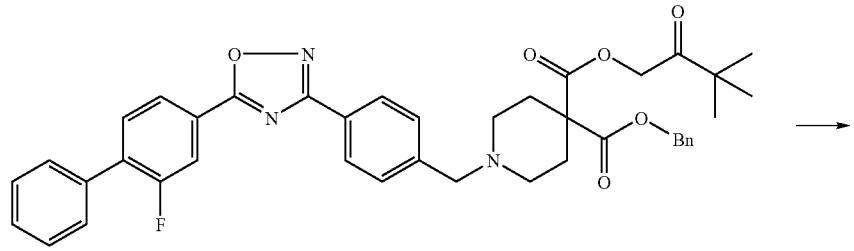

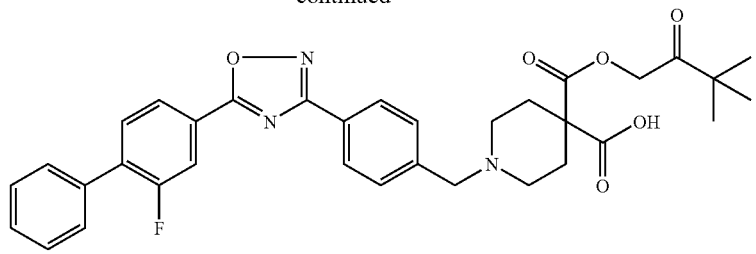

2 g of 1-{4-[5-(2-fluorobiphenyl-4-yl)[1,2,4]oxadiazol-3-yl]benzyl}piperidine-4,4-dicarboxylic acid benzyl ester 3,3-dimethyl-2-oxobutyl ester are added into round bottomed flask containing a solvent mixture of ethyl acetate/tetrahydrofuran [1/0.5] and stirred at room temperature to get a clear solution. Then 40 mL of ethanol are added followed by 0.6 g Pd/CaCO₃. The mixture is stirred under hydrogen gas. After 30 mins 0.2 g of Pd/CaCO₃ are added to the above reaction mixture and stirring under hydrogen is continued. Once the reaction gets completed 4 g of silica gel are added and the mixture stirred at RT for 10 mins, cooled to 0-5° C. and stirred for 20-30 mins. The slurry is filtered and washed with 40 mL ethyl acetate. The product along with Pd/CaCO₃ on the funnel was leached with 200 mL, then 250 mL of a dichloromethane/methanol [2:1] mixture at RT and filtered. The product containing filtrate is concentrated and dried under vacuum at 35-40° C. to yield 1-{4-[5-(2-fluorobiphenyl-4-yl)[1,2,4]oxadiazol-3-yl]benzyl}-piperidine-4,4-dicarboxylic acid (3,3-dimethyl-2-oxobutyl)ester (62).

The following salts were also prepared according to conventional methods starting from the free form of example 62:

N-methylglucamine

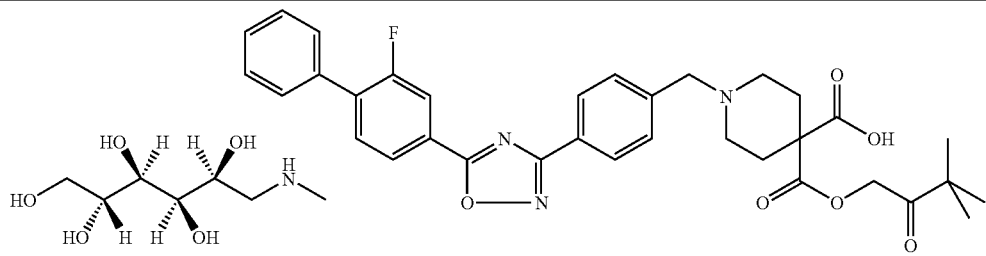

tris

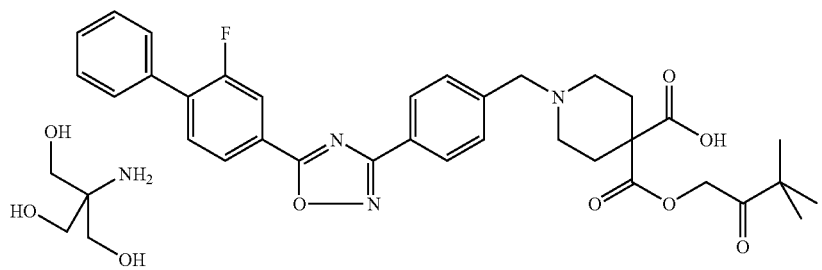 [SMILES: NC(CO)(CO)CO ; CC(C)(C)C(=O)COC(=O)C1(C(=O)O)CCN(Cc2ccc(-c3noc(-c4ccc(-c5ccccc5)c(F)c4)n3)cc2)CC1]

Arginine

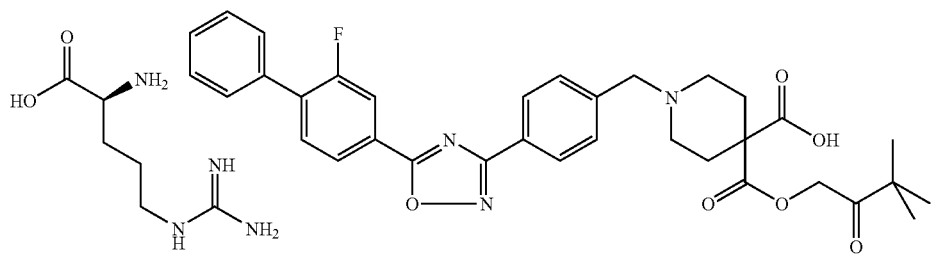

-continued
Lysine
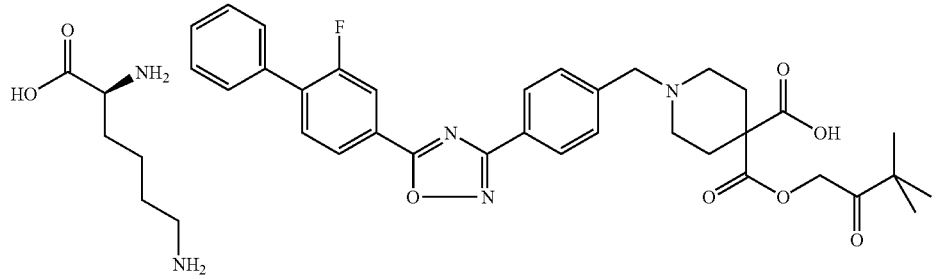
Erbumine
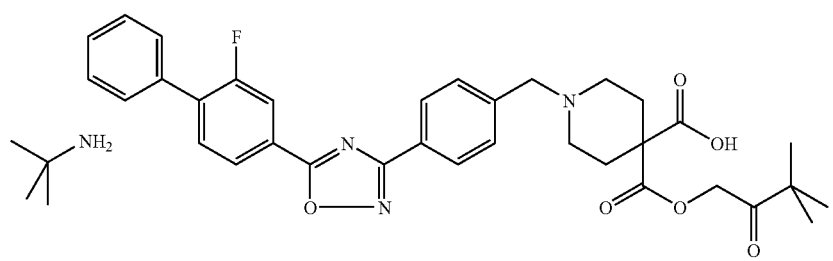
Sodium
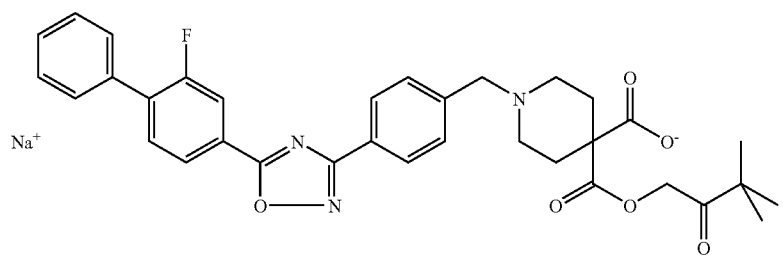
Potassium
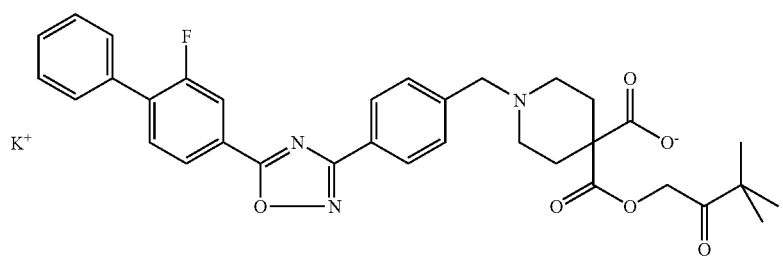 [SMILES: [K+] ; CC(C)(C)C(=O)COC(=O)C1(C(=O)[O-])CCN(Cc2ccc(-c3noc(-c4ccc(-c5ccccc5)c(F)c4)n3)cc2)CC1]
Lithium
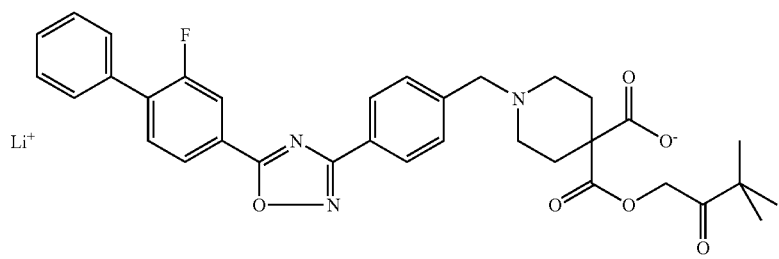 [SMILES: [Li+] ; CC(C)(C)C(=O)COC(=O)C1(C(=O)[O-])CCN(Cc2ccc(-c3noc(-c4ccc(-c5ccccc5)c(F)c4)n3)cc2)CC1]

Examples 60, 61 and 63-90 are prepared in a similar manner.
| | Compound 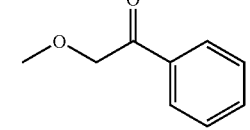 | | | | | | | |
|---|---|---|---|---|---|---|---|---|
| Ex. | R | $R_1$ | $R_2$ | $R_3$ | $R_4$ | $R_5$ | $R_6$ | MS(ES+) |
| 60 | Ph | F | H | H | H | OH | 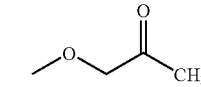 | 620.25 |
| 61 | Ph | F | H | H | H | OH | 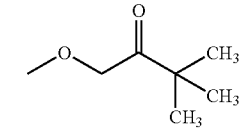 | 558.18 |
| 62 | Ph | F | H | H | H | OH | 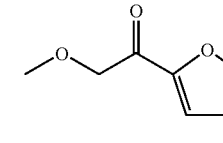 | 600.26 |
| 63 | Ph | F | H | H | H | OH | 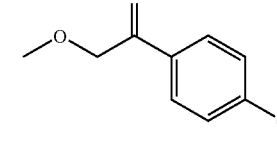 | 609.97 |
| 64 | Ph | F | H | H | H | OH | 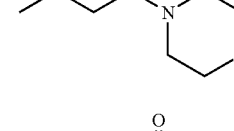 | 654.07 |
| 65 | Ph | F | H | H | H | OH | 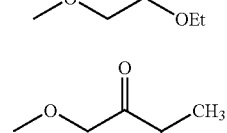 | 615.14 |
| 66 | Ph | F | H | H | H | OH | 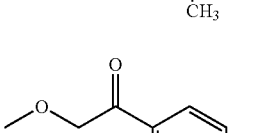 | 588.13 |
| 67 | Ph | F | H | H | H | OH | 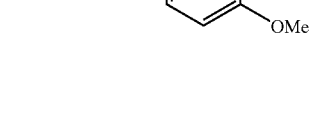 | 586.14 |
| 68 | Ph | F | H | H | H | OH | | 650.10 |

-continued
Compound
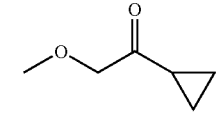
| Ex. | R | R1 | R2 | R3 | R4 | R5 | R6 | MS(ES+) |
|---|---|---|---|---|---|---|---|---|
| 69 | Ph | F | H | H | H | OH | 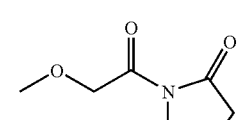 | 584.11 |
| 70 | Ph | F | H | H | H | OH | 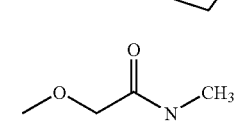 | 627.10 |
| 71 | Ph | F | H | H | H | OH | 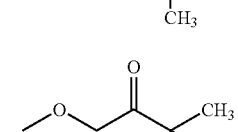 | 587.14 |
| 72 | Ph | F | H | H | H | OCH$_2$Ph | 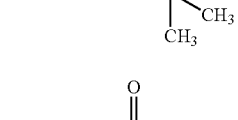 | 690.29 |
| 73 | Ph | F | H | H | H | OCH$_2$Ph | 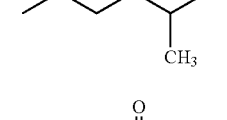 | 676.24 |
| 74 | Ph | F | H | H | H | OH | 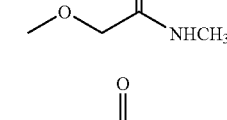 | 573.15 |
| 75 | Ph | F | H | H | H | OH | 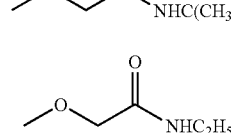 | 615.16 |
| 76 | Ph | F | H | H | H | OH | 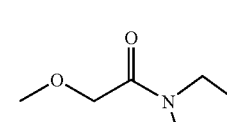 | 587.14 |
| 77 | Ph | F | H | H | H | OH | 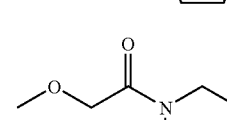 | 613.17 |
| 78 | Ph | F | H | H | H | OH |  | 627.18 |

-continued

Compound

[Structure: R1, R2, R, R3, R4 substituted phenyl connected to 1,2,4-oxadiazole, linked to phenyl-CH2-N-piperidine with COR5 and COR6 substituents]

| Ex. | R | R₁ | R₂ | R₃ | R₄ | R₅ | R₆ | MS(ES⁺) |
|---|---|---|---|---|---|---|---|---|
| 79 | Ph | F | H | H | H | OH | —OCH₂C(O)NHCH(CH₃)₂ | 601.15 |
| 80 | Ph | F | H | H | H | OH | —OCH₂C(O)NH-cyclopropyl | 599.16 |
| 81 | Ph | F | H | H | H | OH | —OCH₂C(O)NH-isobutyl | 615.31 |
| 82 | Ph | F | H | H | H | OH | —OCH₂C(O)NH₂ | 559.26 |
| 83 | Ph | F | H | H | H | OH | —OCH₂C(O)NH-n-butyl | 615.33 |
| 84 | Ph | F | H | H | H | OH | —OCH₂C(O)NH-cyclopentyl | 627.31 |
| 85 | Ph | F | H | H | H | OH | —OCH₂C(O)NH-N-piperidinyl | 642.34 |
| 86 | Ph | F | H | H | H | OH | —OCH₂C(O)NH-cyclohexyl | 641.26 |
| 87 | Ph | F | H | H | H | OH | —OCH₂C(O)NH-cyclobutyl | 613.24 |
| 88 | Ph | F | H | H | H | OH | —OCH₂OC(O)C₃H₇ | 602.10 |
| 89 | Ph | F | H | H | H | OH | —OCH₂C(O)NH-(trans-4-hydroxycyclohexyl) | 655.35 |

-continued

Compound

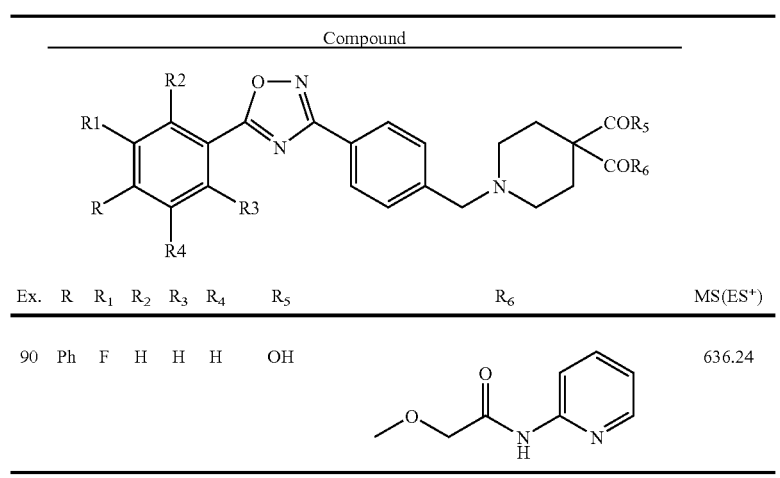

| Ex. | R | $R_1$ | $R_2$ | $R_3$ | $R_4$ | $R_5$ | $R_6$ | MS(ES$^+$) |
|---|---|---|---|---|---|---|---|---|
| 90 | Ph | F | H | H | H | OH | | 636.24 |

$^1$H-NMR Data

Example 60 in the Free Form $^1$H NMR: (Pyridine-d$_5$; 400.13 MHz; δ ppm)
2.70-2.82 (br m, 4H); 2.82-2.93 (br m, 4H); 3.62 (s, 2H); 5.79 (s, 2H); 7.38-7.48 (m, 3H); 7.50-7.55 (br t, 3H); 7.64-7.72 (m, 5H); 8.05-8.09 (br d, 2H); 8.10-8.13 (br d, 1H); 8.13-8.15 (br t, 1H); 8.40-8.45 (br m, 2H) One exchangeable proton.

Example 61 in the Free Form $^1$H NMR: (Pyridine-d$_5$; 400.13 MHz; δ ppm)
2.12 (s, 3H); 2.66-2.73 (br m, 4H); 2.73-2.87 (br m, 4H); 3.58 (s, 2H); 5.02 (s, 2H); 7.43-7.49 (m, 1H); 7.52 (t, J=7.19 Hz, 2H); 7.64-7.73 (br m, 5H); 8.09-8.12 (br d, 1H); 8.13 (s, 1H); 8.41 (d, J=8.12 Hz, 2H) One exchangeable proton.

Example 62 in the Free Form $^1$H NMR: (Pyridine-d$_5$; 400.13 MHz; δ ppm)
1.14 (s, 9H); 2.67-2.81 (br s, 4H); 2.81-2.93 (br m, 4H); 3.59 (s, 2H); 5.2 (s, 2H); 7.43-7.56 (m, 3H); 7.62-7.73 (m, 5H); 8.10-8.15 (m, 2H); 8.41 (d, J=8.05 Hz, 2H) One exchangeable proton.

Example 63 in the Free Form $^1$H NMR: (Pyridine-d$_5$; 400.13 MHz; δ ppm)
2.66-2.81 (br m, 4H); 2.81-2.87 (br t, 4H); 3.60 (s, 2H); 5.57 (s, 2H); 6.49-6.53 (m, 1H); 7.42 (d, J=3.53 Hz, 1H); 7.45-7.50 (br d, 1H); 7.53 (t, J=7.08 Hz, 2H); 7.65-7.74 (m, 5H); 7.78 (d, J=1.33 Hz, 1H); 8.11 (d, J=2.98 Hz, 1H); 8.13 (s, 1H); 8.42 (d, J=8.14 Hz, 2H) One exchangeable proton.

Example 64 in the Free Form $^1$H NMR: (Pyridine-d$_5$; 400.13 MHz; δ ppm)
2.68-2.80 (br m, 4H); 2.80-2.92 (br s, 4H); 3.62 (s, 2H); 5.78 (s, 2H); 7.43-7.48 (br m, 3H); 7.53 (t, J=7.20 Hz, 2H); 7.64-7.75 (br m, 5H); 8.01 (d, J=8.56 Hz, 2H); 8.11 (d, J=4.19 Hz, 1H); 8.13-8.16 (br s, 1H); 8.42 (d, J=8.08 Hz, 2H) One exchangeable proton.

Example 65 in the Free Form $^1$H NMR: (Pyridine-d$_5$; 400.13 MHz; δ ppm)
2.46-2.50 (br t, 4H); 2.60-2.72 (m, 8H); 2.75-2.85 (m, 2H); 3.58 (s, 2H); 3.68 (t, J=4.52 Hz, 4H); 4.48 (t, J=5.66 Hz, 2H); 7.43-7.48 (m, 1H); 7.52 (t, J=7.71 Hz, 2H); 7.64-7.73 (br m, 5H); 8.09-8.12 (br d, 1H); 8.13-8.15 (br t, 1H); 8.42 (d, J=8.15 Hz, 2H) One exchangeable proton.

Example 66 in the Free Form $^1$H NMR: (Pyridine-d$_5$; 400.13 MHz; δ ppm)
1.10 (t, J=7.12 Hz, 3H); 2.63-2.73 (br s, 4H); 2.73-2.87 (br m, 4H); 3.58 (s, 2H); 4.10-4.19 (br q, 2H); 5.00 (s, 2H); 7.42-7.48 (br m, 1H); 7.49-7.55 (br t, 2H); 7.62-7.72 (br m, 5H); 8.08-8.15 (br d, 2H); 8.41 (d, J=7.73 Hz, 2H) One exchangeable proton.

Example 67 in the Free Form $^1$H NMR: (Pyridine-d$_5$; 400.13 MHz; δ ppm)
1.06 (d, J=6.88 Hz, 6H); 2.65-2.75 (br m, 5H); 2.78-2.85 (br t, 4H); 3.58 (s, 2H); 5.12 (s, 2H); 7.44-7.48 (m, 1H); 7.50-7.57 (m, 2H); 7.63-7.74 (m, 5H); 8.08-8.12 (m, 1H); 8.12-8.15 (br t, 1H); 8.41 (d, J=8.18 Hz, 2H) One exchangeable proton.

Example 68 in the Free Form $^1$H NMR: (Pyridine-d$_5$; 400.13 MHz; δ ppm)
2.70-2.95 (br m, 8H); 3.62 (s, 2H); 3.69 (s, 3H); 5.76 (s, 2H); 6.99 (d, J=8.67 Hz, 2H); 7.42-7.49 (m, 1H); 7.52 (t, J=7.53 Hz, 2H); 7.64-7.75 (m, 5H); 8.06-8.17 (m, 4H); 8.42 (d, J=7.94 Hz, 2H) One exchangeable proton Example 69 in the Free Form $^1$H NMR: (Pyridine-d$_5$; 400.13 MHz; δ ppm)
0.76-0.83 (m, 2H); 1.05-1.12 (m, 2H); 1.98-2.06 (m, 1H); 2.66-2.75 (br m, 4H); 2.77-2.85 (br t, 4H); 3.58 (s, 2H); 5.20 (s, 2H); 7.43-7.48 (br m, 1H); 7.52 (t, J=7.72 Hz, 2H); 7.63-7.73 (m, 5H); 8.09-8.13 (br d, 1H); 8.13-8.15 (br s, 1H); 8.41 (d, J=8.14 Hz, 2H) One exchangeable proton

Example 70 in the Free Form

¹H NMR: (Pyridine-d₅; 400.13 MHz; δ ppm)
1.63-1.74 (m, 2H); 2.37 (t, J=8.14 Hz, 2H); 2.68-2.83 (br m, 8H); 3.60 (s, 2H); 3.63 (t, J=7.17 Hz, 2H); 5.60 (s, 2H); 7.43-7.49 (m, 1H); 7.53 (t, J=7.52 Hz, 2H); 7.63-7.73 (m, 5H); 8.11 (d, J=3.53 Hz, 1H); 8.13 (s, 1H); 8.41 (d, J=7.80 Hz, 2H) One exchangeable proton

Example 71 in the Free Form

¹H NMR: (Pyridine-d₅; 400.13 MHz; δ ppm)
2.57-3.03 (br m, 14H); 3.58 (s, 2H); 5.03 (s, 2H); 7.42-7.55 (br d, 2H); 7.56-7.75 (br m, 6H); 8.11 (d, J=9.71 Hz, 2H); 8.40 (d, J=8.00 Hz, 2H) One exchangeable proton

Example 72 in the Free Form

¹H NMR: (CDCl₃; 400.13 MHz; δ ppm)
1.20 (s, 9H); 2.20-2.30 (br m, 4H); 2.43-2.52 (br s, 2H); 2.52-2.62 (br s, 2H); 3.55 (s, 2H); 4.86 (s, 2H); 5.21 (s, 2H); 7.30-7.38 (br m, 5H); 7.42-7.54 (m, 5H); 7.60-7.68 (m, 3H); 8.02 (dd, J₁=10.69 Hz, J₂=1.22 Hz, 1H); 8.08 (dd, J₁=8.23 Hz, J₂=1.52 Hz, 1H); 8.11 (d, J=8.14 Hz, 2H)

Example 73 in the Free Form

¹H NMR: (CDCl₃; 400.13 MHz; δ ppm)
1.12 (d, J=6.92 Hz, 6H); 2.20-2.32 (br m, 4H); 2.45-2.60 (br m, 4H); 2.64 (pentate, J=6.93 Hz, 1H); 3.55 (s, 2H); 4.73 (s, 2H); 5.21 (s, 2H); 7.30-7.39 (br m, 5H); 7.42-7.54 (m, 5H); 7.60-7.68 (m, 3H); 8.02 (dd, J₁=10.67 Hz, J₂=1.25 Hz, 1H); 8.08 (dd, J₁=8.07 Hz, J₂=1.43 Hz, 1H); 8.11 (d, J=8.13 Hz, 2H)

Example 74 in the Free Form

¹H NMR: (Pyridine-d₅; 400.13 MHz; δ ppm)
2.51-2.76 (m, 6H); 2.80-2.92 (br d, 5H); 3.56 (s, 2H); 5.08 (s, 2H); 7.42-7.50 (m, 1H); 7.52 (t, J=7.23 Hz, 2H); 7.62-7.75 (m, 5H); 8.08-8.16 (m, 2H); 8.41 (d, J=7.90 Hz, 2H) Two exchangeable protons

Example 75 in the Free Form

¹H NMR: (CDCl₃+CD₃OD; 400.13 MHz; δ ppm)
1.36 (s, 9H); 2.17-2.30 (br m, 2H); 2.30-2.44 (br m, 4H); 2.98-3.08 (br m, 2H); 4.60 (s, 2H); 7.42-7.58 (m, 5H); 7.59-7.64 (br d, 3H); 7.67 (t, J=7.79 Hz, 1H); 8.01 (d, J=10.64 Hz, 1H); 8.07 (dd, J₁=7.87 Hz, J₂=0.83 Hz, 1H); 8.16 (d, J=8.02 Hz, 2H) Two protons are merged between 3.70-3.83; One exchangeable proton

Example 76 in the Free Form

¹H NMR: (Pyridine-d₅; 400.13 MHz; δ ppm)
1.09 (t, J=7.22 Hz, 3H); 2.54-2.75 (br m, 6H); 2.83-2.91 (br m, 2H); 3.27-3.46 (m, 2H); 3.57 (s, 2H); 5.09 (s, 2H); 7.43-7.49 (m, 1H); 7.52 (t, J=7.24 Hz, 2H); 7.63-7.72 (m, 5H); 8.09-8.15 (m, 2H); 8.41 (d, J=8.02 Hz, 2H) Two exchangeable protons

Example 77 in the Free Form

¹H NMR: (CDCl₃+CD₃OD+D₂O; 400.13 MHz; δ ppm)
1.83-1.93 (m, 2H); 1.95-2.06 (m, 2H); 2.17-2.29 (br t, 2H); 2.35-2.46 (br d, 2H); 2.72-2.85 (br t, 2H); 2.98-3.11 (br d, 2H); 3.41-3.53 (m, 4H); 3.92 (s, 2H); 4.74 (s, 2H); 7.42-7.54 (m, 3H); 7.56-7.68 (m, 5H); 8.00 (d, J=10.63 Hz, 1H); 8.06 (d, J=8.97 Hz, 1H); 8.14 (d, J=8.11 Hz, 2H) One exchangeable proton

Example 78 in the Free Form

¹H NMR: (Pyridine-d₅; 400.13 MHz; δ ppm)
1.23-1.42 (br s, 6H); 2.68-3.01 (br t, 8H); 3.10-3.25 (br d, 2H); 3.45-3.55 (br s, 2H); 3.58 (s, 2H); 5.70 (s, 2H); 7.41-7.49 (br m, 1H); 7.49-7.55 (m, 2H); 7.61-7.72 (m, 5H); 8.08-8.14 (m, 2H); 8.39 (d, J=7.88 Hz, 2H) One exchangeable proton

Example 79 in the Free Form

¹H NMR: (CDCl₃+CD₃OD+D₂O; 400.13 MHz; δ ppm)
1.12 (d, J=6.58 Hz, 6H); 2.24-2.36 (br t, 2H); 2.36-2.57 (br, 4H); 3.13-3.22 (br d, 2H); 3.93 (s, 2H); 4.01-4.11 (m, 1H); 4.70 (s, 2H); 7.41-7.52 (m, 3H); 7.55 (d, J=8.07 Hz, 2H); 7.58-7.67 (m, 3H); 7.99 (d, J=10.65 Hz, 1H); 8.05 (d, J=9.09 Hz, 1H); 8.16 (d, J=8.09 Hz, 2H); Two exchangeable protons

Example 80 in the Free Form

¹H NMR: (Pyridine-d₅; 400.13 MHz; δ ppm)
0.62-0.67 (br m, 4H); 2.50-2.74 (br m, 6H); 2.80-2.92 (br m, 2H); 2.97-3.05 (br m, 1H); 3.56 (s, 2H); 5.08 (s, 2H); 7.40-7.50 (m, 1H); 7.52 (t, J=7.20 Hz, 2H); 7.62-7.75 (m, 5H); 8.08-8.16 (m, 2H); 8.41 (d, J=8.03 Hz, 2H); 8.62-8.68 (br m, 1H) One exchangeable proton

Example 81 as tert-butyl amine salt

¹H NMR: (CDCl₃+CD₃OD; 400.13 MHz; δ ppm)
0.88 (d, J=6.68 Hz, 6H); 1.32 (s, 9H); 1.75-1.87 (m, 1H); 2.05-2.18 (br m, 4H); 2.26-2.37 (br m, 2H); 2.85-2.94 (br d, 2H); 3.04 (d, J=7.02 Hz, 2H); 3.59 (s, 2H); 4.70 (s, 2H); 7.42-7.55 (m, 5H); 7.60-7.64 (br d, 2H); 7.67 (t, J=7.80 Hz, 1H); 8.02 (dd, J₁=10.64 Hz, J₂=1.08 Hz, 1H); 8.08 (dd, J₁=7.96 Hz, J₂=1.26 Hz, 1H); 8.14 (d, J=8.12 Hz, 2H) Four exchangeable proton

Example 82 as tert-butyl amine salt

¹H NMR: (CDCl₃+CD₃OD; 400.13 MHz; δ ppm)
1.30 (s, 9H); 2.07-2.22 (br m, 4H); 2.27-2.37 (br d, 2H); 2.84-2.97 (br m, 2H); 3.62 (s, 2H); 4.69 (s, 2H); 7.42-7.54 (m, 5H); 7.60-7.64 (br d, 2H); 7.67 (t, J=7.81 Hz, 1H); 8.02 (dd, J₁=10.63 Hz, J₂=1.05 Hz, 1H); 8.08 (dd, J₁=8.12 Hz, J₂=1.31 Hz, 1H); 8.13 (d, J=8.12 Hz, 2H) Five exchangeable proton

Example 83 in the Free Form

¹H NMR: (Pyridine-d₅; 400.13 MHz; δ ppm)
0.75 (t, J=7.29 Hz, 3H); 1.19-1.33 (m, 2H); 1.44-1.56 (m, 2H); 2.50-2.76 (m, 6H); 2.81-2.93 (br d, 2H); 3.37-3.47 (m, 2H); 3.56 (s, 2H); 5.12 (s, 2H); 7.43-7.50 (m, 1H); 7.52 (t, J=7.27 Hz, 2H); 7.62-7.74 (m, 5H); 8.07-8.12 (br d, 1H); 8.12-8.15 (br s, 1H); 8.41 (d, J=7.78 Hz, 2H) Two exchangeable proton

Example 84 in the Free Form

¹H NMR: (Pyridine-d₅; 400.13 MHz; δ ppm)
1.34-1.45 (br m, 2H); 1.50-1.65 (br m, 4H); 1.85-1.97 (br m, 2H); 2.51-2.73 (m, 6H); 2.83-2.92 (br d, 2H); 3.56 (s, 2H); 4.44-4.54 (m, 1H); 5.09 (s, 2H); 7.43-7.50 (m, 1H); 7.53 (t, J=7.20 Hz, 2H); 7.64-7.73 (m, 5H); 8.10-8.13 (br d, 1H); 8.13-8.15 (br s, 1H); 8.29-8.34 (br d, 1H); 8.42 (d, J=8.11 Hz, 2H) One exchangeable proton Example 85 in the Free Form $^1$H NMR: (CDCl$_3$+CD$_3$OD; 400.13 MHz; δ ppm)
1.60-1.77 (br m, 6H); 2.16-2.72 (br m, 6H); 2.68-2.82 (br s, 3H); 2.91-3.06 (br m, 3H); 3.68-3.77 (br s, 2H); 4.71 (s, 2H); 7.42-7.56 (m, 4H); 7.56-7.69 (m, 4H); 8.01 (dd, J$_1$=10.72 Hz, J$_2$=1.06 Hz, 1H); 8.07 (d, J=7.98 Hz, 1H); 8.16 (d, J=7.99 Hz, 2H) Two exchangeable proton Example 86 as tert-butyl amine salt $^1$H NMR: (CDCl$_3$+CD$_3$OD; 400.13 MHz; δ ppm)
1.07-1.20 (m, 2H); 1.26 (s, 9H); 1.28-1.39 (m, 3H); 1.57-1.66 (br d, 1H); 1.68-1.76 (br d, 2H); 1.82-1.90 (br d, 2H); 2.01-2.18 (m, 4H); 2.25-2.34 (br d, 2H); 2.80-2.86 (br d, 2H); 3.56 (s, 2H); 3.67-3.77 (br m, 1H); 4.66 (s, 2H); 7.44-7.55 (m, 5H); 7.60-7.65 (br d, 2H); 7.66 (t, J=7.80 Hz, 1H); 8.00-8.05 (br d, 1H); 8.07-8.11 (br d, 1H); 8.12 (d, J=8.07 Hz, 2H) Four exchangeable protons Example 87 as tert-butyl amine salt $^1$H NMR: (CDCl$_3$+CD$_3$OD; 400.13 MHz; δ ppm)
1.32 (s, 9H); 1.62-1.74 (br m, 2H); 1.96-2.20 (m, 6H); 2.20-2.35 (m, 4H); 2.82-2.91 (br d, 2H); 3.59 (s, 2H); 4.28-4.38 (m, 1H); 4.65 (s, 2H); 7.42-7.55 (m, 5H); 7.60-7.64 (br d, 2H); 7.65 (t, J=7.79 Hz, 1H); 8.01 (d, J=10.36 Hz, 1H); 8.08 (d, J=8.10 Hz, 1H); 8.13 (d, J=8.04 Hz, 2H) Four exchangeable protons Example 88 in the Free Form $^1$H NMR: (Pyridine-d$_5$; 400.13 MHz; δ ppm)
0.82 (t, J=7.37 Hz, 3H); 1.52-1.63 (m, 2H); 2.79 (t, J=5.11 Hz, 2H); 2.52-2.63 (br m, 6H); 2.75-2.83 (br t, 2H); 3.54 (s, 2H); 6.14 (s, 2H); 7.43-7.48 (br m, 1H); 7.53 (t, J=7.66 Hz, 2H); 7.62-7.72 (m, 5H); 8.09-8.14 (br d, 1H); 8.14-8.16 (br s, 1H); 8.41 (d, J=8.16 Hz, 2H) One exchangeable proton Example 89 as tert-butylamine salt $^1$H NMR: (CDCl$_3$+CD$_3$OD; 400.13 MHz; δ ppm)
1.24-1.45 (br s, 13H); 1.85-2.00 (m, 5H); 2.05-2.22 (m, 4H); 2.31 (d, J=11.13 Hz, 2H); 2.82-2.95 (br m, 2H); 3.45-3.55 (br m, 1H); 3.61 (s, 2H); 3.67-3.78 (br m, 1H); 4.67 (s, 2H); 7.42-7.55 (m, 5H); 7.59-7.69 (m, 3H); 8.05 (d, J=10.69 Hz, 1H); 8.08 (d, J=8.03 Hz, 1H); 8.14 (d, J=7.88 Hz, 2H) Four exchangeable protons Example 90 as tert-butylamine salt $^1$H NMR: (CDCl$_3$+CD$_3$OD; 400.13 MHz; δ ppm)
1.23 (s, 9H); 2.08-2.24 (m, 4H); 2.29-2.38 (br d, 2H); 2.82-2.90 (br d, 2H); 3.57 (s, 2H); 4.88 (s, 2H); 7.08 (t, J=5.86 Hz, 1H); 7.42-7.55 (m, 5H); 7.60-7.70 (m, 3H); 7.74 (t, J=8.39 Hz, 1H); 8.02 (d, J=10.68 Hz, 1H); 8.09 (d, J=8.11 Hz, 1H); 8.12 (d, J=8.00 Hz, 2H); 8.18-8.26 (m, 2H) Four exchangeable protons Example 91

Preparation of 1-{4-[5-(2-Fluoro-biphenyl-4-yl)-[1,2,4]oxadiazol-3-yl]-benzyl}-4-(piperidine-1-ylcarbamoyl)-piperidine-4-carboxylic acid ester Step-I Scheme

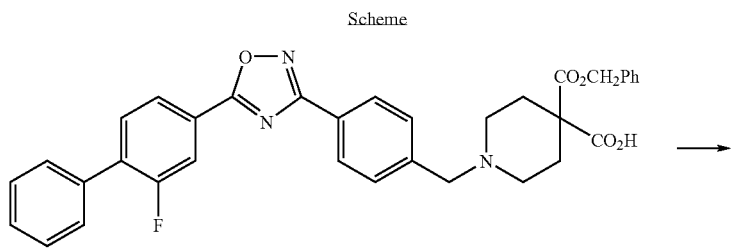

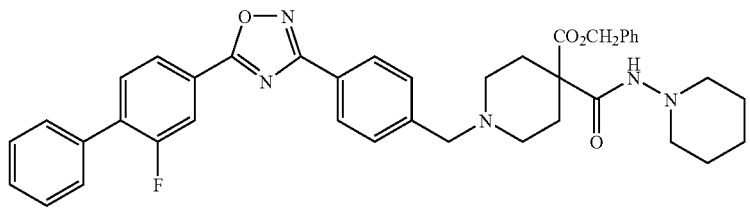

Isobutyl chloroformate (0.158 mL, 0.0012 mol) is added to a solution of 1-{4-[5-(2-fluoro-biphenyl-4-yl)-[1,2,4]oxadiazol-3-yl]-benzyl}-piperidine-4,4-dicarboxylic acid benzyl ester (0.6 g, 0.0010 mol) and N-methyl morpholine (0.156 mL, 0.0015 mol) in tetrahydrofuran (20 mL) at 5° C. The reaction mixture is stirred at 5° C. for 45 minutes. 1-Amino piperidine (0.162 mL, 0.0015 mol) is added to the reaction mixture and is stirred for 30 minutes at 5° C. and then at room temperature for 45 minutes. Demineralized water (10 mL) is added to the reaction mixture, Organic layer is separated and dried over sodium sulphate. Removal of solvent under reduced pressure gives a viscous liquid, which is purified by column chromatography (silica gel 230-400 mesh, hexane: ethyl acetate 70:30) to get 1-{4-[5-(2-fluoro-biphenyl-4-yl)-[1,2,4]oxadiazol-3-yl]-benzyl}-4-(piperidine-1-ylcarbamoyl)-piperidine-4-carboxylic acid benzyl ester.

Step-II

Scheme

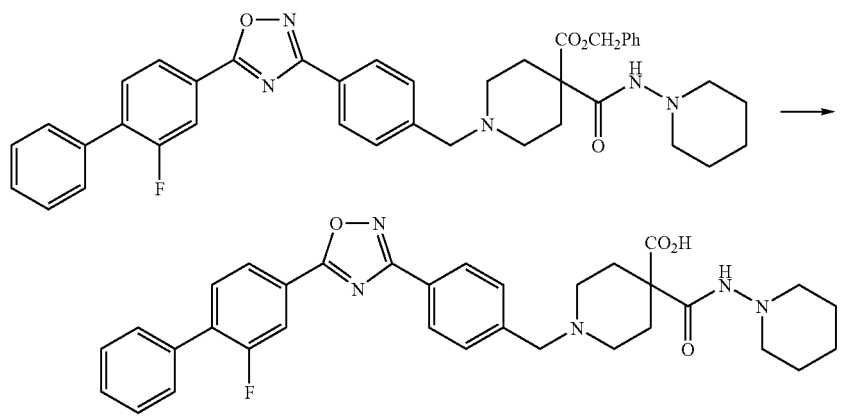

A solution of lithium hydroxide monohydrate (0.031 g, 0.000735 mol) in demineralized water (2 mL) is added to a solution of 1-{4-[5-(2-fluoro-biphenyl-4-yl)-[1,2,4]oxadiazol-3-yl]-benzyl}-4-(piperidine-1-ylcarbamoyl)-piperidine-4-carboxylic acid benzyl ester (0.165 g, 0.000245 mol) in tetrahydrofuran (10 mL). The reaction mixture is heated at 70° C. for 2 hrs. Tetrahydrofuran is removed under reduced pressure and the residue is acidified with 2N HCl (pH ~5). The solid mass thus formed is filtered and washed with acetone (5 mL) to furnish 1-{4-[5-(2-fluoro-biphenyl-4-yl)-[1,2,4]oxadiazol-3-yl]-benzyl}-4-(piperidine-1-ylcarbamoyl)-piperidine-4-carboxylic acid [91, MS (ES$^+$)=584.23].

Following compound (92) is prepared using the same procedure.

| Compound | | MS(ES$^+$) |
|---|---|---|
| 92 | ![structure] | 570.27 |

Example 91 in the Free Form $^1$H NMR: (CDCl$_3$+TFA; 400.13 MHz; δ ppm)
1.46-1.70 (br m, 2H); 1.89-2.16 (br m, 4H); 2.35-2.65 (br s, 4H); 3.16-3.39 (br s, 2H); 3.39-3.55 (br s, 2H); 3.55-3.71 (br s, 2H); 3.75-3.92 (br s, 2H); 4.39 (s, 2H); 7.43-7.54 (m, 4H); 7.54-7.60 (br d, 1H); 7.60-7.66 (br d, 2H); 7.69 (t, J=7.70 Hz, 1H); 8.01 (d, J=10.33 Hz, 1H); 8.08 (d, J=7.91 Hz, 1H); 8.25 (d, J=7.38 Hz, 2H) Two exchangeable protons Example 92 in the Free Form $^1$H NMR (CDCl$_3$+CD$_3$OD+tert-butylamine; 400.13 MHz; δ ppm)

1.77-1.92 (br s, 4H); 1.96-2.23 (br m, 4H); 2.34-2.49 (br s, 2H); 2.54-2.69 (br s, 2H); 2.75-2.93 (br s, 4H); 3.59 (s, 2H); 7.40-7.58 (br m, 5H); 7.58-7.72 (br s, 3H); 7.98-8.18 (br m, 4H); Two exchangeable protons

| Compound |
|---|

Structure: R1, R2, R3, R4, R on phenyl; connected to 1,2,4-oxadiazole, then phenyl-CH2-piperidine with 4,4-(COR5)(COR6)

| Ex. | R | R₁ | R₂ | R₃ | R₄ | R₅ | R₆ | MS(ES⁺) |
|---|---|---|---|---|---|---|---|---|
| 93 | Ph | F | H | H | H | OH | OC₅H₁₁ | 572.17 |
| 94 | Ph | F | H | H | H | OH | O-CH₂CH₂-Ph | 606.12 |
| 95 | Ph | F | H | H | H | OH | OCH₂CF₃ | 584.07 |
| 96 | Ph | F | H | H | H | OH | O-CH₂-(3-methyloxetan-3-yl) | 586.21 |

Example 93 in the Free Form

¹H NMR (Pyridine-d₅; 400.13 MHz; δ ppm)

0.76 (t, J=7.23 Hz, 3H); 1.15-1.35 (m, 4H); 1.58-1.67 (m, 2H); 2.58-2.69 (br m, 6H); 2.75-2.85 (br t, 2H); 3.57 (s, 2H); 4.31 (t, J=6.54 Hz, 2H); 7.43-7.48 (br t, 1H); 7.50-7.55 (br t, 2H); 7.64-7.72 (m, 5H); 8.10-8.12 (br d, 1H); 8.13-8.15 (br t, 1H); 8.42 (d, J=8.16 Hz, 2H) One exchangeable proton Example 94 in the Free Form ¹H NMR: (Pyridine-d₅; 400.13 MHz; δ ppm)

2.45-2.53 (br m, 2H); 2.55-2.62 (br t, 4H); 2.71-2.78 (br m, 2H); 3.01 (t, J=6.81 Hz, 2H); 3.51 (s, 2H); 4.57 (t, J=6.81 Hz, 2H); 7.31 (d, J=3.21 Hz, 2H); 7.32 (s, 2H); 7.42-7.48 (br m, 1H); 7.50-7.55 (m, 2H); 7.64-7.72 (m, 6H); 8.10-8.12 (br d, 1H); 8.13-8.15 (br t, 1H); 8.42 (d, J=8.16 Hz, 2H) One exchangeable proton Example 95 in the Free Form ¹H NMR: (Pyridine-d₅; 400.13 MHz; δ ppm)

2.45-2.56 (br s, 2H); 2.58-2.65 (br s, 4H); 2.79-2.86 (br m, 2H); 3.53 (s, 2H); 5.04 (q, J=8.77 Hz, 2H); 7.43-7.48 (m, 1H); 7.50-7.55 (m, 2H); 7.62-7.72 (m, 5H); 8.09-8.12 (m, 1H); 8.13 (t, J=1.62 Hz, 1H); 8.41 (d, J=8.19 Hz, 2H) One exchangeable proton Example 96 in the Free Form ¹H NMR: (Pyridine-d₅; 400.13 MHz; δ ppm)

1.27 (s, 3H); 2.55-2.69 (br s, 6H); 2.75-2.85 (br d, 2H); 3.57 (s, 2H); 4.33 (d, J=5.80 Hz, 2H); 4.42 (s, 2H); 4.65 (d, J=5.80 Hz, 2H); 7.45-7.49 (m, 1H); 7.50-7.56 (br t, H); 7.64-7.72 (m, 5H); 8.11 (d, J=3.43 Hz, 1H); 8.13 (s, 1H); 8.42 (d, J=8.04 Hz, 2H) One exchangeable proton Preparation of 1-{4-[5-(4-cyclohexylphenyl)-[1,2,4]oxadiazol-3-yl]benzyl}piperidine-3,3-dicarboxylic acid Step-I

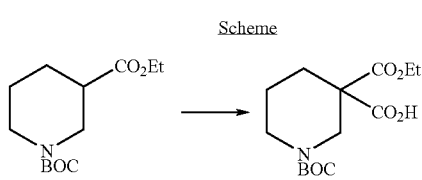

Scheme n-Butyl lithium (2.38 g, 0.0372 mol) is added to a solution of diisopropylamine (5.65 mL, 0.0404 mol) in tetrahydrofuran (60 mL) at −70° C. The reaction mixture is allowed to stirred at −70° C. for 30 minutes. A solution of piperidine-1,3-dicarboxylicacid 1-tert-butyl ester 3-ethyl ester (8 g, 0.031 mol) in tetrahydrofuran (40 mL) is added to the reaction mixture followed by tetramethylene ethylene diamine (12 mL, 1.5 vol) at −70° C. The reaction mixture is allowed to stir at −40° C. for 10 minutes and then carbon dioxide gas is purged through the reaction mixture at −70° C. for 30 minutes. The reaction mixture is quenched with saturated aqueous ammonium chloride solution (40 mL). Organic layer is separated and washed with saturated sodium bicarbonate solution (2×50 mL). The aqueous layer is acidified with 3N HCl to pH ~2 and extracted with ethyl acetate (2×80 mL). Organic layer is separated and dried over sodium sulphate. Removal of solvent under reduced pressure yields piperidine-1,3,3-tricarboxylic acid 1-tert-butyl ester 3-ethyl ester.

Step-II

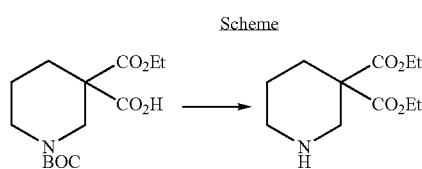

Piperidine-1,3,3-tricarboxylic acid 1-tert-butyl ester 3-ethyl ester (5.2 g, 0.017 mol) is added to a ethanolic hydrochloride (70 mL) solution and heated at reflux for 2.5 hrs. Ethanol is removed under reduced pressure, demineralized water (70 mL) is added to the residue and aqueous layer is washed with diethyl ether (40 mL). Aqueous layer is made basic (pH ~10) with 5N sodium hydroxide solution and extracted with dichloromethane (4×100 mL). Combined organic layer is dried over sodium sulphate and concentrated under reduced pressure to yield piperidine-3,3-dicarboxylic acid diethyl ester.

Step-III

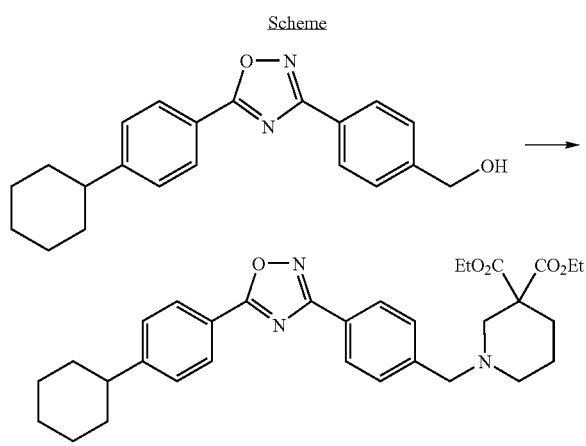

Methanesulfonyl chloride (0.157 mL, 0.0020 mol) is added to a stirred solution of {4-[5-(4-cyclohexyl phenyl)-[1,2,4]oxadiazole-3-yl]-phenyl}-methanol (0.45 g, 0.0013 mol) and triethylamine (0.376 mL, 0.0027 mol) in dichloromethane (10 mL) at 5° C. Reaction mixture is stirred at 5° C. for 30 minutes, then treated with demineralized water (10 mL). Dichloromethane layer is separated and aqueous layer is extracted with dichloromethane (2×15 mL). Combined organic layer is dried over sodium sulphate and concentrated under reduced pressure to yield methanesulfonic acid 4-[5-(4-cyclohexyl-phenyl)[1,2,4]oxadiazol-3-yl]-benzyl ester.

Piperidine-3,3-dicarboxylic acid diethyl ester (0.37 g, 0.0016 mol) is added to a stirred solution containing the above mentioned mesylate derivative (10 mL) and N,N-diisopropylethylamine (0.35 mL, 0.002 mol) in N,N-dimethyl formamide. Reaction mixture is heated at 80° C. for 30 minutes. N,N-Dimethylformamide is removed under reduced pressure, and the crude residue is purified by column chromatography (silica gel 230-400 mesh, n-hexane:ethyl acetate (80:20) to get 1-{4-[5-(4-cyclohexyl-phenyl)-[1,2,4]oxadiazol-3-yl]-benzyl}-piperidine-3,3-dicarboxylic acid diethyl ester Step-IV

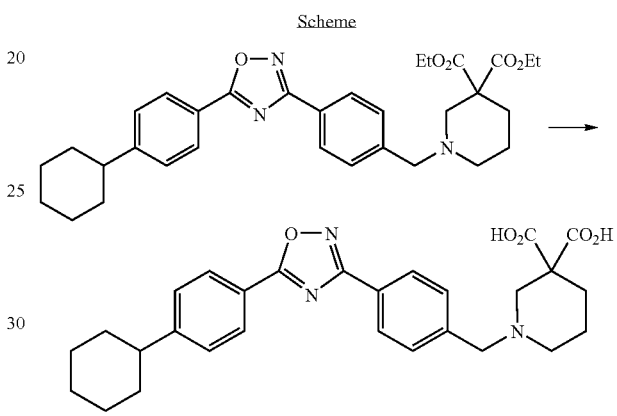

An aqueous solution (4 mL) of sodium hydroxide (0.074 g, 0.0019 mol) is added to a stirred solution of 1-{4-[5-(4-cyclohexyl-phenyl)-[1,2,4]oxadiazol-3-yl]-benzyl}-piperidine-3,3-dicarboxylic acid diethyl ester (0.2 g, 0.0004 mol) in ethanol. Reaction mixture is heated at reflux for 6 hrs. Ethanol is removed under reduced pressure, demineralized water is added to the residue and it is acidified (pH ~2) with 2N HCl solution. White solid mass thus obtained is filtered, washed with dichloromethane (2×3 mL) and dried under reduced pressure to get 1-{4-[5-(4-cyclohexyl-phenyl)-[1,2,4]oxadiazol-3-yl]-benzyl}-piperidine-3,3-dicarboxylic acid hydrochloride (99).

Examples 97, 98 and 100 are prepared in a similar manner.

| Compound |
|---|

| Ex. | R | $R_1$ | $R_2$ | $R_3$ | $R_4$ | $R_5$ | $R_6$ | MS(ES$^+$) |
|---|---|---|---|---|---|---|---|---|
| 97 | Ph | F | H | H | H | OH | OH | 502.14 |
| 98 | CH(CH$_3$)CH$_2$CH$_3$ (isobutyl) | H | H | H | H | OH | OH | — |

-continued

| | Compound | | | | | | | |
|---|---|---|---|---|---|---|---|---|
| Ex. | R | R₁ | R₂ | R₃ | R₄ | R₅ | R₆ | MS(ES⁺) |
| 99 | cyclohexyl | H | H | H | H | OH | OH | 490.19 |
| 100 | Ph | H | H | H | H | OH | OH | 484.12 |

Example 97 as HCl

¹H NMR: (CDCl₃+CD₃OD+TFA; 400.13 MHz; δ ppm)
1.76-1.92 (br s, 1H); 1.95-2.09 (br s, 2H); 2.50-2.65 (br s, 1H); 2.84-3.10 (br m, 2H); 3.64-3.91 (br m, 2H); 4.11-4.29 (br s, 1H); 4.59-4.73 (br s, 1H); 7.43-7.55 (m, 3H); 7.60-7.73 (m, 5H); 8.02 (d, J=10.51 Hz, 1H); 8.08 (d, J=8.08 Hz, 1H); 8.27 (d, J=7.73 Hz, 2H). Three exchangeable protons Example 98 as HCl ¹H NMR: (CDCl₃+CD₃OD+TFA; 400.13 MHz; δ ppm)
0.94 (d, J=6.51 Hz, 6H); 1.90-2.08 (m, 5H); 2.59 (d, J=7.09 Hz, 2H); 2.80-3.09 (br d, 2H); 3.64-3.93 (br m, 2H); 4.10-4.40 (br s, 1H); 4.53-4.73 (br s, 1H); 7.36 (d, J=7.98 Hz, 2H); 7.66 (d, J=7.59 Hz, 2H); 8.12 (d, J=7.96 Hz, 2H); 8.26 (d, J=7.62 Hz, 2H) Three exchangeable protons Example 99 as HCl ¹H NMR: (DMSO-d₆; 400.13 MHz; δ ppm)
1.44-1.52 (m, 4H); 1.54-2.00 (br m, 10H); 2.52-2.56 (br m, 3H); 2.94 (s, 2H); 3.92 (s, 2H); 7.58 (d, J=7.75 Hz, 2H); 7.65 (d, J=7.35 Hz, 2H); 8.06-8.23 (m, 4H) Three exchangeable protons Example 100 as HCl ¹H NMR: (DMSO-d₆; 400.13 MHz; δ ppm)
1.75-1.95 (br d, 4H); 2.70-2.83 (br s, 2H); 2.95 (s, 2H); 3.93 (s, 2H); 7.49-7.56 (br q, 1H); 7.57-7.64 (br t, 2H); 7.67 (d, J=7.33 Hz, 2H); 7.86 (d, J=7.27 Hz, 2H); 8.04 (d, J=7.91 Hz, 2H); 8.16 (d, J=7.66 Hz, 2H); 8.33 (d, J=7.92 Hz, 2H) Three exchangeable protons Preparation of 1-{4-[5-(2-fluorobiphenyl-4-yl)-[1,2,4]oxadiazol-3-yl]benzyl}-4-(morpholine-4-carbonyl)-piperidine-4-carboxylic acid Step-I Scheme

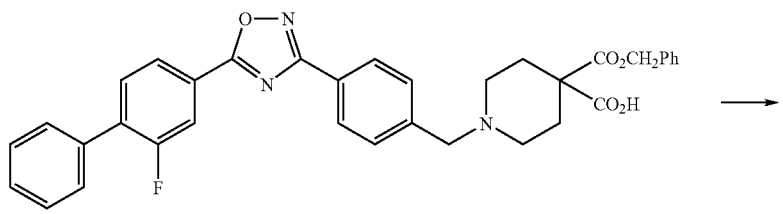

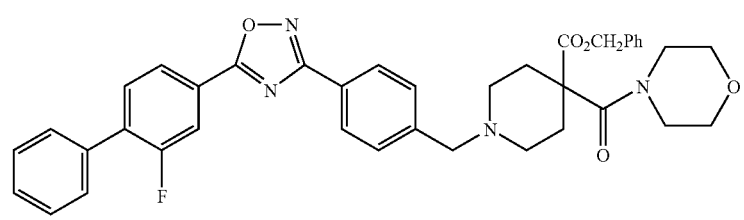

1-Hydroxybenzotriazole (0.183 g, 0.0012 mol) is added to a stirred solution of 1-{4-[5-(2-fluoro-biphenyl-4-yl)-[1,2,4]oxadiazol-3-yl]-benzyl}-piperidine-4,4-dicarboxylic acid benzyl ester (0.6 g, 0.0010 mol) in tetrahydrofuran (20 mL). Reaction mixture is stirred for 30 minutes at room temperature. Morpholine (0.13 mL, 0.0015 mol) and 1-(3-dimethylaminopropyl)-3-ethyl carbodiimide hydrochloride (0.288 g, 0.0015 mol) are added to the reaction mixture and stirred for over night at room temperature. Demineralized water (10 mL) is added to the reaction mixture, tetrahydrofuran layer is separated and the aqueous layer is extracted with ethyl acetate (2×15 mL). Combined organic layer is dried over sodium sulphate and concentrated under reduced pressure to yield a crude viscous liquid, which is purified by column chromatography (silica gel 230-400 mesh, ethyl acetate) to get 1-{4-[5-(2-fluoro-biphenyl-4-yl)-[1,2,4]oxadiazol-3-yl]-benzyl}-4-(morpholine-4-carbonyl)-piperidine-4-carboxylic acid benzyl ester.

Method-A

Step-II

Scheme

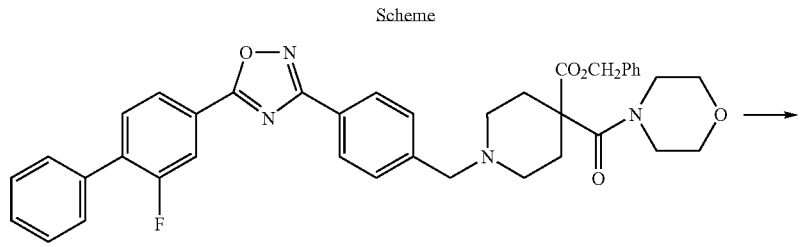

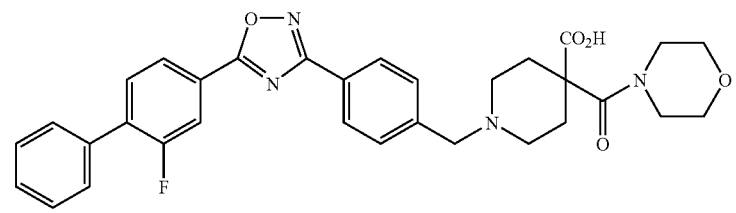

Pd/C (0.13 g) is added to a solution of 1-{4-[5-(2-fluoro-biphenyl-4-yl)-[1,2,4]oxadiazol-3-yl]-benzyl}-4-(morpholine-4-carbonyl)-piperidine-4-carboxylic acid benzyl ester (0.43 g, 0.0006 mol) in a mixture of ethyl acetate:tetrahydrofuran:ethanol (3:2:3, 45 mL). Hydrogen gas is bubbled through the reaction mixture under stirring at room temperature for 2 hrs. The reaction mixture is filtered through a celite bed, washed with MDC:MeOH (80:20, 100 mL) and the filtrate is concentrated under reduced pressure to get solid mass, which is purified by column chromatography (silica gel 230-400 mesh, MDC:MeOH 8:2) to get 1-{4-[5-(2-fluoro-biphenyl-4-yl)-[1,2,4]oxadiazol-3-yl]-benzyl}-4-(morpholine-4-carbonyl)-piperidine-4-carboxylic acid.

Method-B

Preparation of 1-{4-[5-(2-fluorobiphenyl-4-yl)-[1,2,4]oxadiazol-3-yl]benzyl}-4-isopropylcarbamoyl pyridine-4-carboxylic acid

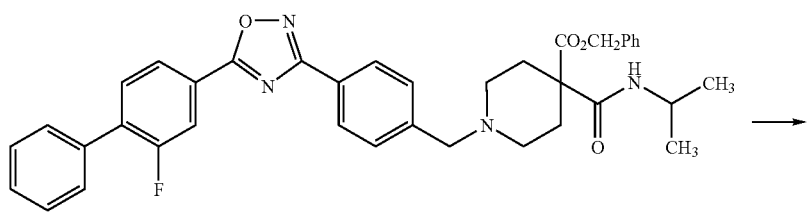

-continued

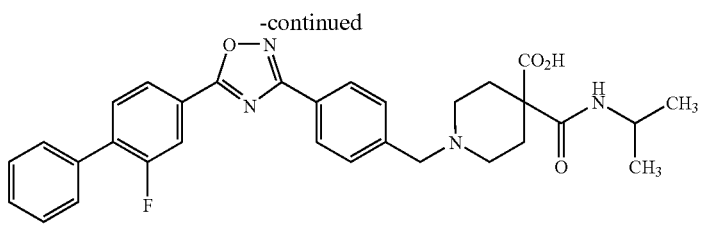

An aqueous solution (2 mL) of lithium hydroxide monohydrate (0.0497 g, 0.00118 mol) is added to the solution of 1-{4-[5-(2-fluoro-biphenyl-4-yl)-[1,2,4]oxadiazol-3-yl]-benzyl}-4-isopropyl carbamoyl-piperidine-4-carboxylic acid ethyl ester (0.3 g, 0.000474 mol) in tetrahydrofuran (10 mL). The reaction mixture is heated for 2 hrs at 70° C., concentrated under reduced pressure and then treated with demineralized water (8 mL). Aqueous layer is acidified to pH ~5 with 2N HCl. The solid thus formed is filtered, washed with ethyl acetate (2×4 mL) and dried under reduced pressure to furnish 1-{4-[5-(2-fluoro-biphenyl-4-yl)-[1,2,4]oxadiazol-3-yl]-benzyl}-4-isopropylcarbamoyl-piperidine-4-carboxylic acid (103).

Following compounds (101, 102 & 104-127) are prepared either by method-A or Method-B.

Compound

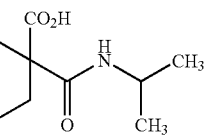

| Ex. | R | $R_1$ | $R_2$ | $R_3$ | $R_4$ | $R_5$ | $R_6$ | MS(ES$^+$) |
|---|---|---|---|---|---|---|---|---|
| 101 | Ph | F | H | H | H | OH | NH-CH2-CH(CH3)2 | 557.23 |
| 102 | Ph | F | H | H | H | OH | NH-CH2CH2-OH | 545.19 |
| 103 | Ph | F | H | H | H | OH | NH-CH(CH3)2 | 543.22 |
| 104 | Ph | F | H | H | H | OH | NH-cyclopropyl | 541.20 |
| 105 | Ph | F | H | H | H | OH | NH-C(CH3)3 | 557.23 |
| 106 | Ph | F | H | H | H | OH | NH-CH2-(1-ethyl-pyrrolidin-2-yl) | 612.26 |
| 107 | Ph | F | H | H | H | OH | NH-CH(CH2OH)2 | 575.21 |

-continued
| | | | | | | | Compound | |
|---|---|---|---|---|---|---|---|---|
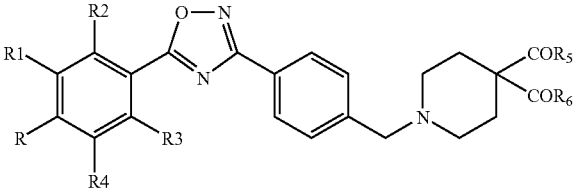
| Ex. | R | R₁ | R₂ | R₃ | R₄ | R₅ | R₆ | MS(ES⁺) |
|---|---|---|---|---|---|---|---|---|
| 108 | Ph | F | H | H | H | OH | 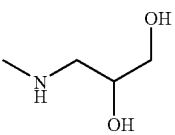 | 575.21 |
| 109 | Ph | F | H | H | H | OH | 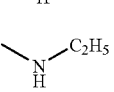 | 515.18 |
| 110 | Ph | F | H | H | H | OH | 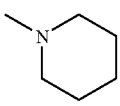 | 529.21 |
| 111 | Ph | F | H | H | H | OH | 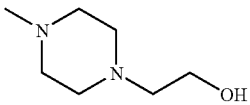 | 569.23 |
| 112 | Ph | F | H | H | H | OH | 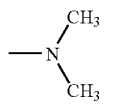 | 614.28 |
| 113 | Ph | F | H | H | H | OH | 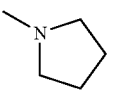 | 529.2 |
| 114 | Ph | F | H | H | H | OH | 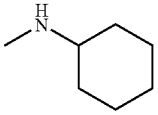 | 555.22 |
| 115 | Ph | F | H | H | H | OH | 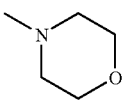 | 583.25 |
| 116 | Ph | F | H | H | H | OH | 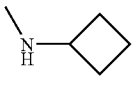 | 571.21 |
| 117 | Ph | F | H | H | H | OH | 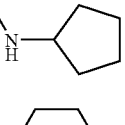 | 555.11 |
| 118 | Ph | F | H | H | H | OH |  | 569.11 |
| 119 | Ph | F | H | H | H | OH |  | 599.08 |

-continued

| Compound |
|---|

Structure: R1-R4 substituted phenyl connected to 1,2,4-oxadiazole, connected to phenyl-CH2-N-piperidine with COR5 and COR6 groups at 4-position.

| Ex. | R | R₁ | R₂ | R₃ | R₄ | R₅ | R₆ | MS(ES⁺) |
|---|---|---|---|---|---|---|---|---|
| 120 | Ph | F | H | H | H | OCH₂Ph | N(CH₃)CH₂CH₂OH | 649.29 |
| 121 | Ph | F | H | H | H | OCH₂Ph | NH-cyclohexyl | 673.32 |
| 122 | Ph | F | H | H | H | OCH₂Ph | N(CH₃)₂ | 619.31 |
| 123 | Ph | F | H | H | H | OCH₂Ph | N(CH₂CH₂OH)₂ | 679.28 |
| 124 | Ph | F | H | H | H | OH | N(CH₃)CH₂CH₂OH | 559.26 |
| 125 | Ph | F | H | H | H | OH | (S)-3-hydroxypyrrolidinyl | 571.24 |
| 126 | Ph | F | H | H | H | OH | 4-methylpiperazinyl-CH₂CH₂-O-CH₂CH₂OH | 658.3 |
| 127 | Ph | F | H | H | H | OH | N(CH₂CH₂OH)₂ | 589.27 |

Example 101 in the Free Form

¹H NMR: (CDCl₃+TFA; 400.13 MHz; δ ppm)
0.87 (d, J=6.60 Hz, 3H); 0.92 (d, J=6.61 Hz, 3H); 1.74-1.88 (m, 1H); 2.33-2.50 (br m, 2H); 2.54-2.71 (br m, 2H); 3.06-3.25 (br m, 3H); 3.30-3.43 (br m, 1H); 3.64-3.80 (br m, 2H); 4.35-4.45 (br s, 2H); 7.43-7.54 (m, 3H); 7.57 (d, J=7.78 Hz, 2H); 7.63 (d, J=8.08 Hz, 2H); 7.69 (t, J=7.67 Hz, 1H); 8.01 (dd, J₁=10.44 Hz, J₂=1.43 Hz, 1H); 8.08 (J₁=8.08 Hz, J₂=1.49 Hz, 1H); 8.25 (d, J=6.85 Hz, 2H); 8.68-8.98 (br d, 1H) One exchangeable proton Example 102 in the Free Form ¹H NMR: (CDCl₃+TFA; 400.13 MHz; δ ppm)
2.32-2.51 (br t, 2H); 2.59-2.75 (br d, 2H); 3.07-3.36 (br m, 2H); 3.47-3.64 (br m, 2H); 3.64-3.82 (br m, 2H); 3.82-3.99 (br m, 2H); 4.34-4.46 (br s, 2H); 7.44-7.55 (m, 3H); 7.57 (d, J=8.08 Hz, 2H); 7.63 (d, J=7.57 Hz, 2H); 7.70 (t, J=7.75 Hz, 1H); 8.01 (d, J=10.50 Hz, 1H); 8.08 (d, J=8.00 Hz, 1H); 8.25 (d, J=8.09 Hz, 2H); 8.68-8.80 (br s, 1H) Two exchangeable protons Example 103 in the Free Form ¹H NMR: (CDCl₃; 400.13 MHz; δ ppm)
1.17 (d, J=5.90 Hz, 6H); 2.30-2.48 (br m, 2H); 2.53-2.70 (br m, 2H); 3.08-3.31 (br m, 2H); 3.62-3.82 (br m, 2H); 3.98-4.13 (br s, 1H); 4.40 (s, 2H); 7.42-7.66 (m, 7H); 7.70 (t, J=7.76 Hz, 1H); 8.01 (d, J=10.52 Hz, 1H); 8.07 (d, J=8.07 Hz, 1H); 8.25 (d, J=6.51 Hz, 2H); 8.72-8.87 (br s, 1H) One exchangeable proton Example 104 in the Free Form ¹H NMR: (CDCl₃+TFA; 400.13 MHz; δ ppm)
0.51-0.68 (br s, 2H); 0.84 (d, J=6.48 Hz, 2H); 2.29-2.48 (br t, 2H); 2.51-2.78 (m, 3H); 3.07-3.47 (br m, 2H); 3.50-3.81 (br m, 2H); 4.40 (s, 2H); 7.42-7.55 (m, 3H); 7.57 (d, J=7.33 Hz, 2H); 7.63 (d, J=7.73 Hz, 2H); 7.70 (t, J=7.75 Hz, 1H); 8.01 (d, J=10.37 Hz, 1H); 8.07 (d, J=7.98 Hz, 1H); 8.24 (d, J=7.34 Hz, 2H); 8.60-8.77 (br s, 1H) One exchangeable proton Example 105 in the Free Form ¹H NMR: (CDCl₃+TFA; 400.13 MHz; δ ppm)
1.34 (s, 9H); 2.25-2.50 (br m, 2H); 2.50-2.71 (br m, 2H); 3.05-3.35 (br m, 2H); 3.61-3.91 (br m, 2H); 4.40 (s, 2H); 7.41-7.79 (m, 8H); 8.01 (d, J=10.58 Hz, 1H); 8.08 (d, J=7.81 Hz, 1H); 8.18.8.35 (br m, 2H); 8.51-8.80 (br s, 1H) One exchangeable proton Example 106 in the Free Form ¹H NMR: (CDCl₃+TFA; 400.13 MHz; δ ppm)
1.34-1.50 (br m, 3H); 1.83-1.99 (br m, 1H); 2.06-2.20 (br m, 2H); 2.20-2.36 (br m, 1H); 2.48-2.75 (br m, 4H); 3.01-3.27 (br m, 4H); 3.28-3.43 (br m, 1H); 3.54-3.88 (br m, 6H); 4.30-4.48 (br s, 2H); 7.44-7.56 (m, 3H); 7.63 (d, J=7.62 Hz, 2H); 7.70 (t, J=7.70 Hz, 3H); 8.01 (d, J=10.33 Hz, 1H); 8.07 (d, J=7.92 Hz, 1H); 8.18-8.28 (br s, 2H); 8.79-8.93 (br s, 1H) One exchangeable proton Example 107 in the Free Form ¹H NMR: (CDCl₃+TFA; 400.13 MHz; δ ppm)
2.35-2.54 (br m, 2H); 2.61-2.77 (br d, 2H); 3.11-3.31 (br m, 2H); 3.66-3.80 (br d, 2H): 3.84-4.07 (br s, 4H); 4.13-4.32 (br s, 1H); 4.36-4.47 (br s, 2H); 7.44-7.56 (m, 3H); 7.58 (d, J=7.89 Hz, 2H); 7.63 (d, J=7.49 Hz, 2H); 7.71 (t, J=7.73 Hz, 1H); 8.01 (d, J=10.35 Hz, 1H); 8.08 (d, J=8.11 Hz, 1H); 8.24 (d, J=7.97 Hz, 2H); 8.53-8.65 (br s, 1H) Three exchangeable protons Example 108 in the Free Form ¹H NMR: (CDCl₃+TFA; 400.13 MHz; δ ppm)
2.25-2.48 (br m, 2H); 2.55-2.73 (br m, 2H); 3.04-3.33 (br m, 2H); 3.39-3.95 (br m, 6H); 3.95-4.18 (br m, 1H); 4.37 (s, 2H); 7.40-7.75 (m, 8H); 7.97-8.10 (m, 2H); 8.20-8.30 (br d, 2H); 8.40-8.79 (br d, 1H) Three exchangeable protons Example 109 in the Free Form ¹H NMR: (CDCl₃+TFA; 200.13 MHz; δ ppm)
2.30-2.80 (br m, 4H); 2.82-3.00 (br d, 3H); 3.10-3.50 (br m, 2H); 3.60-3.90 (br s, 2H); 4.30-4.52 (br s, 2H); 7.12-7.35 (br s, 1H); 7.40-7.80 (m, 8H); 7.99-8.18 (m, 2H); 8.20-8.35 (br s, 2H) One exchangeable proton Example 110 in the Free Form ¹H NMR: (CDCl₃+TFA; 200.13 MHz; δ ppm)
1.16 (t, J=6.96 Hz, 3H); 2.30-2.51 (br m, 2H); 2.58-2.78 (br m, 2H); 3.10-3.48 (br m, 4H); 3.61-3.86 (br m, 2H); 4.33-4.50 (br s, 2H); 7.05-7.18 (br s, 1H); 7.46-7.79 (m, 8H); 7.96-8.13 (m, 2H); 8.18-8.30 (br d, 2H) One exchangeable proton Example 111 in the Free Form ¹H NMR: (CDCl₃+TFA; 400.13 MHz; δ ppm)
1.56-1.76 (m, 6H); 2.38-2.57 (br s, 4H); 3.28-3.47 (br m, 4H); 3.55-3.80 (br m, 4H); 4.39 (s, 2H); 7.43-7.56 (m, 3H); 7.56-7.60 (br d, 2H); 7.62 (d, J=7.74 Hz, 2H); 7.68 (t, J=7.75 Hz, 1H); 8.01 (d, J=10.51 Hz, 1H); 8.08 (d, J=8.05 Hz, 1H); 8.25 (d, J=6.72 Hz, 2H) One exchangeable proton Example 112 in the Free Form ¹H NMR: (CDCl₃+TFA; 400.13 MHz; δ ppm)
2.28-2.70 (br m, 4H); 3.00-3.30 (br s, 2H); 3.37-3.55 (br s, 3H); 3.60-3.75 (br s, 3H); 3.75-3.92 (br s, 3H); 4.10-4.21 (br s, 2H); 4.35-4.50 (br d, 3H); 4.70-4.83 (br s, 2H); 7.44-7.57 (m, 3H); 7.57-7.62 (br m, 2H); 7.63 (d, J=7.54 Hz, 2H); 7.72 (t, J=7.68 Hz, 1H); 8.00 (d, J=1030 Hz, 1H); 8.07 (d, J=7.88 Hz, 1H); 8.23 (d, J=7.08 Hz, 2H) Two exchangeable protons Example 113 in the Free Form ¹H NMR: (CDCl₃+CD₃OD; 400.13 MHz; δ ppm)
2.22-2.40 (br m, 4H); 2.97 (s, 3H); 3.01-3.13 (br s, 5H); 3.30-3.36 (br m, 2H); 4.18 (s, 2H); 7.45-7.55 (m, 3H); 7.59-7.71 (m, 5H); 8.02 (dd, J1=10.66 Hz, J2=1.14 Hz, 1H); 8.08 (dd, J₁=8.15 Hz, J₂=1.28 Hz, 1H); 8.20 (d, J=8.11 Hz, 2H) One exchangeable proton Example 114 in the Free Form ¹H NMR: (CDCl₃+CD₃OD; 400.13 MHz; δ ppm)
1.82-1.99 (br m, 4H); 2.20-2.38 (br s, 4H); 3.02-3.17 (br s, 2H); 3.24-3.36 (br s, 2H); 3.45-3.58 (br m, 4H); 4.18 (s, 2H); 7.44-7.55 (m, 3H); 7.59-7.71 (m, 5H); 8.01 (d, J=10.54 Hz, 1H); 8.08 (dd, J₁=8.37 Hz, J₂=1.19 Hz, 1H); 8.20 (d, J=8.08 Hz, 2H) One exchangeable proton Example 115 in the Free Form ¹H NMR: (CDCl₃+TFA; 400.13 MHz; δ ppm)
1.08-1.45 (br m, 6H); 1.59-1.90 (br m, 4H); 2.29-2.48 (br m, 2H); 2.53-2.71 (br m, 2H); 3.08-3.25 (br s, 1H); 3.28-3.32 (br s, 1H); 3.60-3.80 (br m, 3H); 4.41 (s, 2H); 7.44-7.55 (m, 4H); 7.55-7.66 (m, 3H); 7.70 (t, J=7.62 Hz, 1H); 8.01 (d, J=10.38 Hz, 1H); 8.07 (d, J=8.11 Hz, 1H); 8.20-8.28 (br m, 2H) Two exchangeable protons Example 116 in the Free Form ¹H NMR: (CDCl₃+TFA; 400.13 MHz; δ ppm)
2.35-2.60 (br s, 4H); 3.25-3.41 (br s, 2H); 3.41-3.53 (br s, 2H); 3.64-3.95 (br m, 8H); 4.39 (s, 2H); 7.43-7.54 (m, 4H); 7.54-7.60 (br d, 1H); 7.60-7.65 (br d, 2H); 7.69 (t, J=7.75 Hz, 1H); 8.01 (d, J=10.53 Hz, 1H); 8.07 (d, J=8.03 Hz, 1H); 8.23 (d, J=7.49 Hz, 2H) One exchangeable proton

Example 117 as HCl $^1$H NMR: (CDCl$_3$+TFA; 400.13 MHz; δ ppm)
1.62-1.89 (br m, 2H); 1.89-2.04 (br m, 2H); 2.23-2.49 (br m, 4H); 2.52-2.72 (br t, 2H); 3.09-3.28 (br s, 1H); 3.30-3.42 (br m, 1H); 3.60-3.69 (br d, 1H); 3.69-3.80 (br d, 1H); 4.20-4.35 (br s, 1H); 4.40 (s, 2H); 7.11-7.23 (br m, 1H); 7.42-7.55 (m, 3H); 7.55-7.67 (m, 4H); 7.71 (t, J=7.71 Hz, 1H); 8.01 (d, J=10.30 Hz, 1H); 8.07 (d, J=7.93 Hz, 1H); 8.20-8.27 (br t, 2H); 8.42-8.60 (br m, 1H) One exchangeable proton

Example 118 in the Free Form $^1$H NMR: (CDCl$_3$+TFA; 400.13 MHz; δ ppm)
1.33-1.51 (br m, 2H); 1.51-1.78 (br m, 4H); 1.90-2.09 (br m, 2H); 2.30-2.49 (br m, 2H); 2.49-2.67 (br m, 2H); 3.08-3.24 (br s, 1H); 3.30-3.43 (br s, 1H); 3.59-3.80 (br m, 2H); 4.08-4.20 (br m, 1H); 4.31-4.46 (br s, 2H); 6.88-6.96 (br s, 1H); 7.43-7.54 (m, 3H); 7.55-7.65 (m, 4H); 7.69 (t, J=7.69 Hz, 1H); 8.01 (d, J=10.32 Hz, 1H); 8.07 (d, J=8.06 Hz, 1H); 8.22-8.29 (br t, 2H); 8.79-9.16 (br m, 1H)

Example 119 in the Free Form $^1$H NMR: (CDCl$_3$+TFA+CD$_3$OD; 400.13 MHz; δ ppm)
1.12-1.47 (br m, 4H); 1.79-2.03 (br d, 4H); 2.21-2.56 (br m, 4H); 2.86-3.00 (br t, 1H); 3.02-3.17 (br t, 1H); 3.42-3.73 (br m, 4H); 4.24 (s, 2H); 7.39-7.53 (m, 3H); 7.54-7.69 (m, 5H); 7.99 (t, J=10.38 Hz, 1H); 8.05 (d, J=7.41 Hz, 1H); 8.19-8.27 (br d, 2H) Three exchangeable protons

Example 120 in the Free Form $^1$H NMR: (CDCl$_3$; 400.13 MHz; δ ppm)
2.18-2.25 (br t, 4H); 2.40 (s, 3H); 2.41-2.54 (br m, 4H); 2.78 (t, J=5.33 Hz, 2H); 3.53 (s, 3H); 4.24 (t, J=5.19 Hz, 2H); 5.18 (s, 2H); 7.31-7.39 (m, 4H); 7.44-7.54 (m, 6H); 7.60-7.68 (m, 3H); 8.02 (dd, J$_1$=10.70 Hz, J$_2$=1.48 Hz, 1H); 8.08 (dd, J$_1$=8.07 Hz, J$_2$=1.62 Hz, 1H); 8.11 (d, J=8.19 Hz, 2H)

Example 121 in the Free Form $^1$H NMR: (CDCl$_3$; 400.13 MHz; δ ppm)
0.85-1.02 (br q, 2H); 1.02-1.19 (br m, 1H); 1.22-1.39 (br m, 2H); 1.52-1.69 (br m, 3H); 1.69-1.80 (br d, 2H); 2.03-2.16 (br m, 2H); 2.16-2.28 (br m, 4H); 2.62-2.73 (br m, 2H); 3.50 (s, 2H); 3.62-3.74 (m, 1H); 5.21 (s, 2H); 5.65 (d, J=7.73 Hz, 1H); 7.33-7.38 (br s, 5H); 7.42-7.48 (br d, 3H); 7.48-7.54 (br t, 2H); 7.60-7.68 (m, 3H); 8.02 (d, J=10.69 Hz, 1H); 8.08 (d, J=9.40 Hz, 1H); 8.11 (d, J=8.07 Hz, 2H)

Example 122 in the Free Form $^1$H NMR: (CDCl$_3$; 400.13 MHz; δ ppm)
2.02-2.27 (br m, 5H); 2.46-2.56 (br m, 2H); 2.56-2.72 (br m, 5H); 2.78-2.97 (br s, 2H); 3.54 (s, 2H); 5.18 (s, 2H); 7.31-7.37 (br s, 5H); 7.42-7.53 (m, 5H); 7.59-7.67 (m, 3H); 8.02 (d, J=10.72 Hz, 1H); 8.08 (d, J=9.30 Hz, 1H); 8.11 (d, J=8.05 Hz, 2H)

Example 123 in the Free Form $^1$H NMR: (CDCl$_3$+CD$_3$OD; δ ppm)
2.16-2.34 (br m, 4H); 2.48-2.64 (br s, 4H); 2.90-2.97 (br t, 2H); 3.04-3.13 (br t, 2H); 3.71-3.79 (br t, 2H); 4.34-4.40 (br t, 2H); 5.20 (s, 2H); 6.77 (s, 2H); 7.34-7.42 (m, 4H); 7.55 (m, 6H); 7.62 (d, J=7.72 Hz, 2H); 7.67 (t, J=7.75 Hz, 1H); 8.02 (d, J=10.68 Hz, 1H); 8.08 (d, J=8.04 Hz, 1H); 8.13 (d, J=8.03 Hz, 2H) Two protons are merged between 3.50-3.70. Four exchangeable protons

Example 124 in the Free Form $^1$H NMR: (CDCl$_3$+CD$_3$OD+D$_2$O; 400.13 MHz; δ ppm)
1.21 (s, 9H); 2.05-2.15 (br m, 4H); 2.15-2.25 (br m, 2H); 2.65 (s, 3H); 2.74-2.83 (br s, 2H); 3.17-3.24 (br s, 2H); 3.53 (s, 2H); 4.43-4.51 (br t, 2H); 7.41-7.54 (m, 5H); 7.59-7.68 (m, 3H); 8.01 (d, J=10.66 Hz, 1H); 8.07 (d, J=9.20 Hz, 1H); 8.10 (d, J=8.05 Hz, 2H) Four exchangeable protons

Example 125 as t-butyl amine salt $^1$H NMR: (Pyridine-d$_5$; 400.13 MHz; δ ppm)
1.35 (s, 9H); 1.82-2.11 (br m, 2H); 2.58-2.75 (br s, 4H); 2.79-2.96 (br s, 4H); 3.58 (s, 2H); 3.81-4.18 (br m, 4H); 4.53-4.61 (br s, 1H); 7.42-7.50 (m, 1H); 7.52 (t, J=7.16 Hz, 2H); 7.62-7.74 (m, 5H); 8.09 (d, J=3.94 Hz, 1H); 8.12 (s, 1H); 8.39 (d, J=7.64 Hz, 2H) Four exchangeable protons

Example 126 as t-butyl amine salt $^1$H NMR: (Pyridine-d$_5$; 400.13 MHz; δ ppm)
1.37 (s, 9H); 2.47-2.57 (br m, 6H); 2.57-2.66 (br s, 4H); 2.72-2.84 (br m, 2H); 2.88-3.00 (br m, 2H); 3.56-3.66 (br m, 4H); 3.69 (t, J=4.92 Hz, 2H); 3.81-3.91 (br s, 4H); 3.96 (t, J=4.82 Hz, 2H); 7.44-7.50 (m, 1H); 7.52 (t, J=7.18 Hz, 2H); 7.61-7.75 (m, 5H); 8.10 (d, J=3.82 Hz, 1H); 8.12 (s, 1H); 8.40 (d, J=7.95 Hz, 2H) Four exchangeable protons.

Example 127 as t-butyl amine salt $^1$H NMR: (Pyridine-d$_5$; 400.13 MHz; δ ppm) 1.30 (s, 9H); 2.37-2.48 (br m, 2H);
2.60-2.74 (br s, 4H); 2.87-2.97 (br m, 2H); 3.08-3.15 (br t, 2H); 3.24-3.31 (br t, 2H); 3.53 (s, 2H); 3.97-4.04 (br t, 2H); 4.62-4.68 (br t, 2H); 7.43-7.49 (m, 1H); 7.52 (t, J=7.14 Hz, 2H); 7.62-7.72 (m, 5H); 8.10 (d, J=3.83 Hz, 1H); 8.12 (s, 1H); 8.38 (d, J=8.00 Hz, 2H) Five exchangeable protons The following compounds were also prepared:

| Example | Compound | MS(ES$^+$) |
|---|---|---|
| 128 | 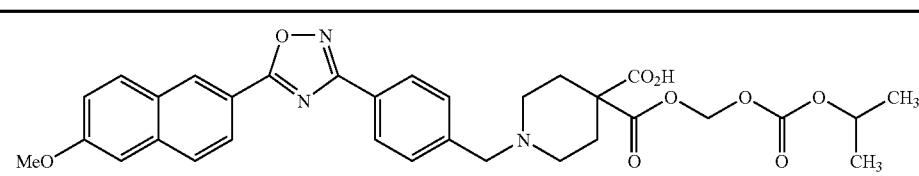 | |

| | R | R₁ | R₂ | R₃ | R₄ | R₇ | R₈ |
|---|---|---|---|---|---|---|---|
| 129 | Ph | F | H | H | H | H | —OCH₂Ph |
| 130 | Ph | F | H | H | H | H | —OCH₂CH₃ |
| 131 | Ph | F | H | H | H | —CH₂Ph | (methoxymethyl isopropyl carbonate group) |
| 132 | Ph | F | H | H | H | —CH₂Ph | (4-methyl-5-ethyl-1,3-dioxol-2-one group) |
| 133 | isobutyl (CH(CH₃)CH₂CH₃) | H | H | H | H | CH₃ | (methoxymethyl isopropyl carbonate group) |
| 134 | Ph | F | H | H | H | H | —OCH₂CH₂OCH₃ |
| 135 | Ph | F | H | H | H | H | —OCH₂CH₂CH₂OCH₃ (wait) |
| 136 | Ph | F | H | H | H | —C₂H₅ | —OC₂H₅ |
| 137 | Ph | F | H | H | H | —CH₂Ph | —OCH₂Ph |

Preparation of 1-{4-[5-(2-fluoro biphenyl-4-yl)-[1,2,4]oxadiazol-3-yl]benzyl}-4-(Pyridin-2-ylcarbamoyl)piperidine-4-carboxylic acid benzyl ester Scheme To a stirred solution of 1-{4-[5-(2-fluorobiphenyl-4-yl)-[1,2,4]oxadiazol-3-yl]benzyl}piperidine-4,4-dicarboxylic acid benzyl ester (0.8 g, 0.0014 mol) in dichloromethane (20 mL), oxalyl chloride (0.343 g, 0.0027 mol) is added slowly at 0-50 C. A few drops of N,N-dimethyl formamide is added into it. The reaction mixture is stirred at room temperature for 1.5 hrs. It is then concentrated under reduced pressure to get 4-chlorocarbonyl-1-{4-[5-(2-fluorobiphenyl-4-yl)-[1,2,4]oxadiazol-3-yl]benzyl}piperidine-4-carboxylic acid benzyl ester.

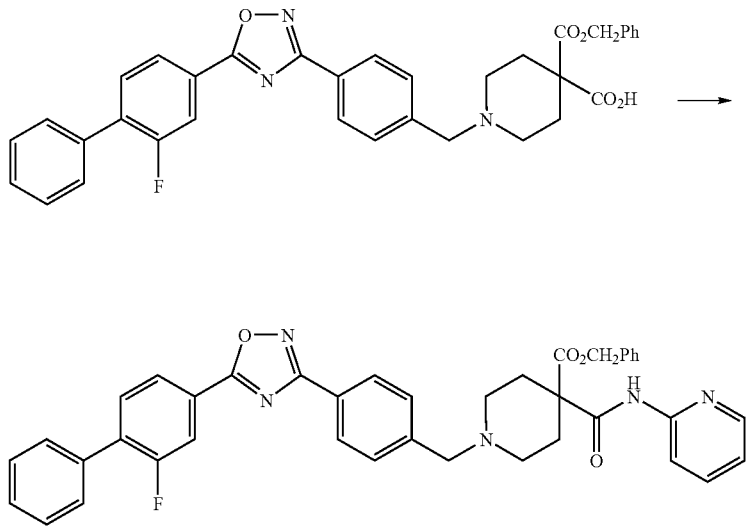

To a stirred solution of triethyl amine (0.34 g, 0.0034 mol) in dichloromethane (20 mL), 2-amino pyridine (0.152 g, 0.0016 mol) is added. A solution of 4-chlorocarbonyl-1-{4-[5-(2-fluorobiphenyl-4-yl)-[1,2,4]oxadiazol-3-yl]benzyl}-piperidine-4-carboxylic acid benzyl ester in dichloromethane (10 mL) is added slowly into the reaction mixture at 0-50 C. It is then stirred at room temperature for 1 hr. Demineralized water (15 mL) is added to the reaction mixture, organic layer is separated and the aqueous layer is extracted with (1×20 mL) dichloromethane. Combined organic layer is dried over sodium sulphate and concentrated under reduced pressure to get the crude material, which is purified by column chromatography (silica gel 230-400 mesh, n-hexane:ethyl acetate 60:40) to furnish 1-{4-[5-(2-fluorobiphenyl-4-yl)-[1,2,4]oxadiazol-3-yl]benzyl}-4-(pyridin-2-ylcarbamoyl)piperidine-4-carboxylic acid benzyl ester (138) (BS6.555).

Further example prepared accordingly.

| | | | | | | | | Compound |
|---|---|---|---|---|---|---|---|---|

| Ex. | R | R1 | R2 | R3 | R4 | R5 | R6 | MS(ES+) |
|---|---|---|---|---|---|---|---|---|
| 138 | Ph | F | H | H | H | OCH₂Ph | (H-N-pyridin-2-yl) | 668.30 |
| 139 | Ph | F | H | H | H | OEt | N(CH₃)₂ | 557.22 | ester 4-ethyl ester (0.5 g) and 1-hydroxybenzotriazole (0.38 g). Allowed to stir the reaction mixture at 25-300 C for 30 mins. Dimethylamine (0.75 mL) followed by EDC HCl (0.38 g) was added in to the above reaction mixture at 25-300 C. Allowed the reaction mixture to stir at 25-300 C for 1-2 hrs. Reaction is followed by TLC. The reaction mixture concentrated under vacuum using rota vapour and the product slurry obtained is suspended in D M Water (5 mL). The product extracted in to ethyl acetate (2×5 mL). The combined product layer dried with sodium sulphate and concentrated under vacuum to yield crude product which in turn purified by a column chromatography to yield pure 4-dimethylcarbamoyl-piperidine-1,4-dicarboxylic acid 1-tert-butyl ester 4-ethyl ester.

Alternative process of preparing 4-dimethylcarbamoyl-piperidine-1,4-dicarboxylic acid 1-tert-butyl ester 4-ethyl ester Step-I

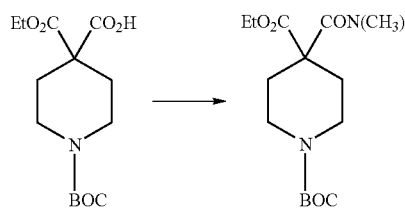

Scheme

THF (5 ml) charged in to a R B flask followed by the addition of piperidine-1,4,4-tricarboxylic acid 1-tert-butyl Step-II

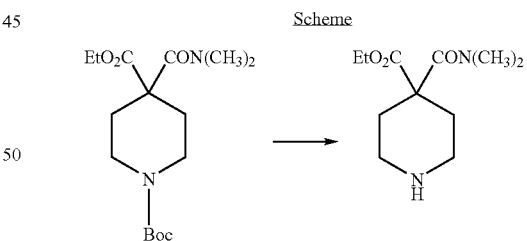

Scheme

4-Dimethylcarbamoyl-piperidine-1,4-dicarboxylic acid 1-tert-butyl ester 4-ethyl ester (0.45 g) was added to a R B flask containing Ethanolic HCl (5 mL). The reaction mixture stirred at RT for 1-2 hrs. Reaction followed by TLC. Solvent is removed under vacuum and D M Water (7 mL) was added in to the product residue. pH of the product solution was adjusted to 8-9 by using 5N NaOH solution (app. 2 mL). The product containing aq. layer was extracted with dichloromethane (3×10 mL).

The combined organic layer dried with sodium sulphate and concentrated under vacuum at 35-400 C to and dried under vacuum for 1-2 hrs to yield 4-dimethylcarbamoyl-piperidine-4-carboxylic acid ethyl ester.

Step-III

Scheme

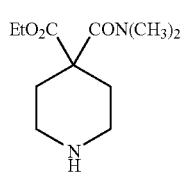

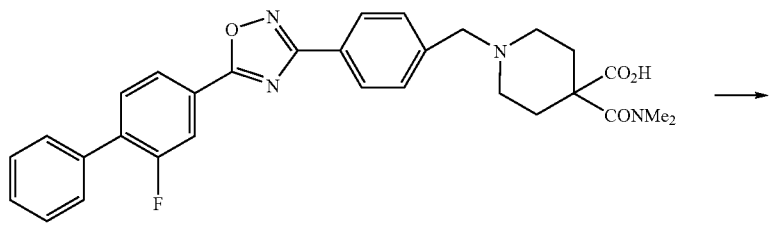

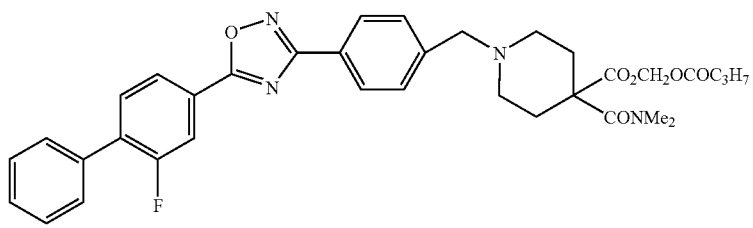

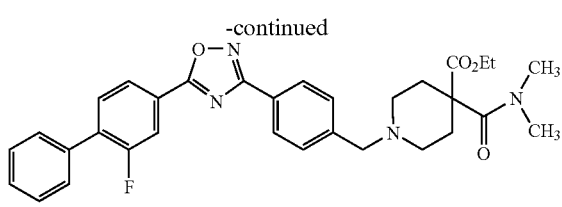

4-[5-(2-Fluoro-biphenyl-4-yl)-[1,2,4]oxadiazol-3-yl]-phenyl}-methanol (0.39 g) was added in to a R B flask containing THF (5 mL) followed by the addition of Triethylamine (0.3 mL). The reaction mixture cooled to 0-50 C and methanesulfonyl chloride (0.13 mL) was added. The reaction mixture warmed to 15-200 C and stirred for 15-30 mins. The reaction was monitored by TLC. The reaction mixture quenched by adding brine solution (10 mL) at 15-200 C and the product extracted with [1:1] Ethyl acetate & THF mixture (2×10 mL). Combined organic layer dried with sodium sulphate and concentrated under vacuum. The product obtained is dissolved in dimethylformamide (5 mL), followed by the addition of diisopropyl ethylamine (0.56 mL) and 4-dimethylcarbamoyl-piperidine-4-carboxylic acid ethyl ester. The reaction mixture was heated to 75-850 C and stirred for 0.5 to 1 hr. The reaction was followed by TLC. The reaction mixture concentrated under vacuum at 55-600 C and the product residue suspended in D M Water (10 mL) and extracted with ethyl acetate (3×10 mL). The combined organic layer containing the product dried over sodium sulphate and concentrated under vacuum to yield the crude product.

The crude product purified by a column chromatography (ethyl acetate & hexane system) to yield pure product of 1-{4-[5-(2-fluoro-biphenyl-4-yl)-[1,2,4]oxadiazol-3-yl]-benzyl}-4,4-dimethyl-piperidine.

Preparation of 4-dimethylcarbamoyl-1-{4-[5-(2-fluorobiphenyl-4-yl)-[1,2,4]oxadiazol-3-yl]-benzyl}-piperidine-4-carboxylicacid butyryloxymethyl ester Potassium carbonate (0.092 g, 0.0007 mol) is added to a solution of t-butyl amine salt of 4-dimethyl carbamoyl-1-{4-[5-(2-fluorobiphenyl-4-yl)-[1,2,4]oxadiazol-3-yl]-benzyl}-piperidine-4-carboxylic acid (0.200 g, 0.0003 mol) in tetrahydrofuran (10 mL). This solution is stirred at room temperature for 10 minutes and then is concentrated under reduced pressure. The residue is dissolved in N,N-dimethyl formamide (5 mL) and stirred at room temperature for 5 minutes. Chloromethyl butyrate (0.068 g, 0.0005 mol) is added to the solution, which is then heated at 800 C for 30 minutes. Reaction mixture is concentrated under reduced, demineralized water (6 mL) is added to the residue and the aqueous layer is extracted with ethyl acetate (2×10 mL). Combined organic layer are concentrated under reduced pressure and the residue is purified by column chromatography (silica gel 230-400 mesh, n-hexane:ethyl acetate 1.5:8.5) to furnish 4-dimethylcarbamoyl-1-{4-[5-(2-fluorobiphenyl-4-yl)-[1,2,4]oxadiazol-3-yl]-benzyl}-piperidine-4-carboxylicacid butyryloxy methyl ester Following compounds are prepared in a similar manner.

| Compound  | | | | | | | | |
|---|---|---|---|---|---|---|---|---|
| Ex. | R | R1 | R2 | R3 | R4 | R5 | R6 | MS(ES+) |
| 140 | Ph | F | H | H | H | 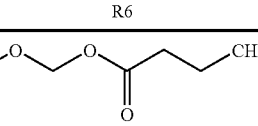 | 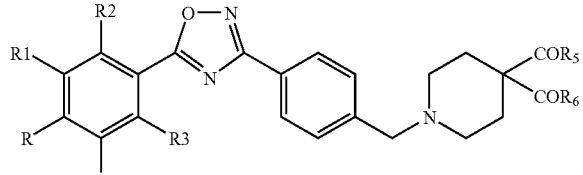 | 629.33 |
| 141 | Ph | F | H | H | H | 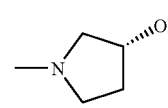 | 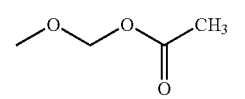 | 643.28 |
| 142 | Ph | F | H | H | H | 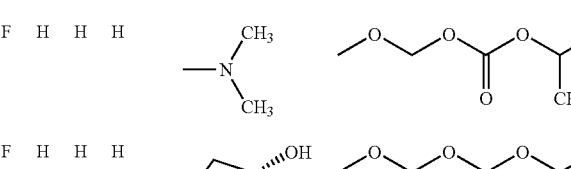 | 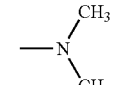 | 645.34 |
| 143 | Ph | F | H | H | H | 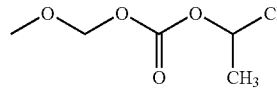 | 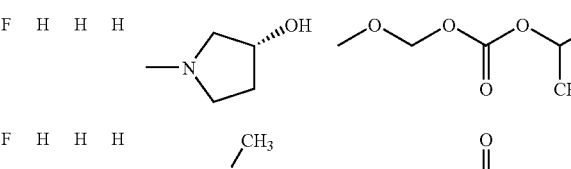 | 687.32 |
| 144 | Ph | F | H | H | H | 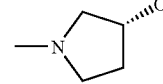 | 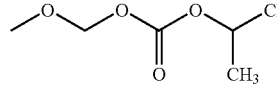 | 627.24 |

Example 138

1H NMR: (CDCl3; 400.13 MHz; δ ppm)

2.18-2.41 (br m, 6H); 2.65-2.75 (br s, 2H); 3.51 (s, 2H); 5.24 (s, 2H); 7.05 (t, J=6.74 Hz, 1H); 7.27-7.38 (br m, 5H); 7.44 (d, J=7.61 Hz, 3H); 7.50 (t, J=7.12 Hz, 2H); 7.59-7.67 (m, 3H); 7.70 (t, J=7.21 Hz, 1H); 8.02 (d, J=10.65 Hz, 1H); 8.05-8.19 (m, 4H); 8.27 (d, J=3.91 Hz, 1H); 8.32 (s, 1H)

Example 139

1H NMR: (CDCl3; 400.13 MHz; δ ppm)

1.26 (t, J=6.95 Hz, 3H); 2.08-2.24 (m, 4H); 2.49-2.69 (m, 4H); 2.92 (s, 6H); 3.56 (s, 2H); 4.21 (q, J=7.05 Hz, 2H); 7.42-7.54 (m, 5H); 7.59-7.68 (m, 3H); 8.02 (d, J=10.69 Hz, 1H); 8.06-8.14 (m, 3H).

Example 140

1H NMR: (CDCl3; 400.13 MHz; δ ppm)

0.96 (t, J=7.35 Hz, 3H); 1.63-1.70 (m, 2H); 2.07-2.16 (m, 2H); 2.17-2.25 (m, 2H); 2.32 (t, J=7.36 Hz, 2H); 2.51-2.65 (m, 4H); 2.92 (s, 6H); 3.56 (s, 2H); 5.79 (s, 2H); 7.42-7.53 (m, 5H); 7.59-7.68 (m, 3H); 8.02 (d, J=10.68 Hz, 1H); 8.08 (d, J=8.36 Hz, 1H); 8.12 (d, J=7.98 Hz, 2H).

Example 141

1H NMR: (CDCl3; 400.13 MHz; δ ppm)

1.86-2.03 (br d, 2H); 2.10 (s, 3H); 2.13-2.38 (br m, 4H); 2.44-2.70 (br m, 4H); 3.36-3.75 (m merged in s, 6H); 4.45 (s, 1H); 5.62-5.92 (br dd, 2H); 7.41-7.54 (m, 5H); 7.59-7.68 (m, 3H); 8.02 (d, J=10.79 Hz, 1H); 8.07 (d, J=8.14 Hz, 1H); 8.11 (d, J=8.02 Hz, 2H) One exchangeable proton

Example 142

1H NMR: (CDCl3; 400.13 MHz; δ ppm)

1.31 (d, J=6.22 Hz, 6H); 2.08-2.19 (m, 2H); 2.19-2.28 (m, 2H); 2.50-2.65 (m, 4H); 2.92 (s, 6H); 3.56 (s, 2H); 4.91 (quintet, J=6.23 Hz, 1H); 5.79 (s, 2H); 7.41-7.54 (m, 5H); 7.59-7.68 (m, 3H); 8.02 (d, J=10.66 Hz, 1H); 8.08 (d, J=9.02 Hz, 1H); 8.12 (d, J=8.02 Hz, 2H).

Example 143

1H NMR: (CDCl3; 400.13 MHz; δ ppm)

1.30 (d, J=6.16 Hz, 6H); 1.59-2.02 (br d, 2H); 2.09-2.38 (br m, 4H); 2.44-2.75 (br m, 4H); 3.32-3.79 (m merged with s, 6H); 4.45 (s, 1H); 4.84-4.97 (m, 1H); 5.69-5.91 (br t, 2H); 7.40-7.55 (m, 5H); 7.59-7.69 (m, 3H); 8.02 (d, J=11.02 Hz, 1H); 8.07 (d, J=8.86 Hz, 1H); 8.11 (d, J=7.97 Hz, 2H) One exchangeable proton

Example 144

1H NMR: (CDCl3; 400.13 MHz; δ ppm)

1.20 (s, 9H); 2.15-2.30 (m, 4H); 2.49-2.58 (br t, 2H); 2.63-2.71 (m, 2H); 2.99 (s, 6H); 3.56 (s, 2H); 4.92 (s, 2H); 7.40-7.54 (m, 5H); 7.59-7.68 (m, 3H); 8.02 (d, J=10.66 Hz, 2H); 8.05-8.14 (m, 2H).

Further examples were prepared according to the methods described.

| Ex  | Structure | MS(ES+) |
|-----|-----------|---------|
| 145 | 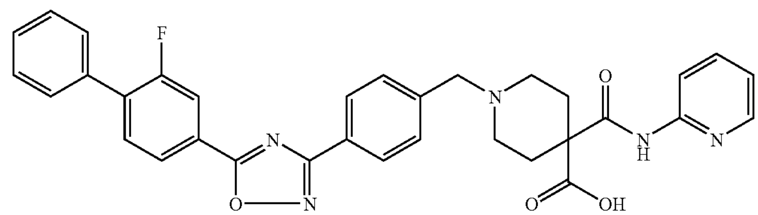 [SMILES: O=C(O)C1(C(=O)Nc2ccccn2)CCN(Cc2ccc(-c3noc(-c4ccc(-c5ccccc5)c(F)c4)n3)cc2)CC1]          | 578.20  |
| 146 | 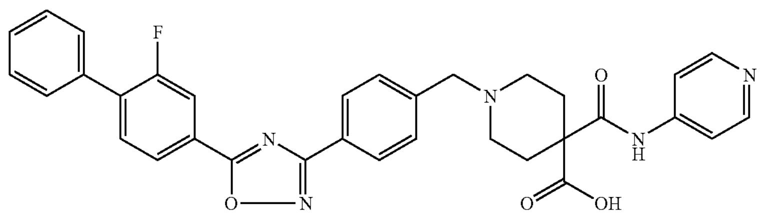 [SMILES: O=C(O)C1(C(=O)Nc2ccncc2)CCN(Cc2ccc(-c3noc(-c4ccc(-c5ccccc5)c(F)c4)n3)cc2)CC1]          | 578.14  |
| 147 | 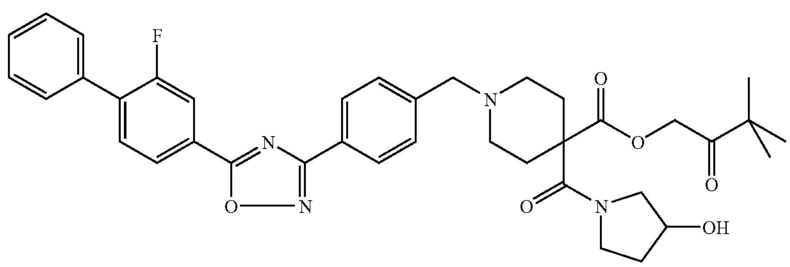 [SMILES: CC(C)(C)C(=O)COC(=O)C1(C(=O)N2CCC(O)C2)CCN(Cc2ccc(-c3noc(-c4ccc(-c5ccccc5)c(F)c4)n3)cc2)CC1]          | 669.23  |
| 148 | 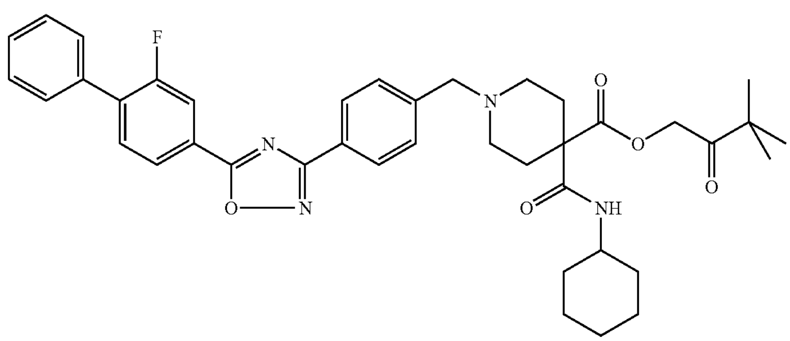 [SMILES: CC(C)(C)C(=O)COC(=O)C1(C(=O)NC2CCCCC2)CCN(Cc2ccc(-c3noc(-c4ccc(-c5ccccc5)c(F)c4)n3)cc2)CC1]          | 681.22  |
| 149 | 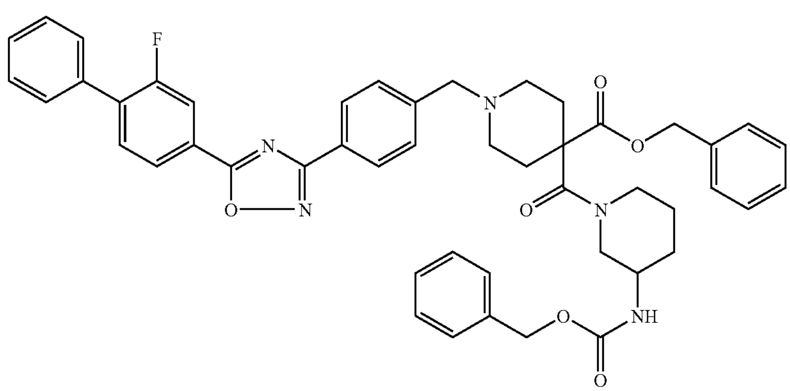 [SMILES: O=C(NC1CCCN(C(=O)C2(C(=O)OCc3ccccc3)CCN(Cc3ccc(-c4noc(-c5ccc(-c6ccccc6)c(F)c5)n4)cc3)CC2)C1)OCc1ccccc1]          | 808.27  |

The following compounds are also of interest:

Preparation of Monocarboxylic Acids

Preparation of 1-{4-[5-(4-fluorobiphenyl-4-yl)-[1,2,4]oxadiazol-3-yl]benzyl}piperidine-4-carboxylic acid Step-I

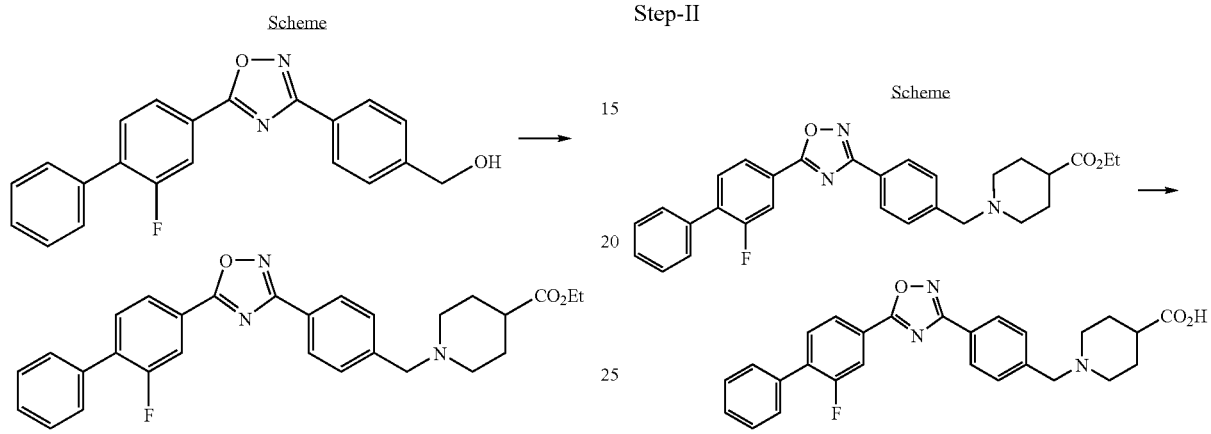

Methanesulfonylchloride (0.20 mL, 0.0026 mol) is added to a stirred solution of {4-[5-(2-fluoro-biphenyl-4-yl)-[1,2,4]oxadiazole-3-yl]-phenyl}-methanol (0.60 g, 0.0017 mol) and triethylamine (0.482 mL, 0.0035 mol) in dichloromethane (20 mL) at 5° C. Reaction mixture is stirred at 5° C. for 30 minutes and then treated with demineralized water (10 mL) at 5° C. Dichloromethane layer is separated and aqueous layer is extracted with dichloromethane (2×10 mL). Combined organic layer is dried over sodium sulphate and concentrated to furnish the crude mesylated product.

To a stirred solution of this mesylate derivative in N,N-dimethylformamide (10 mL), N,N-diisopropylethylamine (0.45 mL, 0.0026 mol) and piperidine-4-carboxylic acid ethyl ester (0.326 g, 0.0021 mol) are added and reaction mixture is heated at 80° C. for 30 minutes. N,N-dimethylformamide is removed under reduced pressure, demineralized water (15 ml) is added to the residue and the aqueous layer is extracted with ethyl acetate (2×20 mL). Combined organic layer is concentrated under reduced pressure and the residue is purified by column chromatography (silica gel 230-400 mesh, n-hexane:ethyl acetate 65:35) to furnish 1-{4-[5-(2-fluoro-biphenyl-4-yl)-[1,2,4]oxadiazol-3-yl]-benzyl}-piperidine-4-carboxylic acid ethyl ester.

Step-II

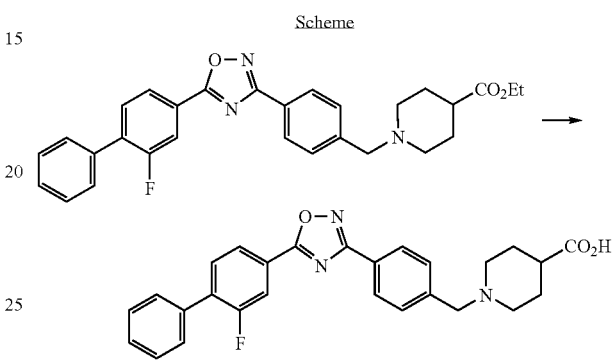

An aqueous solution (2 mL) of sodium hydroxide (0.099 g, 0.0024 mol) is added to a stirred solution of 1-{4-[5-(2-fluoro-biphenyl-4-yl)-[1,2,4]oxadiazol-3-yl]-benzyl}-piperidine-4-carboxylic acid ethyl ester (0.4 g, 0.0008 mol) in a mixture of ethanol (4 mL) and tetrahydrofuran (4 mL). Reaction mixture is refluxed for 6 hrs at 85° C., concentrated under reduced pressure and then treated with demineralized water (15 mL). Aqueous layer is acidified to pH ~2 with 2N HCl. The solid thus formed is filtered, washed with a mixture of methanol:ether (10 mL, 10:90) and dried under reduced pressure to furnish 1-{4-[5-(2-fluoro-biphenyl-4-yl)-[1,2,4]oxadiazol-3-yl]-benzyl}-piperidine-4-carboxylic acid hydrochloride.

| Examples | R | $R_1$ | $R_2$ | $R_3$ | $R_4$ | MS(ES$^+$) |
|---|---|---|---|---|---|---|
| XXVIII | Ph | F | H | H | H | 458.1 |
| XXIX | CF$_3$ | H | H | H | H | 432.2 |
| XXX | Ph | H | H | H | H | 440.2 |
| XXXI | CH(CH$_3$)CH$_2$CH$_3$ | H | H | H | H | 420.2 |
| XXXII | OC$_2$H$_5$ | H | H | H | H | 408.2 |
| XXXIII | OCF$_3$ | H | H | H | H | 448.12 |
| XXXIV | C(CH$_3$)$_3$ | H | H | H | H | 420.20 |
| XXXV | OCH(CH3)2 | H | H | H | H | 422.18 |

-continued

| | Compound | | | | | |
|---|---|---|---|---|---|---|

Structure: benzene ring with R, R1, R2, R3, R4 substituents connected to 1,2,4-oxadiazole linked to phenyl-CH2-piperidine-CO2H

| Examples | R | R₁ | R₂ | R₃ | R₄ | MS(ES⁺) |
|---|---|---|---|---|---|---|
| XXXVI | cyclohexylmethyl | H | H | H | H | 446.2 |
| XXXVII | 4-isopropylcyclohexyl variant (full structure shown) | | | | | 412.24 |
| XXXVIII | 4-isobutylphenyl variant with piperidine-3-CO2H | | | | | 420.21 |
| XIL | 4-isobutylphenyl variant with (R)-piperidine-3-CO2H | | | | | 420.22 |
| XL | biphenyl variant with piperidine-3-CO2H | | | | | 440.19 |
| XLI | 2-fluorobiphenyl variant with piperidine-3-CO2H | | | | | 458.3 |
| XLII | 2-fluorobiphenyl variant with (R)-piperidine-3-CO2H | | | | | 457.9 |

| Compound |
|---|

| Examples | R | R₁ | R₂ | R₃ | R₄ | MS(ES⁺) |
|---|---|---|---|---|---|---|
| XLIII | (structure: 4-cyclohexylphenyl-oxadiazole-phenyl-CH₂-piperidine-3-CO₂H) | | | | | 446.2 |

Example XXVIII as HCl

¹H NMR: (CDCl₃+TFA+CD₃OD+D₂O; 400.13 MHz; δ ppm)

2.15-2.32 (br m, 4H); 2.49-2.59 (br m, 1H); 2.83 (t, J=12.40 Hz, 2H); 3.71 (d, J=12.08 Hz, 2H); 4.32 (s, 2H); 7.41-7.53 (m, 3H); 7.55-7.69 (m, 5H); 7.98 (d, J=10.63 Hz, 1H); 8.05 (d, J=8.04 Hz, 1H); 8.24 (t, J=7.81 Hz, 2H); Two exchangeable protons

Example XXIX as HCl

¹H NMR: (CDCl₃+TFA+CD₃OD+D₂O; 400.13 MHz; δ ppm)

2.15-2.32 (br m, 4H); 2.44-2.56 (br m, 1H); 2.79 (t, J=12.04 Hz, 2H); 3.70 (d, J=12.00 Hz, 2H); 4.32 (s, 2H); 7.58 (d, J=8.12 Hz, 2H); 7.85 (d, J=8.24 Hz, 2H); 8.25 (d, J=7.65 Hz, 2H); 8.35 (d, J=8.13 Hz, 2H) Two exchangeable protons

Example XXX as HCl

¹H NMR: (CDCl₃+DMSO-d₆+TFA+D₂O; 400.13 MHz; δ ppm)

1.94-2.34 (m, 4H); 2.49-2.59 (m, 1H); 2.87-2.97 (br t, 1H); 3.10 (t, J=11.96 Hz, 1H); 3.40-3.48 (br d, 1H); 3.59 (d, J=12.21 Hz, 1H); 4.29 (s, 1H); 4.31 (s, 1H); 7.41-7.47 (m, 1H); 7.51 (t, J=7.77 Hz, 2H); 7.62 (d, J=8.19 Hz, 2H); 7.69 (d, J=7.34 Hz, 2H); 7.82 (d, J=8.36 Hz, 2H); 8.24-8.32 (m, 4H). Two exchangeable protons.

Example XXXI as HCl

¹H NMR: (CDCl₃+DMSO-d₆+TFA+D₂O; 400.13 MHz; δ ppm)

0.94 (d, J=6.62 Hz, 6H); 1.90-2.11 (m, 2H); 2.15-2.32 (m, 3H); 2.59 (d, J=7.19 HZ, 2H); 2.80-2.92 (m, 2H); 3.05 (t, J=11.76 Hz, 1H); 3.42-3.50 (br d, 1H); 3.58-3.67 (br d, 1H); 4.30 (d, J=15.19 Hz, 2H); 7.34-7.36 (br s, 2H); 7.61 (d, J=8.19 Hz, 2H); 8.12 (d, J=8.16 Hz, 2H); 8.21-8.26 (br d, 2H). Two exchangeable protons.

Example XXXII as HCl

¹H NMR: (DMSO-d₆+TFA; 400.13 MHz; δ ppm)

1.43 (t, J=6.95 Hz, 3H); 1.71-1.84 (m, 2H); 2.09-2.25 (m, 2H); 3.00-3.13 (m, 3H); 3.50 (d, J=11.74 Hz, 2H); 4.22 (q, J=7.01 HZ, 2H); 4.46 (s, 2H); 7.24 (d, J=8.84 Hz, 2H); 7.77 (d, J=8.14 Hz, 2H); 8.18 (d, J=8.84 Hz, 2H); 8.22-8.27 (m, 2H). One exchangeable proton.

Example XXXIII as HCl

¹H NMR: (CDCl₃+CD₃OD+TFA; 400.13 MHz; δ ppm)

2.22-2.41 (br m, 4H); 2.46-2.57 (br, 1H); 2.83-3.12 (br m, 2H); 3.37-3.53 (br m, 2H); 4.29, 4.34 (s, 2H); 7.43 (d, J=8.41 Hz, 2H); 7.77 (t, J=7.67 Hz, 2H); 8.22-8.27 (br m, 2H); 8.29 (d, J=8.77 Hz, 2H); Two exchangeable proton

Example XXXIV as HCl

¹H NMR: (CDCl₃+CD₃OD+TFA; 400.13 MHz; δ ppm)

1.39 (s, 9H); 2.13-2.42 (br m, 4H); 2.45-2.56 (br, 1H); 2.80-3.10 (br m, 2H); 3.40-3.65 (br m, 2H); 4.27, 4.32 (s, 2H); 7.60 (d, J=8.37 Hz, 2H); 7.75 (t, J=7.88 Hz, 2H); 8.14 (d, J=8.36 Hz, 2H); 8.21-8.29 (br, 2H); Two exchangeable proton

Example XXXV in the Free Form

¹H NMR: (DMSO-d6+TFA; 400.130 MHz; δ ppm)

1.38 (d, J=5.98 Hz, 6H); 1.70-1.86 (m, 2H); 1.91-2.08 (m, 1H); 2.08-2.27 (m, 2H); 2.82-3.17 (br m, 2H); 3.26-3.42 (m, 1H); 3.49 (d, J=11.71 Hz, 1H); 4.42-4.56 (m, 2H); 4.84 (sep, J=6.05 Hz, 1H); 7.22 (d, J=8.89 Hz, 2H); 7.77 (d, J=8.10 Hz, 2H); 8.17 (d, J=8.80 Hz, 2H); 8.24 (d, J=8.14 Hz, 2H) One exchangeable proton.

Example XXXVI as HCl

¹H NMR: (CDCl₃+CD₃OD+TFA; 400.13 MHz; δ ppm)

1.23-1.36 (br, 1H); 1.37-1.55 (m, 4H); 1.75-1.84 (br d, 1H); 1.84-1.97 (br t, 4H); 2.15-2.29 (br d, 2H); 2.29-2.55 (br, 3H); 2.57-2.67 (br t, 1H); 2.80-2.94 (br, 1H); 2.98-3.09 (br t, 1H); 3.38-3.45 (br d, 1H); 3.54-3.63 (br d, 1H); 4.27, 4.33 (s, 2H); 7.42 (d, J=8.23 Hz, 2H); 7.71-7.79 (br t, 2H); 8.13 (d, J=8.23 Hz, 2H); 8.21-8.28 (br, 2H) Two exchangeable proton Example XXXVII as HCl ¹H NMR: (CDCl₃+CD₃OD+TFA; 400.13 MHz; δ ppm)
0.91 (d, J=6.79 Hz, 6H); 1.1-1.22 (br, 4H); 1.45-1.55 (br, 1H); 1.6-1.74 (br m, 2H); 1.87-1.97 (br d, 2H); 2.15-2.29 (br d, 5H), 2.3-2.54 (br, 1H); 2.78-3.07 (br, m, 3H); 3.34-3.61 (m, 2H); 4.25, 4.30 (s, 2H); 7.71 (t, J=7.96 Hz, 2H); 8.11-8.18 (m, 2H) Two exchangeable proton Example XXXVIII as HCl ¹H NMR: (DMSO-d₆+TFA; 400.130 MHz; δ ppm)
0.94 (d, J=6.61 Hz, 6H); 1.44-1.57 (m, 1H); 1.74-1.90 (br m, 1H); 1.90-2.03 (m, 2H); 2.05-2.14 (br d, 1H); 2.63 (d, J=7.15 Hz, 2H); 2.81-3.15 (br m, 3H); 3.38-3.48 (br d, 1H); 3.57 (d, J=10.60 Hz, 1H); 4.49 (s, 2H); 7.51 (d, J=8.18 Hz, 2H); 7.82 (d, J=8.15 Hz, 2H); 8.16 (d, J=8.17 Hz, 2H); 8.24 (d, J=8.16 Hz, 2H) Two exchangeable protons Example XIL as HCl ¹H NMR: (DMSO-d₆+TFA; 400.13 MHz; δ ppm)
0.94 (d, J=6.57 Hz, 6H); 1.44-1.57 (m, 1H); 1.73-1.87 (m, 1H); 1.91-2.03 (m, 2H); 2.06-2.14 (br d, 1H); 2.64 (d, J=7.12 HZ, 2H); 2.80-3.14 (m, 3H); 3.39-3.48 (br d, 1H); 3.58 (d, J=11.09 Hz, 1H); 4.50 (s, 2H); 7.52 (d, J=8.15 Hz, 2H); 7.82 (d, J=8.17 Hz, 2H); 8.17 (d, J=8.12 HZ, 2H); 8.25 (d, J=8.14 Hz, 2H). Two exchangeable protons.

Example XL as HCl

¹H NMR: (DMSO-d₆+TFA; 400.13 MHz; δ ppm)
1.44-1.59 (m, 1H); 1.80-2.00 (m, 2H); 2.07-2.14 (br d, 1H); 2.85-3.23 (m, 3H); 3.43 (d, J=11.20 Hz, 1H); 3.57 (d, J=11.07 Hz, 1H); 4.50 (s, 2H); 7.49-7.55 (m, 1H); 7.60 (t, J=7.28 Hz, 2H); 7.83-7.89 (m, 4H); 8.05 (d, J=8.14 Hz, 2H); 8.27 (d, J=8.12 Hz, 2H); 8.34 (d, J=8.39 Hz, 2H). Two exchangeable protons.

Example XLI as HCl

¹H NMR: (DMSO-d6+TFA+D2O; 400.130 MHz; δ ppm)
1.45-1.60 (br m, 1H), 1.67-1.83 (br m, 1H); 1.91-2.02 (br d, 1H); 2.05-2.16 (br d, 1H); 2.72-2.86 (br m, 1H); 2.92-3.20 (br m, 2H); 3.36-3.49 (br d, 1H); 3.56 (d, J=11.38 Hz, 1H); 4.47 (s, 2H); 7.49-7.61 (m, 3H); 7.68 (d, J=7.57 Hz, 2H); 7.76-7.82 (br d, 2H); 7.87 (t, J=7.91 Hz, 1H); 8.10 (d, J=11.16 Hz, 1H); 8.15 (d, J=8.08 Hz, 1H); 8.24 (d, J=8.03 Hz, 2H); Two exchangeable protons Example XLII as HCl ¹H NMR: (DMSO-d₆+TFA+D2O; 400.130 MHz; δ ppm)
1.45-1.60 (br m, 1H), 1.69-1.85 (br m, 1H); 1.91-2.02 (br d, 1H); 2.02-2.15 (br d, 1H); 2.71-2.87 (br m, 1H); 2.92-3.20 (br m, 2H); 3.37-3.50 (br d, 1H); 3.50-3.61 (br m, 1H); 4.47 (s, 2H); 7.49-7.61 (m, 3H); 7.68 (d, J=7.59 Hz, 2H); 7.76-7.83 (br d, 2H); 7.87 (t, J=7.91 Hz, 1H); 8.11 (d, J=10.80 Hz, 1H); 8.15 (d, J=8.13 Hz, 1H); 8.23 (d, J=8.10 Hz, 2H); Two exchangeable protons Example XLIII as HCl ¹H NMR: (DMSO-d6+TFA; 400.130 MHz; δ ppm)
1.25-1.38 (br m, 2H); 1.38-1.60 (br m, 4H); 1.72-2.00 (br m, 7H); 2.06-2.15 (br d, 1H); 2.64-2.77 (br t, 1H); 2.83-3.16 (br m, 3H); 3.36-3.48 (br d, 1H); 3.56 (d, J=10.95 Hz, 1H); 4.49 (s, 2H); 7.58 (d, J=8.07 Hz, 2H); 7.84 (d, J=7.85 Hz, 2H); 8.16 (d, J=8.03 Hz, 2H); 8.24 (d, J=7.87 Hz, 2H) Two exchangeable protons Biological Testing:

Human S1P1-5 receptor subtypes were stably expressed in high levels in HEK 293 or CHOK1 cells following transfection with corresponding plasmid constructs. Although the native cells somewhat respond to S1P, the level of expression and responsiveness of the antibiotic-resistant transfected cell lines that were selected is much higher.

When cultivated cells reached 80% confluence, they were collected and, after lysis, cell membranes were collected by centrifugation and washed in buffer containing antiproteases.

Ligand binding assays were performed using 5-20 μg of cell membranes suspended in 20 mM tris-HCl pH 7.4 containing 15 mM NaF and 2.5 mM deoxypyridoxine in a final volume of 250 μl. The radioligand was 0.5 nM ³H-D-erythro-dihydro-S1P incubated in the presence of bovine serum albumin for 1 h after or 2 h-preincubation. Non specific binding was defined from incubations in the presence of 5 μM S1P.

GTP-γ-³⁵S binding was performed using ~5 μg protein of cell membranes suspended in 50 mM tris-HCl pH 7.5 containing 10 mM MgCl₂, 100 mM NaCl and 10 μM GDP. The radioligand was 0.025 nM [³⁵S] GTP-γ-S and non specific binding determined in the presence of 10 μM non-radioactive GTP-γ-S. S1P and receptor agonists enhance the specific binding whereas inverse agonists reduce it. The maximal stimulation elicited by S1P was taken as a reference to define full or partial agonism and calculate the intrinsic activity (i.a.) of compounds.

Typical results shown in Table 1 indicate that compounds of the invention are able to activate S1P1 receptors with a potency similar to that of S1P itself (i.e. with full intrinsic activity and at nanomolar concentrations) without affecting significantly S1P3 receptor.

TABLE 1

| | Agonist activity of selected compounds | | | |
|---|---|---|---|---|
| | | In-Vitro potency EC50 (nM) | | |
| Ex N° | Compound | Edg1 | Edg3 | Edg5 |
| 15 | | 0.7 | >1000 | >1000 |
| 22 | | 2.2 | >1000 | >1000 |
| 25 | | 1.7 | | |
| 54 | | 11.8 | | |
| 62 | | 6.3 | | |

Lymphopenia was assessed in vivo. Experiments were done in Swiss mice strain (n=5 per condition). Compounds were administered orally in suspension in methyl-cellulose 1% from 1 h 30 until 48 hours before the experiments. Blood was taken on anesthetized animal (4% isoflurane) and samples collected in EDTA-containing vacuum tubes. After 5 minutes stirring, cells were counted using ABC vet hemocytometer (Scil vet animal Care)

Typical results shown in Table 2 indicate that compounds of the invention are able to activate S1P1 receptors in vivo.

TABLE 2 in vivo activity of selected compounds

| Ex N° | Compound | Lymphopenia |
|---|---|---|
| 8 | 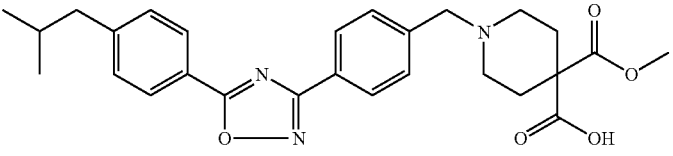 [SMILES: COC(=O)C1(C(=O)O)CCN(Cc2ccc(-c3noc(-c4ccc(CC(C)C)cc4)n3)cc2)CC1] | ED50 = 3.5 mg/kg at 24 h |
| 49 | 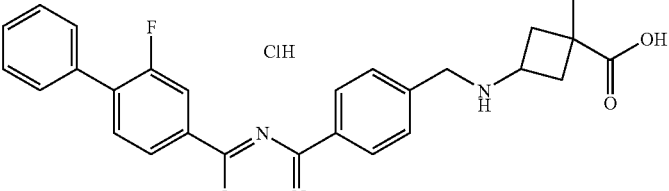 | at 10 mg/kg 86% lymphopenia after 24 h |
| 62 | 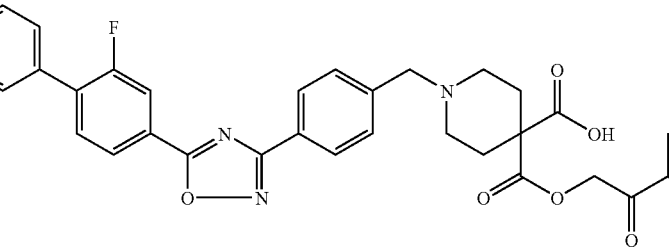 | ED50 = 0.03 mg/kg at 24 h |

The invention claimed is:

1. A compound of formula (I):

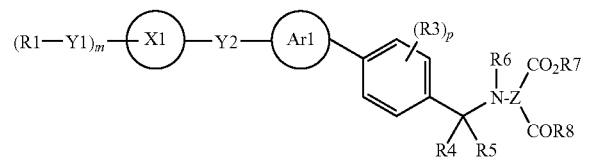

wherein

represents a 1,2,4-oxadiazole group;

X1 is a mono-, or bi-cyclic aryl; a monocyclic heteroaryl; a mono or bicyclic non-aryl heterocyclic; or a mono or bicyclic cycloalkyl comprising one or more unsaturations;

R1 is selected from the group consisting of hydrogen, halo, perfluoro(c1-c6)alkyl, perfluoro(C1-C6)alkoxy, aryl, optionally substituted with halo, arylalkyl, optionally substituted with halo, alkylaryl, alkyl, optionally substituted with alkyl or (C3-C6) cycloalkyl, alkenyl, and cycloalkyl optionally comprising one or more unsaturations;

Y1 represents a bond or Y1 is selected from a group consisting of —O—; —SO$_2$—, and —C(=Q)-, wherein Q is O;

each moiety R1-Y1, identical or different, represents a group that is attached to the cyclic ring structure X1 and m is an integer selected from 1 to 2, wherein m represents the number of positions on X1 substituted with a R1-Y1 moiety;

Y2 represents a bond or Y2 is selected from a group consisting of —O—; —CH$_2$—; —C(O)O—; —C(O)NH—; —S(O)$_q$—, wherein q is 0, 1 or 2; and —C(=Q)-, wherein Q is O, S, N—(R')$_2$ or N—OR', wherein each R' is independently selected from hydrogen, -alkyl, -alkenyl, -alkynyl, -alkoxy, -cycloalkyl or perfluoro(C1-C6)alkyl;

R3 is hydrogen and p is 4;

R4 and R5 are independently selected from the group consisting of hydrogen, methyl and —(C3-C6)cycloalkyl or R4 and R5 together with the C atom to which they are attached form a —(C3-C6)cycloalkyl group;

R6 is selected from the group consisting of hydrogen, -alkyl, -alkenyl, -alkynyl and —(C3-C6)cycloalkyl;

Z represents a —(C3-C6)cycloalkyl group, or R6 and Z form together with the N atom to which they are attached a 5 to 8 membered heterocyclic ring, wherein the alkyl is a C1-C6 linear or branched alkyl; the alkenyl is a C2-C6 linear or branched alkenyl, and aryl is mono- or bicyclic C6-C10;

the —CO₂R7 and —COR8 groups are attached to the same atom, wherein the —CO₂R7 group represents a —CO₂H group or an ester derivative thereof and the —COR8 group represents a —CO₂H group or an ester or an amide derivative thereof, or enantiomers, diastereomers, mixtures and pharmaceutically acceptable salts, or hydrates or solvates thereof.

2. A compound of formula (I) according to claim 1, wherein it is of formula (I-A):

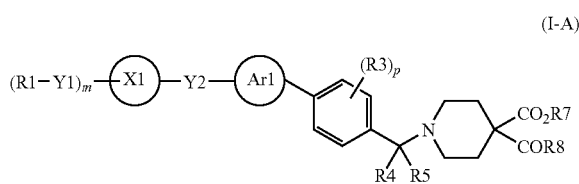

(I-A)

and enantiomers, diastereomers, mixtures, and pharmaceutically acceptable salts, hydrates and solvates thereof, wherein:
X1, R1, Y1, Y2, Ar1, R3, R4, R5, m, p, R7, R8 are defined as in claim 1.

3. A compound according to claim 1, wherein it is of formula (I-B):

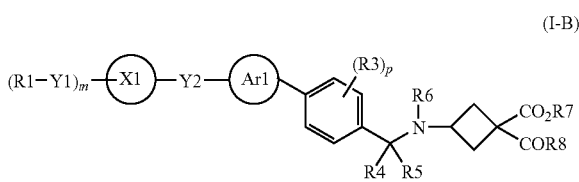

(I-B)

and enantiomers, diastereomers, mixtures, and pharmaceutically acceptable salts, hydrates and solvates thereof, wherein X1, R1, Y1, Y2, Ar1, R3, R4, R5, R6, m, p, R7, R8 are defined as in claim 1.

4. A compound according to claim 1, wherein it is of formula (I-C):

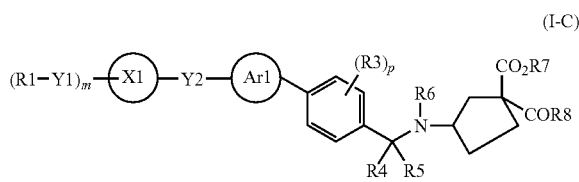

(I-C)

and enantiomers, diastereomers, mixtures, and pharmaceutically acceptable salts, hydrates and solvates thereof, wherein X1, R1, Y1, Y2, Ar1, R3, R4, R5, R6, m, p, R7, R8 are defined as in claim 1.

5. A compound according to claim 1, wherein it is of formula (I-D):

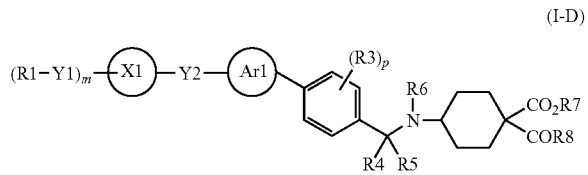

(I-D)

and enantiomers, diastereomers, mixtures, and pharmaceutically acceptable salts, hydrates and solvates thereof, wherein X1, R1, Y1, Y2, Ar1, R3, R4, R5, R6, m, p, R7, R8 are defined as in claim 1.

6. A compound according to claim 1, wherein it is of formula (I-E):

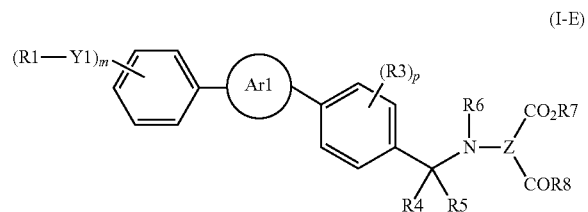

(I-E)

and enantiomers, diastereomers, mixtures, and pharmaceutically acceptable salts, hydrates and solvates thereof wherein:
R1, m, X1, Ar1, R3, R4, R5, R6, R7, R8, p are defined as in claim 1.

7. A compound according to claim 1, wherein it is of formula (I-F):

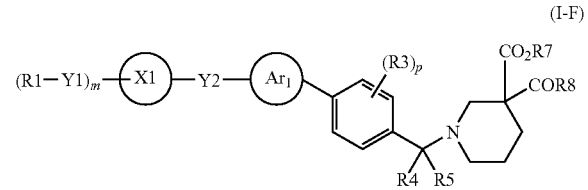

(I-F)

and enantiomers, diastereomers, mixtures, and pharmaceutically acceptable salts, hydrates and solvates thereof, wherein: X1, R1, Y1, Y2, Ar1, R3, R4, R5, R6, m, p, R7, R8 are defined as in claim 1.

8. A compound according to claim 1, wherein:
Ar1 is

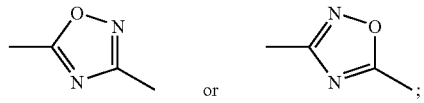

;

X1 is phenyl;
R1 is defined as in claim 1;
Y1 represents a bond or Y1 is selected from a group consisting of —O—; —SO₂—, and —C(=Q)-, wherein Q is O;
each moiety R1-Y1, identical or different, represents a group that is attached to the cyclic ring structure X1 and in is an integer selected from 1 to 2, wherein m represents the number of positions on X1 substituted with a R1-Y1 moiety Y2 represents a bond or Y2 is —CH$_2$— or —C(=Q)-, wherein Q is N—OR', wherein each R' is independently selected from hydrogen, -alkyl, -alkenyl and -alkynyl;

R3 is hydrogen and p is 4;

R4 and R5 are independently selected from the group consisting of hydrogen and methyl;

the —CO$_2$R7 and —COR8 groups are attached to the same atom, wherein the —CO$_2$R7 group represents a —CO$_2$H group or an ester derivative thereof and the —COR8 group represents a —CO$_2$H group or an ester or an amide derivative thereof, wherein the alkyl is a C1-C6 linear or branched alkyl; the alkenyl is a C2-C6 linear or branched alkenyl, and aryl is mono- or bicyclic C6-C10.

9. A compound according to claim 1, wherein Y2 represents a bond or —CH$_2$—.

10. A compound according to claim 1, wherein Y2 represents a bond.

11. A compound according to claim 1, wherein Y1 represents a bond or —O, —SO$_2$—, or —C(=O)—.

12. A compound according to claim 1, wherein Y1 represents a bond.

13. A compound according to claim 1, wherein X1 represents a phenyl group.

14. A compound according to claim 1, wherein R3 represents a hydrogen.

15. A compound according to claim 1, wherein R4 and R5 represent a hydrogen.

16. A compound according to claim 1, wherein R6 represents a hydrogen or alkyl and Z represents a (C3-C6)cycloalkyl or R6 and Z form together with the N atom to which they are attached a 5 to 8 membered heterocycle.

17. A compound according to claim 1, wherein each R1, identical or different, is selected from the group of a halo, an aryl, arylalkyl, alkylaryl, alkyl, alkenyl, (C3-C6)cycloalkyl, with alkyl, aryl and cycloalkyl each being optionally substituted as defined in claim 1.

18. A compound according to claim 1, wherein R1 represents an optionally substituted aryl group as defined in claim 1.

19. A compound according to claim 1, wherein R7 is chosen from H, -Alkyl, perfluoro(C1-C6)alkyl, -Heterocycle, -Alkylheterocycle, -alkylaryl, -Alkyl-O—C(=O)-Alkyl, -Alkyl-O—C(=O)—OAlkyl, -Alkyl-C(=O)-Alkyl, -Alkyl-O—C(=O)—O(C3-C6)Cycloalkyl, where the Heterocycle is optionally substituted with =O or Alkyl.

20. A compound according to claim 1, wherein R8 is chosen from OH, —OAlkyl; —Oalkylaryl —OHeterocycle; —OAlkylheterocycle, wherein the heterocycle is optionally substituted with =O or alkyl; —OAlkyl-O—C(=O)-Alkyl; —OAlkyl-C(=O)-Alkyl; —OAlkyl-O—C(=O)—Oalkyl; —OAlkyl-C(=O)-Aryl wherein the aryl group is unsubstituted or substituted with one or more halogen or alkoxy groups; —OAlkyl-C(=O)-Heteroaryl; —OAlkyl-C(=O)—OAlkyl; —OAlkyl-C(=O)—(C3-C6)Cycloalkyl; —OAlkyl-C(=O)—NTT' where T and T', identical or different, independently represent a hydrogen atom, an alkyl, a cycloalkyl, a hydroxycycloalkyl, a hétéroaryl or a heterocyclic group, or T and T' form together with the N atom to which they are attached a N-containing Heterocycle optionally substituted with =O or alkyl; —OAlkyl-O—C(=O)—OCycloalkyl; —NR$^a$R$^b$, —NR$^a$OR$^b$, natural or synthetic amino acid, wherein each R$^a$ and R$^b$ are independently selected from hydrogen, alkyl, hydroxyalkyl, —O-alkyl, alkenyl, perhaloalkyl, —C3-C6cycloalkyl, heterocycle, heterocyclylalkyl, heteroaryl, and aryl, wherein the cycloalkyl may be substituted by one or more of hydroxyl, wherein the heterocycle moiety may be unsubstituted or substituted with alkyl or R$^a$ and R$^b$ together with the Nitrogen atom to which they are attached, may form a 5-6 membered heterocyclic ring containing 1-2 heteroatoms selected from O and N, wherein the ring is unsubstituted or substituted with hydroxy, hydroxyalkyl, hydroxyalcoxyalkyl, amino, alkylamino, dialkylamino, arylalcoxycarbonylamino, alcoxycarbonylamino.

21. A compound according to claim 1, selected from:
1-{4-[5-(4-isobutylphenyl)-1,2,4-oxadiazol-3-yl]benzyl}piperidine-4,4-dicarboxylic acid
1-(4-{5-[4-(3-methylbut-2-enyloxy)phenyl]-1,2,4-oxadiazol-3-yl}benzyl)piperidine-4,4-dicarboxylic acid
1-{4-[5-(2-fluorobiphenyl-4-yl)-1,2,4-oxadiazol-3-yl]benzyl}piperidine-4,4-dicarboxylic acid
monomethyl 1-{4-[5-(2-fluorobiphenyl-4-yl)-1,2,4-oxadiazol-3-yl]benzyl}piperidine-4,4-dicarboxylate
1-{4-[5-(4-cyclopropylmethylphenyl)-1,2,4-oxadiazol-3-yl]benzyl}piperidine-4,4-dicarboxylic acid
monomethyl 1-{4-[5-(4-cyclopropylmethylphenyl)-1,2,4-oxadiazol-3-yl]benzyl}piperidine-4,4-dicarboxylate
monomethyl 1-(4-{5-[4-(3-methyl-but-2-enyloxy)phenyl]-1,2,4-oxadiazol-3-yl}benzyl)piperidine-4,4-dicarboxyate
monomethyl 1-{4-[5-(4-isobutylphenyl)-1,2,4-oxadiazol-3-yl]benzyl}piperidine-4,4-dicarboxylate
monomethyl 1-{4-[5-(2,2-dimethyl-2,3-dihydrobenzofuran-5-yl)-1,2,4-oxadiazol-3-yl]benzyl}piperidine-4,4-dicarboxylate
1-{4-[5-(2,2-dimethyl-2,3-dihydro-1-benzofuran-5-yl)-1,2,4-oxadiazol-3-yl]benzyl}piperidine-4,4-dicarboxylic acid
1-{4-[5-(2',4'-difluorobiphenyl-4-yl)-1,2,4-oxadiazol-3-yl]benzyl}piperidine-4,4-dicarboxylic acid
1-{4-[5-(4'-fluorobiphenyl-4-yl)-1,2,4-oxadiazol-3-yl]benzyl}piperidine-4,4-dicarboxylic acid
1-{4-[5-(3',5'-difluorobiphenyl-4-yl)-1,2,4-oxadiazol-3-yl]benzyl}piperidine-4,4-dicarboxylic acid
1-{4-[5-(4-trifluoromethylphenyl)-1,2,4-oxadiazol-3-yl]benzyl}piperidine-4,4-dicarboxylic acid
1-[4-(5-biphenyl-4-yl-1,2,4-oxadiazol-3-yl)benzyl]piperidine-4,4-dicarboxylic acid
1-{4-[5-(4-trifluoromethoxyphenyl)-1,2,4-oxadiazol-3-yl]benzyl}piperidine-4,4-dicarboxylic acid
1-{4-[5-(2,3-difluorophenyl)-1,2,4-oxadiazol-3-yl]benzyl}piperidine-4,4-dicarboxylic acid
1-{4-[5-(4-methanesulfonylphenyl)-1,2,4-oxadiazol-3-yl]benzyl}piperidine-4,4-dicarboxylic acid
1-(4-{5-[4-(4-chlorophenyl)cyclohexyl]-1,2,4-oxadiazol-3-yl}benzyl)piperidine-4,4-dicarboxylic acid
1-{4-[5-(1,1-dimethyl-1,3-dihydro-2-benzofuran-5-yl)-1,2,4-oxadiazol-3-yl]benzyl}piperidine-4,4-dicarboxylic acid
1-(4-{5-[4-(2,2,2-trifluoroethoxy)phenyl]-1,2,4-oxadiazol-3-yl}benzyl)piperidine-4,4-dicarboxylic acid
1-{4-[5-(furan-2-ylmethoxyiminomethyl)-1,2,4-oxadiazol-3-yl]benzyl}piperidine-4,4-dicarboxylic acid
1-{4-[5-(4-benzylphenyl)-1,2,4-oxadiazol-3-yl]benzyl}piperidine-4,4-dicarboxylic acid
1-{4-[5-(4-isopropylcyclohexyl)-1,2,4-oxadiazol-3-yl]benzyl}piperidine-4,4-dicarboxylic acid
1-{4-[5-(4-isopropenylcyclohex-1-enyl)-1,2,4-oxadiazol-3-yl]benzyl}piperidine-4,4-dicarboxylic acid 1-{4-[3-(1,1-dimethyl-1,3-dihydro-2-benzofuran-5-yl)-1,2,4-oxadiazol-5-yl]benzyl}piperidine-4,4-dicarboxylic acid
1-{4-[3-(2-fluorobiphenyl-4-yl)-1,2,4-oxadiazol-5-yl]benzyl}piperidine-4,4-dicarboxylic acid
1-{4-[5-(6,6-dimethylbicyclo[3.1.1]hept-2-en-2-ylmethyl)-1,2,4-oxadiazol-3-yl]benzyl}piperidine-4,4-dicarboxylic acid
1-{4-[5-(4-benzoylphenyl)-1,2,4-oxadiazol-3-yl]benzyl}piperidine-4,4-dicarboxylic acid
1-{4-[5-(6-methoxynaphthalen-2-yl)-1,2,4-oxadiazol-3-yl]benzyl}piperidine-4,4-dicarboxylic acid
1-{4-[5-(4-benzyl-2,3-difluorophenyl)-1,2,4-oxadiazol-3-yl]benzyl}piperidine-4,4-dicarboxylic acid
1-{4-[5-(4-isobutyrylphenyl)-1,2,4-oxadiazol-3-yl]benzyl}piperidine-4,4-dicarboxylic acid
1-(4-{5-[4-(2,3-difluorobenzyl)phenyl]-1,2,4-oxadiazol-3-yl}benzyl)piperidine-4,4-dicarboxylic acid
1-{4-[5-(4-ethoxyphenyl)-1,2,4-oxadiazol-3-yl]benzyl}piperidine-4,4-dicarboxylic acid
1-{4-[5-(4-tert-butylphenyl)-1,2,4-oxadiazol-3-yl]benzyl}piperidine-4,4-dicarboxylic acid
1-{4-[5-(4-isopropoxyphenyl)-1,2,4-oxadiazol-3-yl]benzyl}piperidine-4,4-dicarboxylic acid
1-{4-[5-(4-cyclohexylphenyl)-1,2,4-oxadiazol-3-yl]benzyl}piperidine-4,4-dicarboxylic acid
mono-1-(acetyloxy)ethyl 1-{4-[5-(2-fluorobiphenyl-4-yl)-1,2,4-oxadiazol-3-yl]benzyl}piperidine-4,4-dicarboxylate
mono(2,2-dimethylpropanoyloxy)methyl 1-{4-[5-(2-fluorobiphenyl-4-yl)-1,2,4-oxadiazol-3-yl]benzyl}piperidine-4,4-dicarboxylate
mono-5-methyl-2-oxo[1,3]dioxol-4-ylmethyl 1-{4-[5-(2-fluorobiphenyl-4-yl)-1,2,4-oxadiazol-3-yl]benzyl}piperidine-4,4-dicarboxylate
mono(isopropoxycarbonyloxy)methyl 1-{4-[5-(2-fluorobiphenyl-4-yl)-1,2,4-oxadiazol-3-yl]benzyl}piperidine-4,4-dicarboxylate
mono-1-(cyclohexyloxycarbonyloxy)ethyl 1-{4-[5-(2-fluorobiphenyl-4-yl)-1,2,4-oxadiazol-3-yl]benzyl}piperidine-4,4-dicarboxylate
1-(acetyloxy)ethyl methyl 1-{4-[5-(2-fluorobiphenyl-4-yl)-1,2,4-oxadiazol-3-yl]benzyl}piperidine-4,4-dicarboxylate
1-(acetyloxy)ethyl methyl 1-{4-[5-(4-isobutylphenyl)-1,2,4-oxadiazol-3-yl]benzyl}piperidine-4,4-dicarboxylate
(isopropoxycarbonyloxy)methyl methyl 1-{4-[5-(2-fluorobiphenyl-4-yl)-1,2,4-oxadiazol-3-yl]benzyl}piperidine-4,4-dicarboxylate
methyl 5-methyl-2-oxo-[1,3]dioxol-4-ylmethyl 1-{4-[5-(2-fluorobiphenyl-4-yl)-1,2,4-oxadiazol-3-yl]benzyl}piperidine-4,4-dicarboxylate
di(isopropoxycarbonyloxy)methyl 1-{4-[5-(2-fluorobiphenyl-4-yl)-1,2,4-oxadiazol-3-yl]benzyl}piperidine-4,4-dicarboxylate
3-{4-[5-(4-isobutylphenyl)-1,2,4-oxadiazol-3-yl]benzylamino}cyclobutane-1,1-dicarboxylic acid
3-{4-[5-(2-fluorobiphenyl-4-yl)-1,2,4-oxadiazol-3-yl]benzylamino}-cyclobutane-1,1-dicarboxylic acid
3-({4-[5-(4-isobutylphenyl)-1,2,4-oxadiazol-3-yl]benzyl}-methylamino)cyclobutane-1,1-dicarboxylic acid
3-({4-[5-(2-fluorobiphenyl-4-yl)-1,2,4-oxadiazol-3-yl]benzyl}-methylamino)cyclo-butane-1,1-dicarboxylic acid
monomethyl 3-({4-[5-(2-fluorobiphenyl-4-yl)-1,2,4-oxadiazol-3-yl]benzyl}methyl-amino)cyclobutane-1,1-dicarboxylate
monomethyl 3-({4-[5-(4-isobutylphenyl)-1,2,4-oxadiazol-3-yl]benzyl}methyl-amino)cyclobutane-1,1-dicarboxylate
monomethyl 3-({4-[5-(4-isobutylphenyl)-1,2,4-oxadiazol-3-yl]benzyl}methyl-amino)cyclobutane-1,1-dicarboxylate
3-{4-[5-(4-isobutylphenyl)-1,2,4-oxadiazol-3-yl]benzylamino}cyclopentane-1,1-dicarboxylic acid
3-{4-[5-(4-cyclopropylmethylphenyl)-1,2,4-oxadiazol-3-yl]benzylamino}cyclopentane-1,1-dicarboxylic acid
4-{4-[5-(4-isobutylphenyl)-1,2,4-oxadiazol-3-yl]benzylamino}cyclohexane-1,1-dicarboxylic acid
4-{4-[5-(2-fluorobiphenyl-4-yl)-1,2,4-oxadiazol-3-yl]benzylamino}cyclohexane-1,1-dicarboxylic acid
4-({4-[5-(2-fluorobiphenyl-4-yl)-1,2,4-oxadiazol-3-yl]benzyl}methyl-amino)cyclohexane-1,1-dicarboxylic acid,
1-{4-[5-(2-fluorobiphenyl-4-yl)-[1,2,4]oxadiazol-3-yl]-benzyl}-piperidine-4,4-dicarboxylic acid, 2-oxo-3,3-dimethylbutyl ester
1-{4-[5-(2-Fluoro-biphenyl-4-yl)-[1,2,4]oxadiazol-3-yl]-benzyl}piperidine-4,4-dicarboxylic acid (2-oxo-2-phenyl-ethyl)ester
1-{4-[5-(2-Fluoro-biphenyl-4-yl)-[1,2,4]oxadiazol-3-yl]-benzyl}piperidine-4,4-dicarboxylic acid (2-oxo-propyl)ester
1-{4-[5-(2-Fluoro-biphenyl-4-yl)-[1,2,4]oxadiazol-3-yl]benzyl}-piperidine-4,4-dicarboxylic acid (2-furan-2-yl-2-oxo-ethyl)ester
1-{4-[5-(2-Fluoro-biphenyl-4-yl)-[1,2,4]oxadiazol-3-yl]benzyl}-piperidine-4,4-dicarboxylic acid [2-(4-chlorophenyl)-2-oxo-ethyl]ester
1-{4-[5-(2-Fluoro-biphenyl-4-yl)-[1,2,4]oxadiazol-3-yl]benzyl}piperidine-4,4-dicarboxylic acid (2-morpholin-4-yl-ethyl)ester
1-{4-[5-(2-Fluoro-biphenyl-4-yl)-[1,2,4]oxadiazol-3-yl]benzyl}-piperidine-4,4-dicarboxylic acid ethoxycarbonylmethylester
1-{4-[5-(2-Fluoro-biphenyl-4-yl)-[1,2,4]oxadiazol-3-yl]-benzylpiperidine-4,4-dicarboxylic acid (3-methyl-2-oxo-butyl)ester
1-{4-[5-(2-Fluoro-biphenyl-4-yl)-[1,2,4]oxadiazol-3-yl]benzyl]-piperidine-4,4-dicarboxylic acid [2-(4-methoxy-phenyl)-2-oxo-ethyl]ester
1-{4-[5-(2-Fluoro-biphenyl-4-yl)-[1,2,4]oxadiazol-3-yl]benzyl}-piperidine-4,4-dicarboxylic acid (2-cyclopropyl-2-oxo-ethyl)ester
1-{4-[5-(2-Fluoro-biphenyl-4-yl)[1,2,4]-oxadiazol-3-yl]benzyl}-piperidine-4,4-dicarboxylic acid [2-oxo-2-(2-oxopyrrolidin-1-yl)-ethyl]ester
1-{4-[5-(2-Fluoro-biphenyl-4-yl)-[1,2,4]-oxadiazol-3-yl]-benzyl}-piperidine-4,4-dicarboxylic acid dimethylcarbamoylmethyl ester
1-{4-[5-(2-Fluoro-biphenyl-4-yl)-[1,2,4]-oxadiazol-3-yl]-benzyl}-piperidine-4,4-dicarboxylic acid benzyl ester 3,3-dimethyl-2-oxo-butyl ester
1-{4-[5-(2-Fluoro-biphenyl-4-yl)-[1,2,4]-oxadiazol-3-yl]-benzyl}-piperidine-4,4-dicarboxylic acid benzyl ester 3-methyl-2-oxo-butyl ester
1-{4-[5-(2-Fluoro-biphenyl-4-yl)-[1,2,4]-oxadiazol-3-yl]-benzyl}-piperidine-4,4-dicarboxylic acid methylcarbamoylmethyl ester 1-{4-[5-(2-Fluoro-biphenyl-4-yl)-[1,2,4]-oxadiazol-3-yl]-benzyl}-piperidine-4,4-dicarboxylic acid (tert-butylcarbamoyl-methyl)ester
1-{4-[5-(2-Fluoro-biphenyl-4-yl)-[1,2,4]-oxadiazol-3-yl]benzyl}-piperidine-4,4-dicarboxylic acid ethylcarbamoylmethyl ester
1-{4-[5-(2-Fluoro-biphenyl-4-yl)-[1,2,4]-oxadiazol-3-yl]-benzyl}-piperidine-4,4-dicarboxylic acid [2-oxo-2-(pyrrolidin-1-yl)-ethyl)ester
1-{4-[5-(2-Fluoro-biphenyl-4-yl)-[1,2,4]-oxadiazol-3-yl]-benzyl}-piperidine-4,4-dicarboxylic acid [2-oxo-(2-piperidin-1-yl)-ethyl]ester
1-{4-[5-(2-Fluoro-biphenyl-4-yl)-[1,2,4]-oxadiazol-3-yl]-benzyl}-piperidine-4,4-dicarboxylic acid (isopropylcarbamoyl-methyl)ester
1-{4-[5-(2-Fluoro-biphenyl-4-yl)-[1,2,4]-oxadiazol-3-yl]-benzyl}-piperidine-4,4-dicarboxylic acid cyclopropylcarbamoylmethyl ester
1-{4-[5-(2-Fluoro-biphenyl-4-yl)-[1,2,4]oxadiazol-3-yl]-benzyl}-piperidine-4,4-dicarboxylic acid (isobutylcarbamoyl-methyl)ester
1-{4-[5-(2-Fluoro-biphenyl-4-yl)-[1,2,4]oxadiazol-3-yl]-benzyl}-piperidine-4,4-dicarboxylic acid carbamoylmethyl ester
1-{4-[5-(2-Fluoro-biphenyl-4-yl)-[1,2,4]oxadiazol-3-yl]-benzyl}-piperidine-4,4-dicarboxylic acid butylcarbamoylmethyl ester
1-{4-[5-(2-Fluoro-biphenyl-4-yl)-[1,2,4]oxadiazol-3-yl]-benzyl}-piperidine-4,4-dicarboxylic acid cyclopentylcarbamoylmethyl ester
1-{4-[5-(2-Fluoro-biphenyl-4-yl)-[1,2,4]oxadiazol-3-yl]-benzyl}-piperidine-4,4-dicarboxylic acid (piperidin-1-ylcarbamoylmethyl)ester
1-{4-[5-(2-Fluoro-biphenyl-4-yl)-[1,2,4]-oxadiazol-3-yl]-benzyl}-piperidine-4,4-dicarboxylic acid cyclohexylcarbamoylmethyl ester
1-{4-[5-(2-Fluoro-biphenyl-4-yl)-[1,2,4]-oxadiazol-3-yl]-benzyl}-piperidine-4,4-dicarboxylic acid cyclobutylcarbamoylmethyl ester
1-{4-[5-(2-Fluoro-biphenyl-4-yl)-[1,2,4]oxadiazol-3-yl]-benzyl}-piperidine-4,4-dicarboxylic acid butanoyloxymethyl ester
1-{4-[5-(2-Fluoro-biphenyl-4-yl)-[1,2,4]-oxadiazol-3-yl]-benzyl}-piperidine-4,4-dicarboxylic acid [(4-hydroxy-cyclohexyl-carbamoyl)-methyl]ester
1-{4-[5-(2-Fluoro-biphenyl-4-yl)-[1,2,4]-oxadiazol-3-yl]-benzyl}-piperidine-4,4-dicarboxylic acid (pyridin-2-ylcarbamoylmethyl)ester
1-{4-[5-(2-Fluoro-biphenyl-4-yl)-[1,2,4]-oxadiazol-3-yl]-benzyl}-4-(piperidin-1-ylcarbamoyl)-piperidine-4-carboxylic acid
1-{4-[5-(2-Fluoro-biphenyl-4-yl)-[1,2,4]-oxadiazol-3-yl]-benzyl}-4-(pyrrolidin-1-ylcarbamoyl)-piperidine-4-carboxylic acid
1-{4-[5-(2-Fluoro-biphenyl-4-yl)-[1,2,4]oxadiazol-3-yl]-benzyl}-piperidine-4,4-dicarboxylic acid pentyl ester
1-{4-[5-(2-Fluoro-biphenyl-4-yl)-[1,2,4]-oxadiazol-3-yl]-benzyl}-piperidine-4,4-dicarboxylic acid phenethyl ester
1-{4-[5-(2-Fluoro-biphenyl-4-yl)-[1,2,4]-oxadiazol-3-yl]-benzyl}-piperidine-4,4-dicarboxylic acid (2,2,2-trifluoro-ethyl)ester
1-{4-[5-(2-Fluoro-biphenyl-4-yl)-[1,2,4]oxadiazol-3-yl]-benzyl}-piperidine-4,4-dicarboxylic acid (3-methyl-oxetan-3-ylmethyl)ester
1-{4-[5-(2-Fluoro-biphenyl-4-yl)[1,2,4]-oxadiazol-3-yl]-benzyl}-piperidine-3,3-dicarboxylic acid
1-{4-[5-(4-Isobutyl-phenyl)-[1,2,4]-oxadiazol-3-yl]-benzyl}-piperidine-3,3-dicarboxylic acid
1-{4-[5-(4-Cyclohexyl-phenyl)-[1,2,4]-oxadiazol-3-yl]-benzyl}-piperidine-3,3-dicarboxylic acid
1-[4-(5-Biphenyl-4-yl-[1,2,4]-oxadiazol-3-yl)-benzyl]-piperidine-3,3-dicarboxylic acid
1-{4-[5-(2-Fluoro-biphenyl-4-yl)-[1,2,4]-oxadiazol-3-yl]-benzyl}-4-isobutylcarbamoyl-piperidine-4-carboxylic acid
1-{4-[5-(2-Fluoro-biphenyl-4-yl)-[1,2,4]-oxadiazol-3-yl]benzyl}-4-(2-hydroxy-ethyl-carbamoyl)-piperidine-4-carboxylic acid
1-{4-[5-(2-Fluoro-biphenyl-4-yl)-[1,2,4]-oxadiazol-3-yl]-benzyl}-4-isopropylcarbamoyl-piperidine-4-carboxylic acid
4-Cyclopropylcarbamoyl-1-{4-[5-(2-fluoro-biphenyl-4-yl)-[1,2,4]-oxadiazol-3-yl]-benzyl}-piperidine-4-carboxylic acid
4-tert-Butylcarbamoyl-1-{4-[5-(2-fluoro-biphenyl-4-yl)-[1,2,4]-oxadiazol-3-yl]-benzyl}-piperidine-4-carboxylic acid
4-[(1-Ethyl-pyrrolidin-2-ylmethyl)-carbamoyl]-1-{4-[5-(2-fluoro-biphenyl-4-yl)-[1,2,4]oxadiazol-3-yl]-benzyl}-piperidine-4-carboxylic acid
1-{4-[5-(2-Fluoro-biphenyl-4-yl)-[1,2,4]-oxadiazol-3-yl]-benzyl}-4-(2-hydroxy-1-hydroxymethyl-ethylcarbamoyl)-piperidine-4-carboxylic acid
4-(2,3-Dihydroxy-propylcarbamoyl)-1-{4-[5-(2-fluoro-biphenyl-4-yl)-[1,2,4]-oxadiazol-3-yl]-benzyl}-piperidine-4-carboxylic acid
1-{4-[5-(2-Fluoro-biphenyl-4-yl)-[1,2,4]-oxadiazol-3-yl]-benzyl}-4-methylcarbamoyl-piperidine-4-carboxylic acid
4-Ethylcarbamoyl-1-{4-[5-(2-fluoro-biphenyl-4-yl)-[1,2,4]oxadiazol-3-yl]-benzyl}-piperidine-4-carboxylic acid
1-{4-[5-(2-Fluoro-biphenyl-4-yl)-[1,2,4]-oxadiazol-3-yl]-benzyl}-4-(piperidine-1-carbonyl)-piperidine-4-carboxylic acid
1-{4-[5-(2-Fluoro-biphenyl-4-yl)-[1,2,4]-oxadiazol-3-yl]-benzyl}-4-[4-(2-hydroxy-ethyl)-piperazine-1-carbonyl]-piperidine-4-carboxylic acid
4-Dimethylcarbamoyl-1-{4-[5-(2-fluoro-biphenyl-4-yl)-[1,2,4]oxadiazol-3-yl]-benzyl}-piperidine-4-carboxylic acid
1-{4-[5-(2-Fluoro-biphenyl-4-yl)-[1,2,4]-oxadiazol-3-yl]-benzyl}-4-(pyrrolidin-1-yl-carbonyl)-piperidine-4-carboxylic acid
4-Cyclohexylcarbamoyl-1-{4-[5-(2-fluoro-biphenyl-4-yl)-[1,2,4]oxadiazol-3-yl]-benzyl}-piperidine-4-carboxylic acid
1-{4-[5-(2-Fluoro-biphenyl-4-yl)-[1,2,4]-oxadiazol-3-yl]-benzyl}-4-(morpholin-4-yl-carbonyl)-piperidine-4-carboxylic acid
4-Cyclobutylcarbamoyl-1-{4-[5-(2-fluoro-biphenyl-4-yl)-[1,2,4]-oxadiazol-3-yl]-benzyl}-piperidine-4-carboxylic acid
4-Cyclopentylcarbamoyl-1-{4-[5-(2-fluoro-biphenyl-4-yl)-[1,2,4]-oxadiazol-3-yl]-benzyl}-piperidine-4-carboxylic acid
1-{4-[5-(2-Fluoro-biphenyl-4-yl)-[1,2,4]-oxadiazol-3-yl]-benzyl}-4-(4-hydroxy-cyclohexylcarbamoyl)-piperidine-4-carboxylic acid
1-{4-[5-(2-Fluoro-biphenyl-4-yl)-[1,2,4]-oxadiazol-3-yl]-benzyl}-4-[(2-hydroxy-ethyl)-methyl-carbamoyl]-piperidine-4-carboxylic acid benzyl ester 4-Cyclohexylcarbamoyl-1-{4-[5-(2-fluoro-biphenyl-4-yl)-[1,2,4]-oxadiazol-3-yl]-benzyl}-piperidine-4-carboxylic acid benzyl ester 4-Dimethylcarbamoyl-1-{4-[5-(2-fluoro-biphenyl-4-yl)-[1,2,4]-oxadiazol-3-yl]-benzyl}-piperidine-4-carboxylic acid benzyl ester 4-[Bis-(2-hydroxy-ethyl)-carbamoyl]-1-{4-[5-(2-fluoro-biphenyl-4-yl)-[1,2,4]oxadiazol-3-yl]-benzyl}-piperidine-4-carboxylic acid benzyl ester 1-{4-[5-(2-Fluoro-biphenyl-4-yl)-[1,2,4]-oxadiazol-3-yl]-benzyl}-4-[(2-hydroxy-ethyl)-methyl-carbamoyl]-piperidine-4-carboxylic acid 1-{4-[5-(2-Fluoro-biphenyl-4-yl)-[1,2,4]-oxadiazol-3-yl]-benzyl}-4-(3-hydroxy-pyrrolidin-1-yl-carbonyl)-piperidine-4-carboxylic acid 1-{4-[5-(2-Fluoro-biphenyl-4-yl)-[1,2,4]-oxadiazol-3-yl]-benzyl}-4-{4-[2-(2-hydroxy-ethoxy)-ethyl]-piperazin-1-yl-carbonyl}-piperidine-4-carboxylic acid 4-[Bis-(2-hydroxy-ethyl)-carbamoyl]-1-{4-[5-(2-fluoro-biphenyl-4-yl)-[1,2,4]-oxadiazol-3-yl]-benzyl}-piperidine-4-carboxylic acid mono(isopropoxycarbonyloxy)methyl 1-{4-[5-(6-methoxynaphthalen-2-yl)-1,2,4-oxadiazol-3-yl]benzyl}piperidine-4,4-dicarboxylate monobenzyl 1-{4-[5-(2-fluorobiphenyl-4-yl)-1,2,4-oxadiazol-3-yl]benzyl}piperidine-3,3-dicarboxylate monoethyl 1-{4-[5-(2-fluorobiphenyl-4-yl)-1,2,4-oxadiazol-3-yl]benzyl}piperidine-3,3-dicarboxylate benzyl (isopropoxycarbonyloxy)methyl 1-{4-[5-(2-fluorobiphenyl-4-yl)-1,2,4-oxadiazol-3-yl]benzyl}piperidine-4,4-dicarboxylate benzyl 5-methyl-2-oxo-[1,3]dioxol-4-ylmethyl 1-{4-[5-(2-fluorobiphenyl-4-yl)-1,2,4-oxadiazol-3-yl]benzyl}piperidine-4,4-dicarboxylate (isopropoxycarbonyloxy)methyl methyl 1-{4-[5-(4-isobutylphenyl)-1,2,4-oxadiazol-3-yl]benzyl}piperidine-4,4-dicarboxylate mono-n-propyl 1-{4-[5-(2-fluorobiphenyl-4-yl)-1,2,4-oxadiazol-3-yl]benzyl}piperidine-4,4-dicarboxylate mono-n-butyl 1-{4-[5-(2-fluorobiphenyl-4-yl)-1,2,4-oxadiazol-3-yl]benzyl}piperidine-4,4-dicarboxylate diethyl 1-{4-[5-(2-fluorobiphenyl-4-yl)-1,2,4-oxadiazol-3-yl]benzyl}piperidine-4,4-dicarboxylate dibenzyl 1-{4-[5-(2-fluorobiphenyl-4-yl)-1,2,4-oxadiazol-3-yl]benzyl}piperidine-4,4-dicarboxylate 1-{4-[5-(2-Fluoro-biphenyl-4-yl)-[1,2,4]oxadiazol-3-yl]-benzyl}-4-(pyridin-2-ylcarbamoyl)-piperidine-4-carboxylic acid benzyl ester 4-Dimethylcarbamoyl-1-{4-[5-(2-fluoro-biphenyl-4-yl)-[1,2,4]oxadiazol-3-yl]-benzyl}-piperidine-4-carboxylic acid ethyl ester 4-Dimethylcarbamoyl-1-{4-[5-(2-fluoro-biphenyl-4-yl)-[1,2,4]oxadiazol-3-yl]-benzyl}-piperidine-4-carboxylic acid butyryloxymethyl ester 1-{4-[5-(2-Fluoro-biphenyl-4-yl)-[1,2,4]oxadiazol-3-yl]-benzyl}-4-(3-hydroxy-pyrrolidine-1-carbonyl)-piperidine-4-carboxylic acid acetoxymethyl ester 4-Dimethylcarbamoyl-1-{4-[5-(2-fluoro-biphenyl-4-yl)-[1,2,4]oxadiazol-3-yl]-benzyl}-piperidine-4-carboxylic acid isopropoxycarbonyloxymethyl ester 1-{4-[5-(2-Fluoro-biphenyl-4-yl)-[1,2,4]oxadiazol-3-yl]-benzyl}-4-(3-hydroxy-pyrrolidine-1-carbonyl)-piperidine-4-carboxylic acid isopropoxycarbonyloxymethyl ester 4-Dimethylcarbamoyl-1-{4-[5-(2-fluoro-biphenyl-4-yl)-[1,2,4]oxadiazol-3-yl]-benzyl}-piperidine-4-carboxylic acid 3,3-dimethyl-2-oxo-butyl ester 1-{4-[5-(2-Fluoro-biphenyl-4-yl)-[1,2,4]-oxadiazol-3-yl]-benzyl}-4-(pyridin-2-ylcarbamoyl)-piperidine-4-carboxylic acid 1-{4-[5-(2-Fluoro-biphenyl-4-yl)-[1,2,4]-oxadiazol-3-yl]-benzyl}-4-(pyridin-4-ylcarbamoyl)-piperidine-4-carboxylic acid 1-{4-[5-(2-Fluoro-biphenyl-4-yl)-[1,2,4]-oxadiazol-3-yl]-benzyl}-4-(3-hydroxy-pyrrolidine-1-carbonyl)-piperidine-4-carboxylic acid 3,3-dimethyl-2-oxo-butyl ester 4-Cyclohexylcarbamoyl-1-{4-[5-(2-fluoro-biphenyl-4-yl)-[1,2,4]oxadiazol-3-yl]-benzyl}-piperidine-4-carboxylic acid 3,3-dimethyl-2-oxo-butyl ester 4-(3-Benzyloxycarbonylamino-piperidine-1-carbonyl)-1-{4-[5-(2-fluoro-biphenyl-4-yl)-[1,2,4]oxadiazol-3-yl]-benzyl}-piperidine-4-carboxylic acid benzyl ester and enantiomers, diastereomers, mixtures, and pharmaceutically acceptable salts, free forms, hydrates and solvates thereof.

22. A process of preparation of a compound according to claim 1, where in formula (I) R7 is H and/or R8 is OH comprising the step of saponifying a corresponding compound of formula (I) wherein R7 and/or R8 represent(s) an ester function.

23. A process of preparation of a compound of formula (I) according to claim 1, wherein R7 and/or R8 represent(s) an ester function comprising the steps of:

i. reacting a corresponding compound of formula (II):

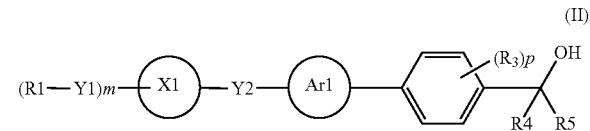

wherein R1, Y1, m, X1, Y2, Ar1, R3, R4, R5 and p are defined as in claim 1 with a suitable sulfonating reagent, and ii. coupling the obtained sulfonated compound with a corresponding compound of formula (III):

where R6, Z, R7 and R8 are defined as in claim 1.

24. A process of preparation of a compound of formula (I) according to claim 1, wherein R7 and/or R8 represent(s) an ester function comprising reacting a corresponding compound of formula (IV):

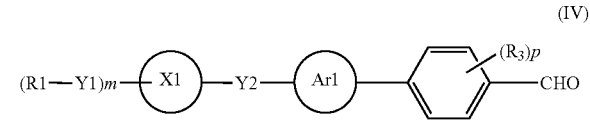

wherein R1, Y1, m, X1, Y2, Ar1, R3 and p are defined as in claim 1 with a compound of formula (III):

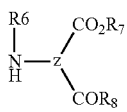

(III)

where R6, Z, R7 and R8 are defined as in claim 1.

25. A process of preparation of a compound of formula (I) according to claim 1, comprising reducing a corresponding compound of formula (V):

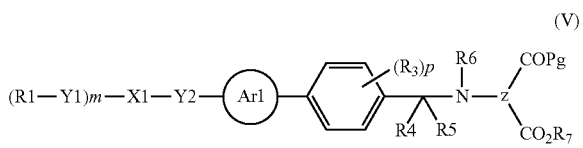

(V)

wherein R1, Y1, m, X1, Y2, Ar1, R3, R4, R5, p, R6, Z, R7 are defined as in formula (I) and Pg represents a protective group of the —COR8 group.

26. Process according to claim 22, which further comprises the additional step of isolating the compound of formula (I).

27. A pharmaceutical composition comprising a compound of formula (I) according to claim 1 with a pharmaceutically acceptable excipient or carrier.

28. Method for providing a compound which acts as an agonist at human S1P1 receptors selectively comprising administering to a patient in the need thereof a compound of formula (I) as defined in claim 1.

29. Method according to claim 28, wherein said method is for decreasing circulating lymphocytes in blood in a patient in the need thereof.

30. Method according to claim 28, wherein the patient is in need of treatment for transplant rejection, tissue graft rejection, immune disorders, autoimmune disorders, inflammatory and chronic inflammatory conditions selected from the group consisting of rheumatoid arthritis, asthma, pollinosis, psoriasis, myocarditis, atopic dermatitis, lymphocytic leukemias, lymphomas, multiple sclerosis, lupus erythematosus, inflammatory bowel diseases, diabetes mellitus, glomerulonephritis, atherosclerosis, multiorgan failure, sepsis, pneumonia, optic neuritis, polymyalgia rheumatica, uveitis, vasculitis, osteoarthritis, respiratory distress syndrome, ischemia reperfusion injury, chronic obstructive pulmonary disease, infection associated with inflammation, viral inflammation, influenza, hepatitis, Guillain-Barre syndrome, chronic bronchitis, restenosis, granulomatous disease, sarcoidosis, leprosy, scleroderma, Alzheimer's disease, disorders related to impaired vascular integrity, cancers, disregulated angiogenesis or excessive neoangiogenesis.

31. Method according to claim 30, wherein said disregulated angiogenesis or excessive neoangiogenesis is selected from ocular angiogenic diseases selected from the group consisting of diabetic retinopathy, choroidal neovascularization, macular degeneration.

32. Method according to claim 30, wherein said cancer selected from the group consisting of solid tumors, hematopoietie cancers and tumor metastases.

33. Method according to claim 28, for topical, cutaneous, ocular, intravaginal, intra-uterine or inhalation administration.

34. Process according to claim 23, which further comprises the additional step of isolating the compound of formula (I).

35. Process according to claim 24, which further comprises the additional step of isolating the compound of formula (I).

36. Process according to claim 25, which further comprises the additional step of isolating the compound of formula (I).

* * * * *